(12) United States Patent
Kamatani et al.

(10) Patent No.: US 7,527,879 B2
(45) Date of Patent: May 5, 2009

(54) LUMINESCENCE DEVICE AND DISPLAY APPARATUS

(75) Inventors: Jun Kamatani, Kawasaki (JP); Shinjiro Okada, Isehara (JP); Akira Tsuboyama, Sagamihara (JP); Takao Takiguchi, Tokyo (JP); Seishi Miura, Sagamihara (JP); Koji Noguchi, Sagamihara (JP); Takashi Moriyama, Kawasaki (JP); Satoshi Igawa, Fujisawa (JP); Manabu Furugori, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/694,754

(22) Filed: Mar. 30, 2007

(65) Prior Publication Data

US 2007/0216294 A1    Sep. 20, 2007

Related U.S. Application Data

(60) Division of application No. 11/329,181, filed on Jan. 11, 2006, which is a division of application No. 10/073,012, filed on Feb. 12, 2002, now Pat. No. 7,147,935, which is a continuation of application No. PCT/JP01/10487, filed on Nov. 30, 2001.

(30) Foreign Application Priority Data

| Nov. 30, 2000 | (JP) | 2000-364650 |
| Mar. 8, 2001 | (JP) | 2001-064205 |
| Apr. 26, 2001 | (JP) | 2001-128928 |

(51) Int. Cl.
*H01L 51/54* (2006.01)
*C09K 11/06* (2006.01)

(52) U.S. Cl. ........... 428/690; 428/917; 313/504; 313/506; 257/40; 257/E51.044; 546/4; 546/10

(58) Field of Classification Search .......... None
See application file for complete search history.

(56) References Cited

U.S. PATENT DOCUMENTS

| 4,176,183 | A | 11/1979 | Baldwin et al. ......... 424/248.52 |
| 4,859,671 | A | 8/1989 | Failli ..................... 514/254 |
| 6,670,645 | B2 * | 12/2003 | Grushin et al. ............ 257/98 |
| 6,733,905 | B2 | 5/2004 | Takiguchi et al. .......... 428/690 |
| 6,780,528 | B2 | 8/2004 | Tsuboyama et al. ........ 428/690 |
| 6,797,980 | B2 | 9/2004 | Takiguchi et al. ........... 257/40 |
| 6,815,091 | B2 | 11/2004 | Takiguchi et al. .......... 428/690 |
| 6,821,646 | B2 | 11/2004 | Tsuboyama et al. ........ 428/690 |
| 6,902,830 | B2 * | 6/2005 | Thompson et al. ......... 428/690 |
| 6,953,628 | B2 | 10/2005 | Kamatani et al. .......... 428/690 |
| 7,001,536 | B2 * | 2/2006 | Thompson et al. ..... 252/301.16 |
| 7,199,392 | B2 * | 4/2007 | Grushin et al. ............ 257/40 |
| 2001/0019782 | A1 | 9/2001 | Igarashi et al. ............ 428/690 |
| 2002/0034656 | A1 | 3/2002 | Thompson et al. ......... 428/690 |
| 2002/0055014 | A1 | 5/2002 | Okada et al. .............. 428/690 |
| 2002/0064683 | A1 | 5/2002 | Okada et al. .............. 428/690 |
| 2002/0121638 | A1 | 9/2002 | Grushin et al. ............. 257/40 |
| 2002/0190250 | A1 | 12/2002 | Grushin et al. ............. 257/40 |
| 2003/0054198 | A1 | 3/2003 | Tsuboyama et al. ........ 428/690 |
| 2003/0068536 | A1 | 4/2003 | Tsuboyama et al. ........ 428/704 |
| 2003/0072964 | A1 | 4/2003 | Kwong et al. ............. 428/690 |
| 2003/0096138 | A1 | 5/2003 | Lecloux et al. ............ 428/690 |
| 2003/0141809 | A1 | 7/2003 | Furugori et al. |

FOREIGN PATENT DOCUMENTS

| EP | 0818512 A1 | 1/1998 |
| EP | 1013740 A2 | 6/2000 |
| EP | 1 175 128 A2 | 1/2002 |
| JP | 2001-181616 | 7/2001 |
| JP | 2001-181617 | 7/2001 |
| JP | 2001-247859 | 9/2001 |
| JP | 2001-345183 | 12/2001 |
| WO | 01/41512 A1 | 6/2001 |
| WO | 02/104080 A1 | 12/2002 |
| WO | 03/040256 A2 | 5/2003 |
| WO | 03/063555 A1 | 7/2003 |

OTHER PUBLICATIONS

Arnold B. Tamayo et al., "Synthesis and Characterization of Facial and Meridional Tris-cyclometallated Iridium (III) Complexes," 125 *J. Am. Chem. Soc.* 7377-87 (2003).

Mirco G. Colombo et al., "Facial Tris Cyclometallated $Rh^{3+}$ and $Ir^{3+}$ Complexes: Their Synthesis, Structure, and Optical Spectroscopic Properties," 33 *Inorg. Chem.* 545-50 (1994).

(Continued)

*Primary Examiner*—Marie R. Yamnitzky
(74) *Attorney, Agent, or Firm*—Fitzpatrick, Cella, Harper & Scinto

(57) ABSTRACT

A metal coordination compound having a structure according to formula (1) or (3), wherein ligand L is a phenylisoquinoline ligand and ligand L2 is different from L:

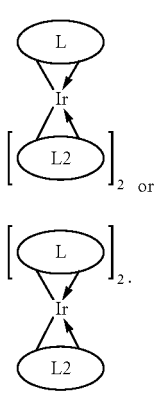

A luminescence device and a display apparatus using this metal coordination compound are provided.

3 Claims, 11 Drawing Sheets

OTHER PUBLICATIONS

Carmen Navarro-Ranninger et al., "A Cyclometallated Pd(II) Complex Containing a Cytosine Model Nucleobase," 558 *J. Organomet. Chem.* 103-10 (1998).

D.F. O'Brien et al., "Improved Energy Transfer in Electrophosphorescent Devices," 74(3) *Applied Phys. Lett.* 442-44 (1999).

M.A. Baldo et al. "Very High-Efficiency Green Organic Light-Emitting Devices Based on Electrophosphorescence," 75 (1) *Applied Phys. Lett.* 4-6 (1999).

P.S. Vincett et al., "Electrical Conduction and Low Voltage Blue Electroluminescence in Vacuum-Deposited Organic Films," 94 *Thin Solid Films* 171-83 (1982).

D.E. Pearson et al., "3-Bromoacetophenone," 40 *Org. Syntheses* 7-10 (1960).

C.H. Chen et al., "Recent Developments in Molecular Organic Electroluminescent Materials," 125 *Macromol Symp.* 1-48 (1997).

William P. Utermohlen, "Improved Synthesis of Quinaldines and 3-Alkyl Quinolines," 8 *J. Org. Chem.* 544-49 (1943).

R.D. Chambers et al., "Polyfluoroheterocyclic Compounds. Part XVIII. Reactions of Heptafluoro-quinoline and -Isoquinoline and Pentafluoropyridine with Hydrogen Halides," *J. Chem. Soc. C.* 61-67 (1971).

R.D. Chambers et al., "Polyfluoroheterocyclic Compounds. Part VII. Heptafluoro-quinoline and -Isoquinoline," *J. Chem. Soc. C.* 2328-31 (1966).

M. Gordon et al., "The Swamping of Catalyst Effect. VI. The Halogenation of Isoquinoline and Quinoline," 29 *J. Org. Chem.* 329-32 (1964).

Supplementary European Search Report in Application No. EP01998553 (Mar. 19, 2007).

Communication pursuant to Article 69(2) in Application No. EP01998553 (Aug. 7, 2007).

Sergey Lamansky et al., "Synthesis and Characterization of Phosphorescent Cyclometalated Iridium Complexes," 40 (3) Inorg. Chem. 1704-11 Mar. 2001).

* cited by examiner

FIG. 1

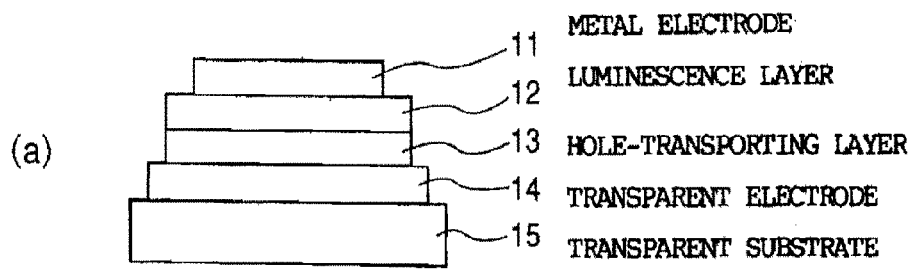

(a)
- 11 METAL ELECTRODE
- 12 LUMINESCENCE LAYER
- 13 HOLE-TRANSPORTING LAYER
- 14 TRANSPARENT ELECTRODE
- 15 TRANSPARENT SUBSTRATE

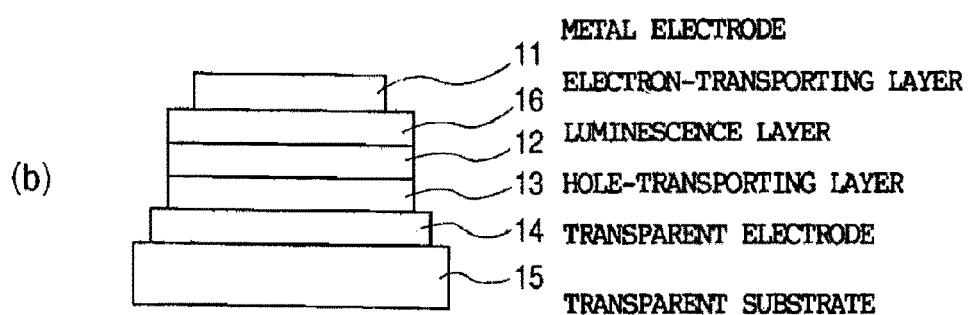

(b)
- 11 METAL ELECTRODE
- 16 ELECTRON-TRANSPORTING LAYER
- 12 LUMINESCENCE LAYER
- 13 HOLE-TRANSPORTING LAYER
- 14 TRANSPARENT ELECTRODE
- 15 TRANSPARENT SUBSTRATE

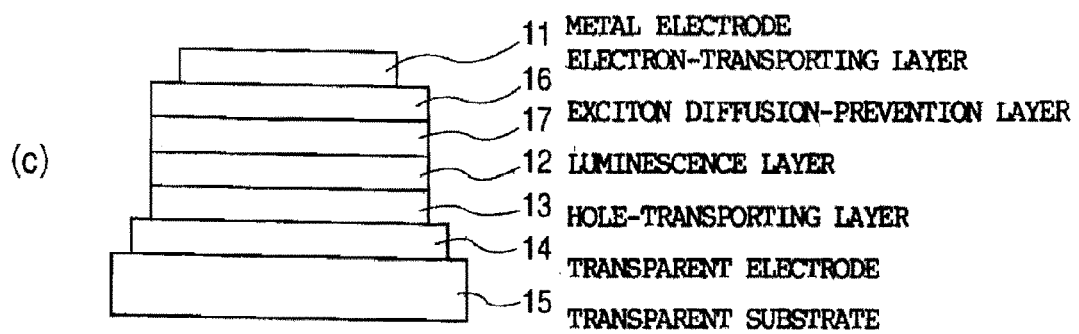

(c)
- 11 METAL ELECTRODE
- 16 ELECTRON-TRANSPORTING LAYER
- 17 EXCITON DIFFUSION-PREVENTION LAYER
- 12 LUMINESCENCE LAYER
- 13 HOLE-TRANSPORTING LAYER
- 14 TRANSPARENT ELECTRODE
- 15 TRANSPARENT SUBSTRATE

LUMINESCENCE DEVICE AND DISPLAY APPARATUS

This application is a division of Ser. No. 11/329,181, filed Jan. 11, 2006, which is a division of application Ser. No. 10/073,012, filed Feb. 12, 2002, now U.S. Pat. No. 7,147,935, which is a continuation of International Application PCT/JP01/10487, filed Nov. 30, 2001. All prior applications are incorporated herein by reference.

TECHNICAL FIELD

The present invention relates to an organic luminescence device (also called an organic electroluminescence device or organic EL device) for use in a planar light source, a planar display, etc. Particularly, the present invention relates to a novel metal coordination compound and a luminescence device having a high luminescence efficiency and causing little change with time by using a metal coordination compound of a specific structure.

BACKGROUND ART

An old example of organic luminescence device is, e.g., one using luminescence of a vacuum-deposited anthracene film (Thin Solid Films, 94 (1982) 171). In recent years, however, in view of advantages, such as easiness of providing a large-area device compared with an inorganic luminescence device, and possibility of realizing desired luminescence colors by development of various new materials and drivability at low voltages, an extensive study thereon for device formation as a luminescence device of a high-speed responsiveness and a high efficiency, has been conducted.

As precisely described in Macromol. Symp. 125, 1-48 (1997), for example, an organic EL device generally has an organization comprising a pair of upper and lower electrodes formed on a transparent substrate, and organic material layers including a luminescence layer disposed between the electrodes.

In the luminescence layer, aluminum quinolinol complexes (inclusive of Alq3 shown hereinafter as a representative example) having an electron-transporting characteristic and a luminescence characteristic, are used for example. In a hole-transporting layer, a material having an electron-donative property, such as a triphenyldiamine derivative (inclusive of α-NPD shown hereinafter as a representative example), is used for example.

Such a device shows a current-rectifying characteristic such that when an electric field is applied between the electrodes, holes are injected from the anode and electrons are injected from the cathode.

The injected holes and electrons are recombined in the luminescence layer to form excitons, which emit luminescence when they are transitioned to the ground state.

In this process, the excited states include a singlet state and a triplet state and a transition from the former to the ground state is called fluorescence and a transition from the latter is called phosphorescence. Materials in theses states are called singlet excitons and triplet excitons, respectively.

In most of the organic luminescence devices studied heretofore, fluorescence caused by the transition of a singlet exciton to the ground state, has been utilized. On the other hand, in recent years, devices utilizing phosphorescence via triplet excitons have been studied.

Representative published literature may include:

Article 1: Improved energy transfer in electrophosphorescent device (D. F. O'Brien, et al., Applied Physics Letters, Vol. 74, No. 3, p. 422 (1999)); and Article 2: Very high-efficiency green organic light-emitting devices based on electrophosphorescence (M. A. Baldo, et al., Applied Physics Letters, Vol. 75, No. 1, p. 4 (1999)).

In these articles, a structure including four organic layers sandwiched between the electrodes, and the materials used therein include carrier-transporting materials and phosphorescent materials, of which the names and structures are shown below together with their abbreviations.

Alq3: aluminum quinolinol complex

α-NPD: N4,N4'-di-naphthalene-1-yl-N4,N4'-diphenyl-biphenyl-4,4'-diamine

CBP: 2,9-dimethyl-4,7-diphenyl-1,10-phenanthroline

PtOEP: platinum-octaethylporphyrin complex

Ir(ppy)₃: iridium-phenylpyridine complex

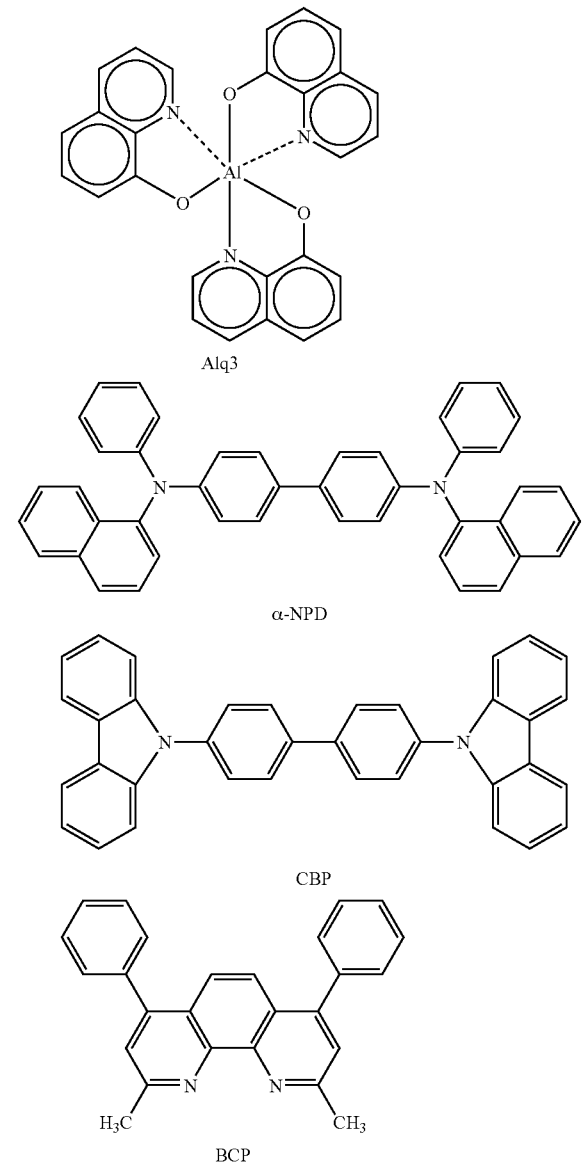

-continued

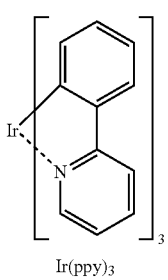

Ir(ppy)₃

The above-mentioned Articles 1 and 2 both have reported structures, as exhibiting a high efficiency, including a hole-transporting layer comprising α-NPD, an electron-transporting layer comprising Alq3, an exciton diffusion-preventing layer comprising BCP, and a luminescence layer comprising CBP as a host and ca 6% of PtOEP or Ir(ppy)₃ as a phosphorescent material dispersed in mixture therein.

Such a phosphorescent material is particularly noted at present because it is expected to provide a high luminescence efficiency in principle for the following reasons. More specifically, excitons formed by carrier recombination comprise singlet excitons and triplet excitons in a probability ratio of 1:3. Conventional organic EL devices have utilized fluorescence of which the luminescence efficiency is limited to at most 25%. On the other hand, if phosphorescence generated from triplet excitons is utilized, an efficiency of at least three times is expected, and even an efficiency of 100%, i.e., four times, can be expected in principle, if a transition owing to intersystem crossing from a singlet state having a higher energy to a triplet state is taken into account.

However, like a fluorescent-type device, such an organic luminescence device utilizing phosphorescence is generally required to be further improved regarding the deterioration of luminescence efficiency and device stability.

The reason of the deterioration has not been fully clarified, but the present inventors consider as follows based on the mechanism of phosphorescence.

In the case where the luminescence layer comprises a host material having a carrier-transporting function and a phosphorescent guest material, a process of phosphorescence via triplet excitons may include unit processes as follows:

1. transportation of electrons and holes within a luminescence layer,
2. formation of host excitons,
3. excitation energy transfer between host molecules,
4. excitation energy transfer from the host to the guest,
5. formation of guest triplet excitons, and
6. transition of the guest triplet excitons to the ground state and phosphorescence.

Desirable energy transfer in each unit process and luminescence are caused in competition with various energy deactivation processes.

Needless to say, a luminescence efficiency of an organic luminescence device is increased by increasing the luminescence quantum yield of a luminescence center material.

Particularly, in a phosphorescent material, this may be attributable to a life of the triplet excitons which is longer by three or more digits than the life of a singlet exciton. More specifically, because it is held in a high-energy excited state for a longer period, it is liable to react with surrounding materials and cause polymer formation among the excitons, thus incurring a higher probability of deactivation process resulting in a material change or life deterioration.

Further, in view of the formation of a full-color display device, luminescence materials providing luminescence colors which are as close as possible to pure three primary colors of blue, green and red, are desired, but there have been few luminescence materials giving a luminescence color of pure red, so that the realization of a good full-color display device has been restricted.

DISCLOSURE OF INVENTION

Accordingly, a principal object of the present invention is to provide a compound capable of high efficiency luminescence and showing a high stability as a luminescent material for use in a phosphorescent luminescence device. Particularly, it is an object to provide a luminescence material compound which is less liable to cause energy deactivation in a long life of excited energy state and is also chemically stable, thus providing a longer device life. A further object of the present invention is to provide a red luminescence material compound capable of emitting pure red suitable for forming a full-color display device.

Inclusively, principal objects of the present invention are to provide a luminescence material which exhibits a high luminescence efficiency, retains a high luminance for a long period and is capable of red luminescence based on phosphorescent luminescence materials, and also provide a luminescence device and a display apparatus using the same.

In the present invention, a metal complex is used as a luminescence material, particularly a novel luminescent metal complex compound comprising iridium as a center metal and an isoquinolyl group as a ligand.

More specifically, the present invention uses as a luminescence material a metal coordination compound having at least one partial structure represented by formula (1) below:

wherein the partial structure ML is represented by formula (2) below:

wherein M is a metal atom of Ir, Pt, Rh or Pd; N and C are nitrogen and carbon atoms, respectively; A is a cyclic group capable of having a substituent, including the carbon atom and bonded to the metal atom M via the carbon atom; B is an isoquinolyl group capable of having a substituent, including the nitrogen atom and bonded to the metal atom M via the nitrogen atom, with the proviso that one or two of CH groups forming the isoquinolyl group can be replaced with a nitrogen atom and the cyclic group A is coordination-bonded to a position-1 carbon atom of the isoquinolyl group.

More specifically, the present invention uses a metal coordination compound having an entire structure represented by formula (3) below:

wherein M is a metal atom of Ir, Pt, Rh or Pd; L and L' are mutually different bidentate ligands; m is 1, 2 or 3, and n is 0, 1 or 2 with the proviso that m+n is 2 or 3; a partial structure ML'$_n$ is represented by formula (4), (5) or (6) shown below:

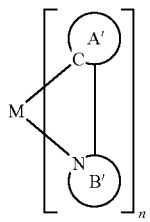

(4)

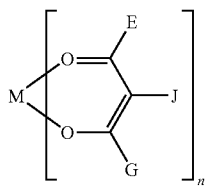

(5)

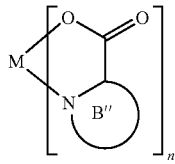

(6)

The present invention also uses as a luminescence material, a metal coordination compound which is entirely represented by formula (7) below:

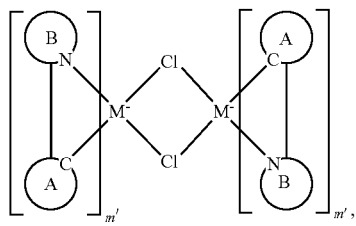

(7)

wherein Cl denotes a chlorine atom, M' denotes iridium Ir or rhodium Rh, and m' is 2.

The present invention also provides high-performance organic luminescence device and display apparatus using the above-mentioned novel metal coordination compound as an organic luminescence material.

Preferred embodiments of the present invention include the following:

A metal coordination compound, wherein n is 0 in the above formula (3).

A metal coordination compound, wherein the cyclic groups A and A' are independently selected from phenyl group, naphthyl group, thienyl group, fluorenyl group, thianaphthyl group, acenaphthyl group, anthranyl group, phenanthrenyl group, pyrenyl group, or carbazolyl group, as an aromatic cyclic group capable of having a substituent with the proviso that the aromatic cyclic group can include one or two CH groups that can be replaced with a nitrogen atom.

A metal coordination compound, wherein the cyclic groups A and A' are selected from phenyl group, 2-naphthyl group, 2-thienyl group, 2-fluorenyl group, 2-thianaphthyl group, 2-anthranyl group, 2-phenanthrenyl group, 2-pyrenyl group, or 3-carbazolyl group, as an aromatic cyclic group capable of having a substituent with the proviso that the aromatic cyclic group can include one or two CH groups that can be replaced with a nitrogen atom.

A metal coordination compound, wherein the aromatic cyclic group is phenyl group capable of having a substituent.

A metal coordination compound, wherein a hydrogen atom is attached to a position-6 carbon atom of the phenyl group capable of having a substituent next to a position-1 carbon atom bonded to the cyclic group B.

A metal coordination compound, wherein the cyclic groups B' and B" are independently selected from isoquinolyl group, quinolyl group, 2-azaanthranyl group, phenanthridinyl group, pyridyl group, oxazolyl group, thiazolyl group, benzoxazolyl group, or benzthiazolyl group, as an aromatic cyclic group capable of having a substituent with the proviso that the aromatic cyclic group can include one or two CH groups that can be replaced with a nitrogen atom.

A metal coordination compound, wherein the cyclic groups B' and B" are selected from isoquinolyl group or pyridyl group, as an aromatic cyclic group capable of having a substituent with the proviso that the aromatic cyclic group can include one or two CH groups that can be replaced with a nitrogen atom.

A metal coordination compound, wherein the cyclic group B' in the formula (4) is isoquinolyl group capable of having a substituent.

A metal coordination compound, wherein the cyclic groups A, A', B, B' and B" are independently non-substituted, or have a substituent selected from a halogen atom or a linear or branched alkyl group having 1 to 20 carbon atoms {of which the alkyl group can include one or non-neighboring two or more methylene groups that can be replaced with —O—, —S—, —CO—, —CO—O—, —O—CO—, —CH=CH—, —C≡C—, or a divalent aromatic group capable of having a substituent (that is a halogen atom, or a linear or branched alkyl group having 1 to 20 carbon atoms (of which the alkyl group can include one or non-neighboring two or more methylene groups that can be replaced with —O—, and the alkyl group can include a hydrogen atom that can be optionally replaced with a fluorine atom)), and the alkyl group can include a hydrogen atom that can be optionally replaced with a fluorine atom}.

A metal coordination compound, wherein the cyclic group A in the formula (7) is selected from phenyl group, naphthyl group, thienyl group, fluorenyl group, thianaphthyl group, acenaphthyl group, anthranyl group, phenanthrenyl group, pyrenyl group, or carbazolyl group, as an aromatic cyclic group capable of having a substituent with the proviso that the aromatic cyclic group can include one or two CH groups that can be replaced with a nitrogen atom.

A metal coordination compound, wherein the aromatic cyclic group is selected from phenyl group, 2-naphthyl group, 2-thienyl group, 2-fluorenyl group, 2-thianaphthyl group, 2-anthranyl group, 2-phenanthrenyl group, 2-pyrenyl group or 3-carbazolyl group, each capable of having a substituent with the proviso that the aromatic cyclic group can include one or two CH groups that can be replaced with a nitrogen atom.

A metal coordination compound, wherein the aromatic cyclic group is phenyl group capable of having a substituent.

A metal coordination compound, wherein a hydrogen atom is attached to a position-6 carbon atom of the phenyl group capable of having a substituent next to a position-1 carbon atom bonded to the cyclic group B.

A metal coordination compound, wherein the cyclic groups A and B in the formula (7) are independently non-substituted, or have a substituent selected from a halogen atom or a linear or branched alkyl group having 1 to 20 carbon atoms {of which the alkyl group can include one or non-neighboring two or more methylene groups that can be replaced with —O—, —S—, —CO—, —CO—O—, —O—CO—, —CH=CH—, —C≡C—, or a divalent aromatic group capable of having a substituent (that is a halogen atom, a cyano atom, a nitro atom, a trialkylsilyl group (of which the alkyl groups are independently a linear or branched alkyl group), a linear or branched alkyl group having 1 to 20 carbon atoms (of which the alkyl group can include one or non-neighboring two or more methylene groups that can be replaced with —O—, and the alkyl group can include a hydrogen atom that can be optionally replaced with a fluorine atom)), and the alkyl group can include a hydrogen atom that can be optionally replaced with a fluorine atom}.

A metal coordination compound, wherein M in the formula (1) is iridium.

A metal coordination compound, wherein M in the formula (7) is iridium.

A metal coordination compound, having a partial structure ML represented by the formula (2) and represented by formula (8) below:

Ir[Rp-Ph-IsoQ-R'q]₃      (8), wherein Ir is iridium; partial structure Ph-IsoQ denotes 1-phenylisoquinolyl group; substituents R and R' are selected from hydrogen, fluorine or a linear or branched alkyl group represented by $C_nH_{2n+1}$ (wherein H can be replaced with F, a non-adjacent methylene group can be replaced with oxygen and n is an integer of 1 to 20), p and q are integers of at least 1 representing numbers of the substituents R and R' bonded to the phenyl group and the isoquinolyl group, respectively, wherein a position-2 carbon atom of the phenyl group and a nitrogen atom of IsoQ are coordination-bonded to Ir.

A metal coordination compound, wherein the partial structure Rp-Ph is 4-alkylphenyl group in the formula (8), and the substituent R' is hydrogen.

A metal coordination compound, wherein in the formula (8), the substituent R is hydrogen, and R'q represents a fluoro or trifluoromethyl group substituted at a 4- or 5-position.

A metal coordination compound, wherein in the formula (8), the partial structure Rp-Ph- is 5-fluorophenyl group, and R'q is a hydrogen atom or a fluorine atom or trifluoromethyl group substituted at a 4- or 5-position.

A metal coordination compound, wherein in the formula (8), the partial structure Rp-Ph- is 4-fluorophenyl group, and R'q is a hydrogen atom or a fluorine atom or trifluoromethyl group substituted at a 4- or 5-position.

A metal coordination compound, wherein in the formula (8), the partial structure Rp-Ph- is 3,5-difluorophenyl group, and R'q is a hydrogen atom or fluorine atom or trifluoromethyl group substituted at a 4- or 5-position.

A metal coordination compound, wherein in the formula (8), the partial structure Rp-Ph- is 3,4,5-trifluorophenyl group, and R'q is a hydrogen atom or a fluorine atom or trifluoromethyl group substituted at a 4- or 5-position.

A metal coordination compound, wherein in the formula (8), the partial structure Rp-Ph- is 4-trifluoromethylphenyl group, and R'q is a hydrogen atom or a fluorine atom or trifluoromethyl group substituted at a 4- or 5-position.

A metal coordination compound, wherein in the formula (8), the partial structure Rp-Ph- is 5-trifluoromethylphenyl group, and R'q is a hydrogen atom or a fluorine atom or trifluoromethyl group substituted at a 4- or 5-position.

A metal coordination compound, wherein in the formula (8), the structure Rp-Ph is a 1-(3,4,5,6-tetrafluorophenyl) group, and in R'q, q is 1 or 6 and R' is a hydrogen atom, a trifluoromethyl group substituted at a 4- or 5-position or such that IsoQ-R'q is a 3,4,5,6,7,8-hexafluoroisoquinoline group.

A metal coordination compound, wherein in the formula (8), the partial structure Rp-Ph- is 4-alkylphenyl group (wherein the alkyl group is a linear or branched alkyl group having 1 to 6 carbon atoms), and R'q is hydrogen.

A metal coordination compound, wherein in the formula (8), the partial structure Rp-Ph- is 4-alkoxyphenyl group (wherein the alkoxy group is a linear or branched alkoxy group having 1 to 6 carbon atoms), and R'q is hydrogen.

A metal coordination compound, wherein in the formala (8), the partial structure Rp-Ph- is a 4-trifluoro-methyloxyphenyl group, and R'q is a hydrogen or fluoro group or trifluoromethyl group substituted at a 4- or 5-position.

A metal coordination compound, which is represented by the formula (3) and is also represented by formula (9) below:

IrL$_m$L'$_n$      (9)

wherein Ir represents iridium.

A metal coordination compound, represented by the formula (9), wherein $L_m$ is represented by a formula of [4-alkylphenylisoquinoline]₂ (wherein the alkyl group is represented by $C_nH_{2n+1}$ and n is an integer of 1 to 8), and L'$_n$ is 1-phenylisoquinoline.

A metal coordination compound, represented by the formula (9), wherein $L_m$ is represented by a formula [1-phenylisoquinoline]₂, and L'$_n$ is 4-alkylphenylisoquinoline (wherein the alkyl group has 1 to 8 carbon atoms).

A metal coordination compound, wherein one or two CH groups in the isoquinolyl group capable of having a substituent in the formula (1) are replaced with a nitrogen atom.

A metal coordination compound, wherein one or two CH groups in the isoquinolyl group capable of having a substituent in the formula (7) are replaced with a nitrogen atom.

An organic luminescence device, comprising: a pair of electrodes disposed on a substrate, and a luminescence unit comprising at least one organic compound disposed between the electrodes, wherein the organic compound comprises a metal coordination compound having at least one partial structure represented by the formula (1) in claim 1.

An organic luminescence device, wherein the organic compound comprises a metal coordination compound having a structure represented by the formula (3).

An organic luminescence device, wherein the organic compound comprises a metal coordination compound having a structure represented by the formula (8).

An organic luminescence device wherein the organic compound comprises a metal coordination compound having a structure represented by the formula (9).

An organic luminescence device, wherein a voltage is applied between the electrodes to emit phosphorescence.

An organic luminescence device, wherein the phosphorescence is red in luminescence color.

A picture display apparatus, comprising the above-mentioned organic luminescence device, and a means for supplying electric signals to the organic luminescence device.

BRIEF DESCRIPTION OF THE DRAWINGS

FIG. 1 illustrates embodiments of the luminescence device according to the present invention.

BEST MODE FOR PRACTICING THE INVENTION

Figure 2:
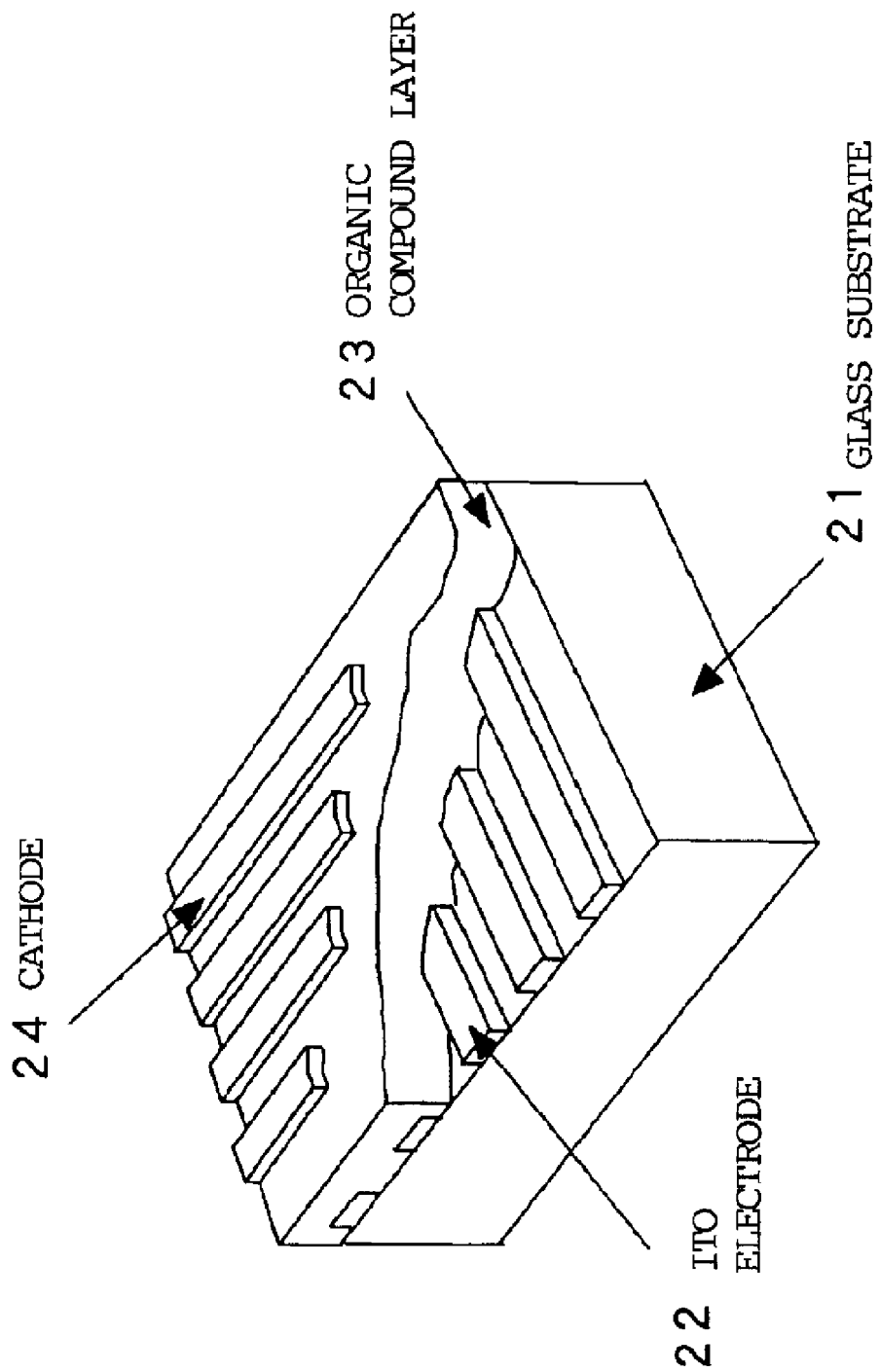
FIG. 2 illustrates a simple matrix-type organic EL device according to Example 8.
Figure 3:
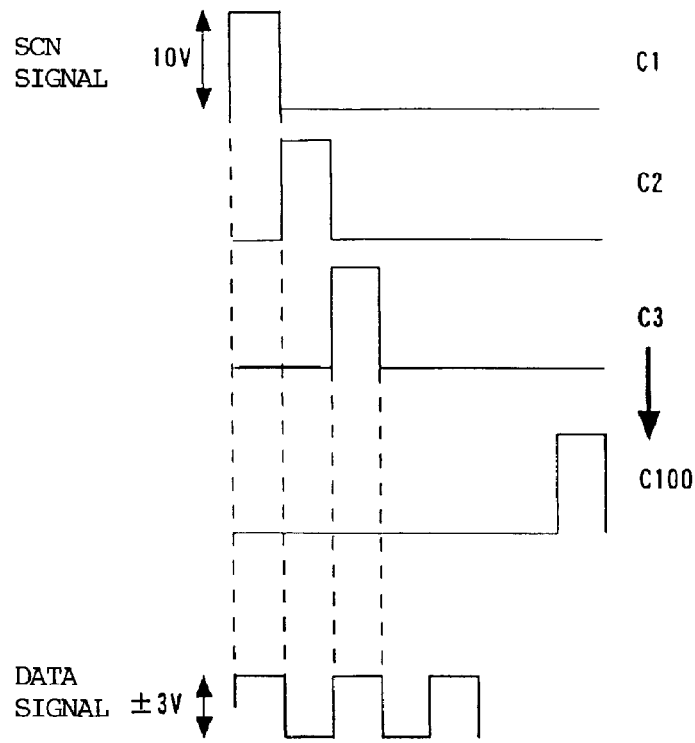
FIG. 3 illustrates drive signals used in Example 8.

Basic structures of organic EL devices formed according to the present invention are illustrated in FIGS. 1(a), (b) and (c).

As shown in FIG. 1, an organic luminescence device generally comprises, on a transparent electrode 15, a 50 to 200 nm-thick transparent electrode 14, a plurality of organic film layers and a metal electrode 11 formed so as to sandwich the organic layers.

FIG. 1(a) shows an embodiment wherein the organic luminescence device comprises a luminescence layer 12 and a hole-transporting layer 13. The transparent electrode 14 may comprise ITO, etc., having a large work function so as to facilitate hole injection from the transparent electrode 14 to the hole-transporting layer 13. The metal electrode 11 comprises a metal material having a small work function, such as aluminum, magnesium or alloys of these elements, so as to facilitate electron injection into the organic luminescence device.

The luminescence layer 12 comprises a compound according to the present invention. The hole-transporting layer 13 may comprise, e.g., a triphenyldiamine derivative, as represented by α-NPD mentioned above, and also a material having an electron-donative property as desired.

A device organized above exhibits a current-rectifying characteristic, and when an electric field is applied between the metal electrode 11 as a cathode and the transparent electrode 14 as an anode, electrons are injected from the metal electrode 11 into the luminescence layer 12, and holes are injected from the transparent electrode 15. The injected holes and electrons are recombined in the luminescence layer 12 to form excitons, which cause luminescence. In this instance, the hole-transporting layer 13 functions as an electron-blocking layer to increase the recombination efficiency at the boundary between the luminescence layer 12 and the hole-transporting layer 13, thereby providing an enhanced luminescence efficiency.

Further, in the structure of FIG. 1(b), an electron-transporting layer 16 is disposed between the metal electrode 11 and the luminescence layer 12 in FIG. 1(a). As a result, the luminescence function is separated from the functions of electron transportation and hole transportation to provide a structure exhibiting more effective carrier blocking, thus increasing the luminescence efficiency. The electron-transporting layer 16, may comprise, e.g., an oxadiazole derivative.

FIG. 1(c) shows another desirable form of a four-layer structure, including a hole-transporting layer 13, a luminescence layer 12, an exciton diffusion prevention layer 17 and an electron-transporting layer 16, successively from the side of the transparent electrode 14 as the anode.

The luminescence materials used in the present invention are most suitably metal coordination compounds represented by the above-mentioned formulae (1) to (9), which are found to cause high-efficiency luminescence in a red region around 600 mm, retain high luminance for a long period and show little deterioration by current passage.

The metal coordination compound used in the present invention emits phosphorescence, and its lowest excited state is believed to be an MLCT* (metal-to-ligand charge transfer) excited state or π- π* excited state in a triplet state, and phosphorescence is caused at the time of transition from such a state to the ground state.

<<Measurement Methods>>

Hereinbelow, methods for measurement of some properties and physical values described herein for characterizing the luminescence material of the present invention will be described.

(1) Judgment between phosphorescence and fluorescence

The identification of phosphorescence was effected depending on whether deactivation with oxygen was caused or not. A solution of a sample compound in chloroform after aeration with oxygen or with nitrogen is subjected to photo-illumination to cause photo-luminescence. The luminescence is judged to be phosphorescence if almost no luminescence attributable to the compound is observed with respect to the solution aerated with oxygen but photo-luminescence is confirmed with respect to the solution aerated with nitrogen. In contrast thereto, in the case of fluorescence, luminescence attributable to the compound does not disappear even with respect to the solution aerated with oxygen. The phosphorescence of all the compounds of the present invention has been confirmed by this method unless otherwise noted specifically.

(2) Phosphorescence yield (a relative quantum yield, i.e., a ratio of an objective sample's quantum yield Φ(sample) to a standard sample's quantum yield Φ(st)) is determined according to the following formula:

$$\Phi(sample)/\Phi(st) = [Sem(sample)/Iabs(sample)]/[Sem(st)/Iabs(st)],$$

wherein Iabs(st) denotes an absorption coefficient at an excitation wavelength of the standard sample; Sem(st), a luminescence spectral areal intensity when excited at the same wavelength: Iabs(sample), an absorption coefficient at an excitation wavelength of an objective compound; and Sem (sample), a luminescence spectral areal intensity when excited at the same wavelength.

Phosphorescence yield values described herein are relative values with respect a phosphorescence yield Φ=1 of Ir(ppy)$_3$ as a standard sample.

(3) A method of measurement of phosphorescence life is as follows.

A sample compound is dissolved in chloroform and spin-coated onto a quartz substrate in a thickness of ca. 0.1 μm and is exposed to pulsative nitrogen laser light at an excitation wavelength of 337 nm at room temperature by using a luminescence life meter (made by Hamamatsu Photonics K.K.) After completion of the excitation pulses, the decay characteristic of luminescence intensity is measured.

When an initial luminescence intensity is denoted by $I_0$, a luminescence intensity after t(sec) is expressed according to the following formula with reference to a luminescence life τ(sec):

$$I=I_0 \cdot \exp(-t/\tau).$$

Thus, the luminescence life τ is a time period in which the luminescence intensity I is attenuated down to 1/e of the initial intensity I ($I/I_0=e^{-1}$, e is a base of natural logarithm). A luminescence life of 80 nsec or longer, particularly 100 nsec or longer, is a second condition to be judged as phosphorescence, whereas fluorescence shows a shorter luminescence life on the order of several tens nsec or shorter.

The luminescence material exhibited high phosphorescence quantum yields of 0.15 to 0.9 and short phosphorescence lives of 0.1 to 10 μsec. A short phosphorescence life becomes a condition for causing little energy deactivation and exhibiting an enhanced luminescence efficiency. More specifically if the phosphorescence life is long, the number of triplet state molecules maintained for luminescence is increased, and the deactivation process is liable to occur, thus resulting in a lower luminescence efficiency particularly at the time of a high-current density. The material of the present invention has a relatively short phosphorescence life thus exhibiting a high phosphorescence quantum yield, and is therefore suitable as a luminescence material for an EL device. The present inventors further consider that the improved performance is attributable to the following.

A difference between a photo-absorption spectrum peak wavelength caused by transition from a single ground state to an excited triplet state and a maximum peak wavelength of luminescence spectrum is generally called a Stokes' shift. The difference in peak wavelength is considered to be caused by a change in energy state of triplet excitons affected by other ground state energy levels. The change in energy state is associated with the Stokes' shift, and a larger amount of the shift generally results in a lowering in maximum luminescence intensity and a broadening of luminescence spectrum leading to a deterioration in monochromaticity of luminescence color. This effect appears particularly remarkably in a red region having a short transition width from the singlet to the triplet.

For example, as for the isoquinoline-type iridium complexes of the present invention, tris(1-phenylisoquinoline-$C^2$,N)iridium (III) (Example Compound No. 1 in Tables 1 to 23 appearing hereafter; abbreviated as Ir(PiQ)$_3$), tris[1-(2-thienyl)-isoquinoline-$C^3$,N]iridium (III) (Example Compound No. 24, abbreviated as Ir(tiQ)$_3$), and tris[1-(9,9-dizaethylfluorene-2-yl)isoquinoline-$C^3$,N]iridium (III) (Example Compound 28, abbreviated as Ir(FliQ)$_3$) exhibited Stokes' shifts of 37 nm, 55 cm and 33 nm, respectively, and relative quantum yields of 0.66, 0.43 and 0.48, respectively.

On the other hand, as for non-isoquinoline-type red luminescence materials, tris[1-thianaphthene-2-yl)pyridine-$C^3$,N]iridium (III) (abbreviated as Ir(BrP)$_3$) and tris[1-(thianaphthene-2-yl)-4-trifluoromethylpyridine (abbreviated as Ir(Bt$_5$CF$_3$Py)$_3$) exhibited remarkably longer Stokes' shifts of 132 nm and 85 nm, respectively, and lower relative quantum yields of 0.29 and 0.12, respectively, compared with the compounds of the present invention.

Even such non-isoquinoline-type red luminescence materials show high quantum yields not achieved by conventional materials, red luminescence materials showing a smaller Stokes' shift, like isoquinoline-type iridium complexes of the present invention, are found to have a tendency of having a still higher quantum yield. A smaller Stokes' shift is considered to provide a larger velocity constant of energy radiation, a shorter phosphorescence life and therefore a higher luminescence efficiency. Based on the above consideration, the introduction of isoquinoline is considered to result in a small Stokes' shift, an enhanced luminescence quantum yield and a better chromaticity.

<<Nomenclature and Structural Expression of Compounds>>

Now, some explanation is added to the manner of structural identification of a metal coordination compound of the present invention and the manner of allotting atomic position number as a basis therefor with reference to Ir(PiQ)$_3$ (Example Compound No. 1), for example. The metal coordination compound has a ligand of 1-phenylisoquinoline of which position numbers are allotted as follows:

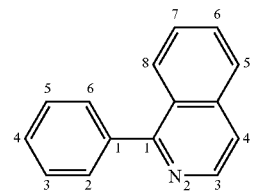

Accordingly, Ir(PiQ)$_3$ formed by coordination of three 1-phenylisoquinoline molecules onto iridium with the position-2 carbon atom of the phenyl group and the nitrogen atom of the isoquinoline ring is named as tris(1-phenylisoquinoline-$C^2$,N)iridium (III).

Ir(PiQ)$_3$ exhibits a high quantum yield as mentioned above, but it has been also found that Ir(PiQ)$_3$ provided with an additional substituent shows a further higher quantum yield in a solution or a solid state film. For example, a class of tris[1-alkylphenyl)isoquinoline-$C^2$,N]iridium (III) formed by attaching alkyl substituents at position-4 of the basic ligand skeleton of 1-phenylisoquinoline exhibits still higher relative quantum yields (i.e., quantum yields when Ir(ppy)$_3$ in a dilute solution in toluene is taken to have a quantum yield of 1). More specifically, the class of compounds have been found to exhibit quantum yields as shown below depending on species of the alkyl substituents. Remarkable increases in quantum yield have been recognized at number of carbon atoms of 4 or more in the subsequent group.

(1) —CH$_3$=0.64
(2) —C(CH$_3$)$_3$=0.7
(3) —C$_4$H$_9$=0.82
(4) —C$_6$H$_{13}$=0.88
(5) —C$_8$H$_{17}$=0.72

From the above results, the addition of a substituent to the above skeleton to weaken the inter-molecular interaction is found to be effective for increasing the luminescence quantum yield.

On the other hand, in the case of using resistance heating vacuum deposition using a tungsten boat for device formation, a material having a molecular weight of at most 1000 has been found suitable in view of the device production process characteristic, such as possibility of vacuum deposition at a low current and a high rate.

More specifically, the above-mentioned class of alkyl chain-added iridium complexes have a tendency of exhibiting a higher vacuum deposition temperature at the time of device formation. The entire molecular weights of thus-alkyl-substituted $Ir(PiQ)_3$ derivatives are as follows depending on the species of alkyl substituents as follows.

(1) —$CH_3$=847
(2) —$C(CH_3)_3$=973
(3) —$C_4H_9$=973
(4) —$C_6H_{13}$=1058
(5) —$C_8H_{17}$=1141

At the time of resistance heating vacuum deposition at $10^{-4}$ Pa, these materials required necessary currents for vacuum deposition as follows depending an the species of alkyl substituents.

(1) —$CH_3$=58 amperes
(2) —$C(CH_3)_3$=61 amperes
(3) —$C_4H_9$=61 amperes
(4) —$C_6H_{13}$=64 amperes
(5) —$C_8H_{17}$=67 amperes Further, a metal coordination compound having a substituent of fluorine atom or a polyfluorinated alkyl can weaken the intermolecular interaction owing to fluorine atoms to lower the vacuum deposition temperature, and is advantageous in that a metal coordination compound of a larger molecular weight can be used as a luminescence material without impairing the vacuum deposition characteristic. For example, the substitution of a trifluoromethyl group for one methyl group can lower the vacuum deposition temperature by ca. 1° C. while the molecular weight is rather increased thereby.

By introducing an isoquinoline skeleton in a metal coordination compound having a structure of a type represented by the above formula (1) or (9), the luminescence wavelength can be adjusted, and it has been found that the metal coordination compound of the present invention wherein the isoquinoline skeleton is bonded to the cyclic group A at its position-1, is unexpectedly advantageous for increasing the luminescence wavelength (i.e., providing red luminescence).

On the other hand, while a known compound of tetrakis(2-phenylpyridine-$C^2$,N) (µ-dichloro)diiridium (III) does not provide a substantial luminescence spectrum, a metal coordination compound of the formula (7) having introduced an isoquinoline skeleton has exhibited a strong luminescence spectrum. From this fact, it is understood that a metal coordination compound of the formula (7) is also suited as a luminescence material for an EL device.

Further, by introducing an electron-attractive substituent or an electron-donative substituent to the metal coordination compound of the present invention, it is possible to adjust the luminescence wavelength. Further, by introducing a substituent group, such as an alkoxy group or a polyfluoroalkyl group, having a large electronic effect and also a stereo-scopically large bulk volume, it becomes possible to effect both a control of luminescence wavelength and a suppression of density extinction due to inter-molecular interaction. Further, the introduction of a substituent group having little electronic effect but having a stereoscopically large bulk volume, such as an alkyl group, is considered to be able to suppress the density extraction without changing the luminescence wavelength.

Further, by replacing one or two CH groups in the isoquinoline ring of a metal coordination compound represented by the formula (1) or (9), the luminescence wavelength can be adjusted without introducing a substituent group.

Also from the above viewpoints, the metal coordination compound of the present invention is suited as a luminescence material for an organic EL device.

Further, a thermal stability is an important property for an organic material constituting an organic EL device. The thermal stability seriously affects the production stability at the time of device production and device stability during operation under current supply. For preparation of organic EL devices, a process of vacuum deposition, spin coating or ink jetting is contemplated. Particularly, in the vacuum deposition process, an organic material is subjected to high temperature for certain period for vaporizing the organic material by sublimation or evaporation and is deposited onto the substrate. Accordingly, the thermal stability of a component material is very important.

Further, also at the time of supplying electricity to the device for causing luminescence, a Joule's heat is locally generated due to passage of a high current. If a component material has a low thermal stability, the material can cause a device deterioration due to such heat. For example, the above-mentioned $Ir(PiQ)_3$ and bis(1-phenylisoquinoline-$C^2$,N)(acetylacetonato)iridium (III) (Example Compound No. 42, abbreviated as $Ir(PiQ)_2$acac) exhibited decomposition temperatures of 380° C. and 340° C., respectively, under nitrogen flow, thus providing a substantial difference in decomposition temperature. More specifically, under a certain vacuum deposition condition, $Ir(PiQ)_3$acac caused an appreciable decomposition in a vacuum deposition chamber, but $Ir(PiQ)_3$ did not cause appreciable decomposition under the same condition. As a result of measurement of decomposition degree under various conditions of vacuum deposition, $Ir(PiQ)_3$ acac exhibited lower upper limits in vacuum deposition speed or degree of vacuum in vacuum deposition, thus exhibiting a narrower production margin at the time of mass production. In this way, a material thermal stability seriously affects the productivity.

In a comparative test, EL devices were prepared from the above-mentioned two luminescence materials through vacuum deposition under decomposition-free condition and subjected to evaluation of luminance deterioration. As a result, when electricity supply was started to provide an initial luminance of 5000 $cd/m^2$, $Ir(PiQ)_3$ and $Ir(PiQ)_2$ acac exhibited luminance half-attenuation periods in a ratio of ca. 3:1, so that $Ir(PiQ)_3$ was substantially stable against electricity supply as represented by a longer luminance half-attenuation period. In this way, the thermal stability of a component material is a factor determining the production stability and performance stability of a device, so that a material having a high thermal stability is desired.

It is believed that the ligand of the present invention, as a result of introduction of isoquinoline skeleton, has a rigid molecular structure, so as to suppress the formation of an excitation-associated molecule resulting in thermal deactivation, thus suppressing energy deactivation due to molecular movement. Further, it is also believed that extinction processes are reduced to result in an improved device performance. In an actual current conduction test, the luminescence material of the present invention, i.e., a metal coordination compound having a ligand comprising an isoquinoline skeleton bonded to a cyclic group A at its 1-position, showed a high stability.

More specifically, a tris(1-substituted isoquinolyl)-metal coordination compound of n=0 in the formula (3) is generally preferred in view of excellent thermal stability.

Accordingly, a luminescence material having a luminescence wavelength of long-wavelength region (red luminescence) and a high chemical stability as well as a high luminescence efficiency has not been realized heretofore but can be realized by the luminescence material of the present invention.

A high-efficiency luminescence device having a layer structure as shown in FIGS. 1(a), (b) and (c) of the present invention is applicable to a product requiring energy economization or a high luminance. More specifically, the luminescence device is applicable to a display apparatus, an illumination apparatus, a printer light source or a backlight for a luminescence layer display apparatus. As a display apparatus, it allows a flat panel display, which is light in weight and provides a highly recognizable display at a low energy consumption. As a printer light source, the luminescence device of the present invention can be used instead of a laser light source of a laser beam printer. For the illumination apparatus or backlight, the energy economization effect according to the present invention can be utilized.

For the application to a display, a drive system using a thin-film transistor (abbreviated as TFT) drive circuit according to an active matrix-scheme, may be used. Hereinbelow, an embodiment of using a device of the present invention in combination with an active matrix substrate is briefly described with reference to FIG. 4.

Figure 4:
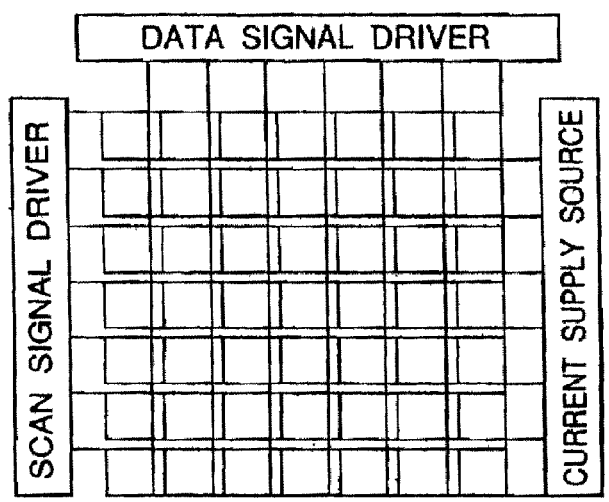
FIG. 4 schematically illustrates a panel structure including an EL device and drive means.

FIG. 4 illustrates an embodiment of panel structure comprising an EL device and drive means. The panel is provided with a scanning signal driver, a data signal driver and a current supply source which are connected to gate selection lines, data signal lines and current supply lines, respectively. At each intersection of the gate selection lines and the data signal lines, a display pixel electrode is disposed. The scanning signal drive sequentially selects the gate selection lines G1, G2, G3 . . . Gn, and in synchronism herewith, picture signals are supplied from the data signal driver to display a printer.

TFT switching devices are not particularly restricted, and devices of a single crystal-silicon substrate, MIM devices or devices of a-Si type can be easily applied.

On the ITO electrodes, one or more organic EL layers and a cathode layer are sequentially disposed to provide an organic EL display panel. By driving a display panel including a luminescence layer comprising a luminescence material of the present invention, it becomes possible to provide a display which exhibits a good picture quality and is stable even for a long period display.

<<Brief Description of Synthesis Path>>

Some synthetic paths for providing a metal coordination compound represented by the above-mentioned formula (1) are illustrated below with reference to an iridium coordination compound for example:

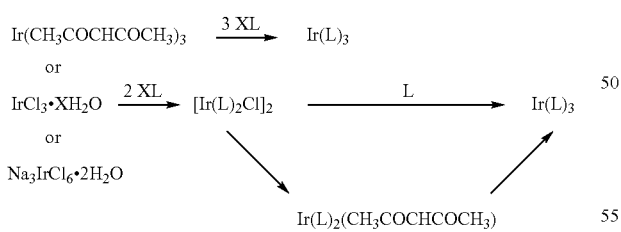

Some specific structural examples of metal coordination compounds used in the present invention are shown in Tables 1 to Tables 23 appearing hereinafter, which are however only representative examples and are not exhaustive. Ph to Iq10 shown in Tables 1 to 23 represent partial structures shown below, corresponding to the above-mentioned formula (3) (or partial structures therein represented by formulae (2), and (4)-(6)) or formula (3). Further, R1-R10 represent substituents in the Ph to Iq10, and E, G and J represent substituents in the formula (5).

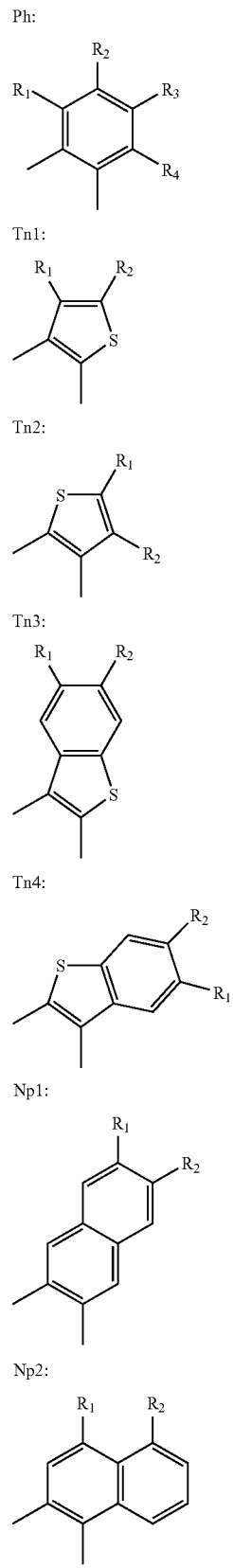

Cn1:
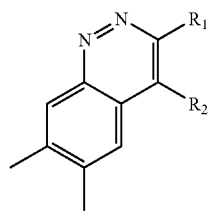
Cn2:
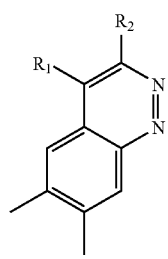
Pe:
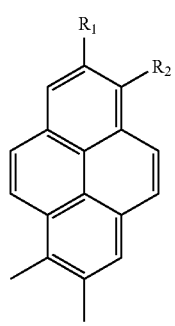
Fl:
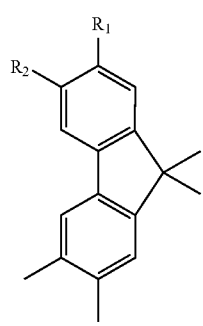
Qn1:
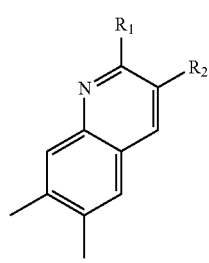
Qn2:
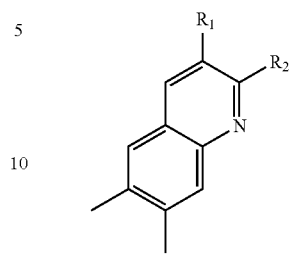
Cz:
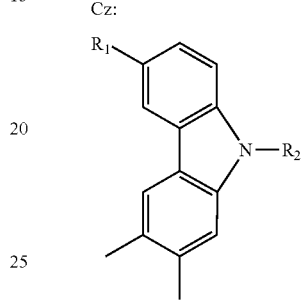
Iq2:
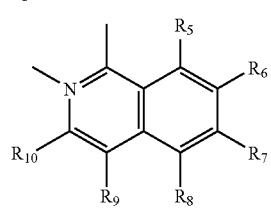
Iq5:
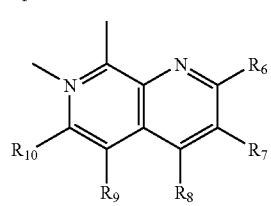
Iq6:
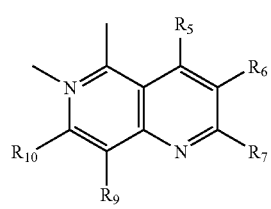
Iq7:
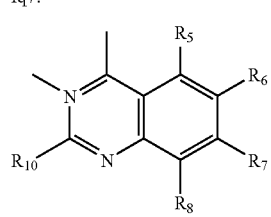

-continued
Iq8:
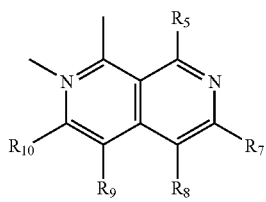
Iq9:
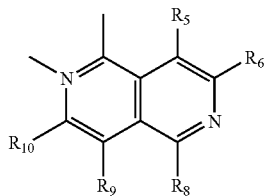
Iq10:
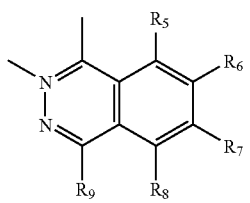
Pr:
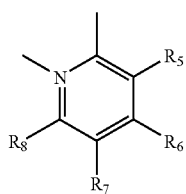
Pi:
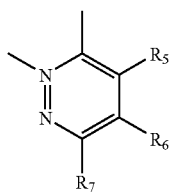
Py1:
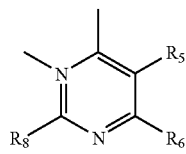
Py2:
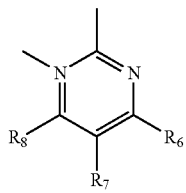
-continued
Pz:
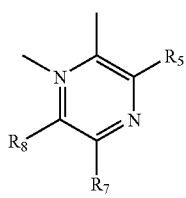
Qn3:
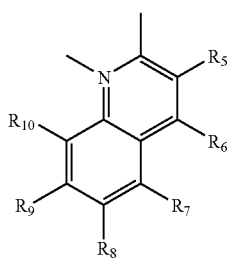
Xa:
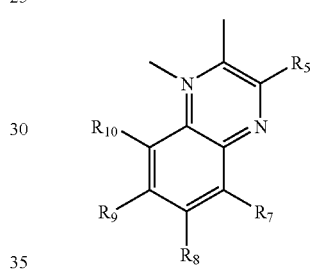
Bz:
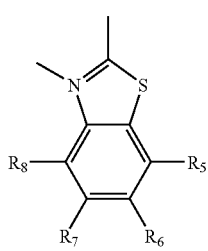
Bo:
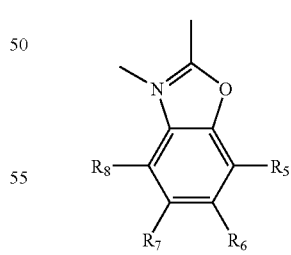
Oz:
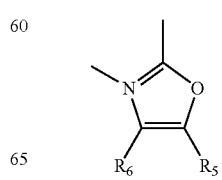

Sz: 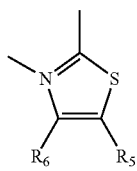
TABLE 1
| No | M | m | n | A | B | R1 | R2 | R3 | R4 | R5 | R6 | R7 | R8 | R9 | R10 |
|---|---|---|---|---|---|---|---|---|---|---|---|---|---|---|---|
| 1 | Ir | 3 | 0 | Ph | Iq2 | H | H | H | H | H | H | H | H | H | H |
| 2 | Ir | 3 | 0 | Ph | Iq2 | H | Ph | H | H | H | H | H | H | H | H |
| 3 | Ir | 3 | 0 | Ph | Iq2 | H | H | Ph | H | H | H | H | H | H | H |
| 4 | Ir | 3 | 0 | Ph | Iq2 | H | Ph | H | H | H | Ph | H | H | H | H |
| 5 | Ir | 3 | 0 | Ph | Iq2 | H | CH3 | H | H | H | H | CF3 | H | H | H |
| 6 | Ir | 3 | 0 | Ph | Iq2 | H | H | CH3 | H | H | CF3 | H | H | H | H |
| 7 | Ir | 3 | 0 | Ph | Iq2 | H | Naphthyl | H | H | H | H | H | H | H | H |
| 8 | Ir | 3 | 0 | Ph | Iq2 | H | H | Naphthyl | H | H | H | H | H | H | H |
| 9 | Ir | 3 | 0 | Ph | Iq2 | H | 4-Ph-naphthyl | H | H | H | H | H | H | H | H |
| 10 | Ir | 3 | 0 | Ph | Iq2 | H | H | 4-Ph-naphthyl | H | H | H | H | H | H | H |
TABLE 2
| No | M | m | n | A | B | R1 | R2 | R3 | R4 | R5 | R6 | R7 | R8 | R9 | R10 |
|---|---|---|---|---|---|---|---|---|---|---|---|---|---|---|---|
| 11 | Ir | 3 | 0 | Ph | Iq2 | H | CF3 | H | H | H | H | H | H | H | H |
| 12 | Ir | 3 | 0 | Ph | Iq2 | H | H | CF3 | H | H | H | H | H | H | H |

TABLE 2-continued

| | | | | | | A | | | | B | | | | | | |
|---|---|---|---|---|---|---|---|---|---|---|---|---|---|---|---|---|
| No | M | m | n | A | B | R1 | R2 | R3 | R4 | R5 | R6 | R7 | R8 | R9 | R10 |
| 13 | Ir | 3 | 0 | Ph | Iq2 | H | (9,9-dimethyl-fluorenyl with methyl) | H | H | H | H | H | H | H | H |
| 14 | Ir | 3 | 0 | Ph | Iq2 | H | H | (9,9-dimethyl-fluorenyl with methyl) | H | H | H | H | H | H | H |
| 15 | Ir | 3 | 0 | Ph | Iq2 | H | (phenyl-9,9-dimethylfluorenyl-methyl) | H | H | H | H | H | H | H | H |
| 16 | Ir | 3 | 0 | Ph | Iq2 | H | (2-methylnaphthyl) | H | H | H | H | H | H | H | H |
| 17 | Ir | 3 | 0 | Ph | Iq2 | H | OCH3 | H | H | H | H | H | H | H | H |
| 18 | Ir | 3 | 0 | Ph | Iq2 | H | (1-methylnaphthyl) | H | H | H | Ph | H | H | H | H |

TABLE 3

| | | | | | | | | | | | | A | | | |
|---|---|---|---|---|---|---|---|---|---|---|---|---|---|---|---|
| No | M | m | n | A | B | A' | B' | E | G | J | R1 | R2 | R3 | R4 |
| 19 | Ir | 3 | 0 | Ph | Iq2 | — | — | — | — | — | H | CH3 | H | H |
| 20 | Ir | 3 | 0 | Ph | Iq2 | — | — | — | — | — | H | H | CH3 | H |
| 21 | Ir | 3 | 0 | Ph | Iq2 | — | — | — | — | — | H | CH3 | CH3 | H |
| 22 | Ir | 3 | 0 | Ph | Iq2 | — | — | — | — | — | H | F | H | H |
| 23 | Ir | 3 | 0 | Ph | Iq2 | — | — | — | — | — | H | H | F | H |
| 24 | Ir | 3 | 0 | Tn1 | Iq2 | — | — | — | — | — | H | H | — | — |
| 25 | Ir | 3 | 0 | Tn3 | Iq2 | — | — | — | — | — | H | H | — | — |
| 26 | Ir | 3 | 0 | Tn4 | Iq2 | — | — | — | — | — | H | H | — | — |
| 27 | Ir | 3 | 0 | Np2 | Iq2 | — | — | — | — | — | H | H | — | — |
| 28 | Ir | 3 | 0 | Fl | Iq2 | — | — | — | — | — | H | H | — | — |
| 29 | Ir | 3 | 0 | Ph | Iq5 | — | — | — | — | — | H | H | H | H |
| 30 | Ir | 3 | 0 | Fl | Iq5 | — | — | — | — | — | H | H | H | H |
| 31 | Ir | 2 | 1 | Ph | Iq2 | Ph | Pr | — | — | — | H | H | H | H |
| 32 | Ir | 2 | 1 | Ph | Iq2 | Ph | Pr | — | — | — | H | CH3 | H | H |
| 33 | Ir | 2 | 1 | Ph | Iq2 | Ph | Pr | — | — | — | H | H | CH3 | H |
| 34 | Ir | 2 | 1 | Ph | Iq2 | Ph | Pr | — | — | — | H | CH3 | CH3 | H |
| 35 | Ir | 2 | 1 | Ph | Iq2 | Ph | Pr | — | — | — | H | F | H | H |
| 36 | Ir | 2 | 1 | Ph | Iq2 | Ph | Pr | — | — | — | H | H | F | H |
| 37 | Ir | 2 | 1 | Tn1 | Iq2 | Ph | Pr | — | — | — | H | H | — | — |
| 38 | Ir | 2 | 1 | Tn3 | Iq2 | Ph | Pr | — | — | — | H | H | — | — |
| 39 | Ir | 2 | 1 | Tn4 | Iq2 | Ph | Pr | — | — | — | H | H | — | — |
| 40 | Ir | 2 | 1 | Np2 | Iq2 | Ph | Pr | — | — | — | H | H | — | — |
| 41 | Ir | 2 | 1 | Fl | Iq2 | Ph | Pr | — | — | — | H | H | — | — |
| 42 | Ir | 2 | 1 | Ph | Iq2 | — | — | CH3 | CH3 | H | H | H | H | H |
| 43 | Ir | 2 | 1 | Ph | Iq2 | — | — | CH3 | CH3 | H | H | CH3 | H | H |
| 44 | Ir | 2 | 1 | Ph | Iq2 | — | — | CH3 | CH3 | H | H | H | CH3 | H |
| 45 | Ir | 2 | 1 | Ph | Iq2 | — | — | CH3 | CH3 | H | H | CH3 | CH3 | H |
| 46 | Ir | 2 | 1 | Ph | Iq2 | — | — | CH3 | CH3 | H | H | F | H | H |
| 47 | Ir | 2 | 1 | Ph | Iq2 | — | — | CH3 | CH3 | H | H | H | F | H |
| 48 | Ir | 2 | 1 | Tn1 | Iq2 | — | — | CH3 | CH3 | H | H | H | — | — |
| 49 | Ir | 2 | 1 | Tn3 | Iq2 | — | — | CH3 | CH3 | H | H | H | — | — |
| 50 | Ir | 2 | 1 | Tn4 | Iq2 | — | — | CH3 | CH3 | H | H | H | — | — |
| 51 | Ir | 2 | 1 | Np2 | Iq2 | — | — | CH3 | CH3 | H | H | H | — | — |

TABLE 3-continued

| No | M | m | n | A | B | A' | B' | E | G | J | R1 | R2 | R3 | R4 |
|---|---|---|---|---|---|---|---|---|---|---|---|---|---|---|
| 52 | Ir | 2 | 1 | Fl | Iq2 | — | — | CH3 | CH3 | H | H | H | — | — |
| 53 | Ir | 2 | 1 | Ph | Iq2 | — | — | CF3 | CF3 | H | H | H | H | H |
| 54 | Ir | 2 | 1 | Ph | Iq2 | — | — | CF3 | CF3 | H | H | CH3 | H | H |
| 55 | Ir | 2 | 1 | Ph | Iq2 | — | — | CF3 | CF3 | H | H | H | CH3 | H |
| 56 | Ir | 2 | 1 | Ph | Iq2 | — | — | CF3 | CF3 | H | H | CH3 | CH3 | H |
| 57 | Ir | 2 | 1 | Ph | Iq2 | — | — | CF3 | CF3 | H | H | F | H | H |
| 58 | Ir | 2 | 1 | Ph | Iq2 | — | — | CF3 | CF3 | H | H | H | F | H |
| 59 | Ir | 2 | 1 | Tn1 | Iq2 | — | — | CF3 | CF3 | H | H | H | — | — |
| 60 | Ir | 2 | 1 | Tn3 | Iq2 | — | — | CF3 | CF3 | H | H | H | — | — |

| | A' | | | | B | | | | | | B' | | | |
|---|---|---|---|---|---|---|---|---|---|---|---|---|---|---|
| No | R1 | R2 | R3 | R4 | R5 | R6 | R7 | R8 | R9 | R10 | R5 | R6 | R7 | R8 |
| 19 | — | — | — | — | H | H | H | H | H | H | — | — | — | — |
| 20 | — | — | — | — | H | H | H | H | H | H | — | — | — | — |
| 21 | — | — | — | — | H | H | H | H | H | H | — | — | — | — |
| 22 | — | — | — | — | H | H | H | H | H | H | — | — | — | — |
| 23 | — | — | — | — | H | H | H | H | H | H | — | — | — | — |
| 24 | — | — | — | — | H | H | H | H | H | H | — | — | — | — |
| 25 | — | — | — | — | H | H | H | H | H | H | — | — | — | — |
| 26 | — | — | — | — | H | H | H | H | H | H | — | — | — | — |
| 27 | — | — | — | — | H | H | H | H | H | H | — | — | — | — |
| 28 | — | — | — | — | H | H | H | H | H | H | — | — | — | — |
| 29 | — | — | — | — | H | H | H | H | H | H | — | — | — | — |
| 30 | — | — | — | — | H | H | H | H | H | H | — | — | — | — |
| 31 | H | H | H | H | H | H | H | H | H | H | H | H | H | H |
| 32 | H | H | H | H | H | H | H | H | H | H | H | H | H | H |
| 33 | H | H | H | H | H | H | H | H | H | H | H | H | H | H |
| 34 | H | H | H | H | H | H | H | H | H | H | H | H | H | H |
| 35 | H | H | H | H | H | H | H | H | H | H | H | H | H | H |
| 36 | H | H | H | H | H | H | H | H | H | H | H | H | H | H |
| 37 | H | H | H | H | H | H | H | H | H | H | H | H | H | H |
| 38 | H | H | H | H | H | H | H | H | H | H | H | H | H | H |
| 39 | H | H | H | H | H | H | H | H | H | H | H | H | H | H |
| 40 | H | H | H | H | H | H | H | H | H | H | H | H | H | H |
| 41 | H | H | H | H | H | H | H | H | H | H | H | H | H | H |
| 42 | — | — | — | — | H | H | H | H | H | H | — | — | — | — |
| 43 | — | — | — | — | H | H | H | H | H | H | — | — | — | — |
| 44 | — | — | — | — | H | H | H | H | H | H | — | — | — | — |
| 45 | — | — | — | — | H | H | H | H | H | H | — | — | — | — |
| 46 | — | — | — | — | H | H | H | H | H | H | — | — | — | — |
| 47 | — | — | — | — | H | H | H | H | H | H | — | — | — | — |
| 48 | — | — | — | — | H | H | H | H | H | H | — | — | — | — |
| 49 | — | — | — | — | H | H | H | H | H | H | — | — | — | — |
| 50 | — | — | — | — | H | H | H | H | H | H | — | — | — | — |
| 51 | — | — | — | — | H | H | H | H | H | H | — | — | — | — |
| 52 | — | — | — | — | H | H | H | H | H | H | — | — | — | — |
| 53 | — | — | — | — | H | H | H | H | H | H | — | — | — | — |
| 54 | — | — | — | — | H | H | H | H | H | H | — | — | — | — |
| 55 | — | — | — | — | H | H | H | H | H | H | — | — | — | — |
| 56 | — | — | — | — | H | H | H | H | H | H | — | — | — | — |
| 57 | — | — | — | — | H | H | H | H | H | H | — | — | — | — |
| 58 | — | — | — | — | H | H | H | H | H | H | — | — | — | — |
| 59 | — | — | — | — | H | H | H | H | H | H | — | — | — | — |
| 60 | — | — | — | — | H | H | H | H | H | H | — | — | — | — |

TABLE 4

| | | | | | | | | | | | A | | | | A' | | | |
|---|---|---|---|---|---|---|---|---|---|---|---|---|---|---|---|---|---|---|
| No | M | m | n | A | B | A' | B' | E | G | J | R1 | R2 | R3 | R4 | R1 | R2 | R3 | R4 |
| 61 | Ir | 2 | 1 | Tn4 | Iq2 | — | — | CF3 | CF3 | H | H | H | — | — | — | — | — | — |
| 62 | Ir | 2 | 1 | Np2 | Iq2 | — | — | CF3 | CF3 | H | H | H | — | — | — | — | — | — |
| 63 | Ir | 2 | 1 | Fl | Iq2 | — | — | CF3 | CF3 | H | H | H | — | — | — | — | — | — |
| 64 | Ir | 1 | 2 | Ph | Iq2 | Ph | Pr | — | — | — | H | H | H | H | H | H | H | H |
| 65 | Ir | 1 | 2 | Ph | Iq2 | Ph | Pr | — | — | — | H | CH3 | H | H | H | H | H | H |
| 66 | Ir | 1 | 2 | Ph | Iq2 | Ph | Pr | — | — | — | H | H | CH3 | H | H | H | H | H |
| 67 | Ir | 1 | 2 | Ph | Iq2 | Ph | Pr | — | — | — | H | CH3 | CH3 | H | H | H | H | H |
| 68 | Ir | 1 | 2 | Ph | Iq2 | Ph | Pr | — | — | — | H | F | H | H | H | H | H | H |
| 69 | Ir | 1 | 2 | Ph | Iq2 | Ph | Pr | — | — | — | H | H | F | H | H | H | H | H |
| 70 | Ir | 1 | 2 | Tn1 | Iq2 | Ph | Pr | — | — | — | H | H | — | — | H | H | H | H |
| 71 | Ir | 1 | 2 | Tn3 | Iq2 | Ph | Pr | — | — | — | H | H | — | — | H | H | H | H |
| 72 | Ir | 1 | 2 | Tn4 | Iq2 | Ph | Pr | — | — | — | H | H | — | — | H | H | H | H |
| 73 | Ir | 1 | 2 | Np2 | Iq2 | Ph | Pr | — | — | — | H | H | — | — | H | H | H | H |

TABLE 4-continued

| No | | | | | | | | | | | R1 | R2 | R3 | R4 | | | | |
|---|---|---|---|---|---|---|---|---|---|---|---|---|---|---|---|---|---|---|
| 74 | Ir | 1 | 2 | Fl | Iq2 | Ph | Pr | — | — | — | H | H | — | — | H | H | H | H |
| 75 | Ir | 1 | 2 | Ph | Iq2 | — | — | CH3 | CH3 | H | H | H | H | H | — | — | — | — |
| 76 | Ir | 1 | 2 | Ph | Iq2 | — | — | CH3 | CH3 | H | H | CH3 | H | H | — | — | — | — |
| 77 | Ir | 1 | 2 | Ph | Iq2 | — | — | CH3 | CH3 | H | H | H | CH3 | H | — | — | — | — |
| 78 | Ir | 1 | 2 | Ph | Iq2 | — | — | CH3 | CH3 | H | H | CH3 | CH3 | H | — | — | — | — |
| 79 | Ir | 1 | 2 | Ph | Iq2 | — | — | CH3 | CH3 | H | H | F | H | H | — | — | — | — |
| 80 | Ir | 1 | 2 | Ph | Iq2 | — | — | CH3 | CH3 | H | H | H | F | H | — | — | — | — |
| 81 | Ir | 3 | 0 | Ph | Iq2 | — | — | — | — | — | H | H | H | H | — | — | — | — |
| 82 | Ir | 3 | 0 | Ph | Iq2 | — | — | — | — | — | H | H | H | H | — | — | — | — |
| 83 | Ir | 3 | 0 | Ph | Iq2 | — | — | — | — | — | H | H | H | H | — | — | — | — |
| 84 | Ir | 3 | 0 | Ph | Iq2 | — | — | — | — | — | H | H | F | H | — | — | — | — |
| 85 | Ir | 3 | 0 | Ph | Iq2 | — | — | — | — | — | H | H | F | H | — | — | — | — |
| 86 | Rh | 3 | 0 | Ph | Iq2 | — | — | — | — | — | H | H | H | H | — | — | — | — |
| 87 | Rh | 3 | 0 | Tn1 | Iq2 | — | — | — | — | — | H | H | — | — | — | — | — | — |
| 88 | Rh | 3 | 0 | Tn3 | Iq2 | — | — | — | — | — | H | H | — | — | — | — | — | — |
| 89 | Rh | 3 | 0 | Np2 | Iq2 | — | — | — | — | — | H | H | — | — | — | — | — | — |
| 90 | Rh | 3 | 0 | Fl | Iq2 | — | — | — | — | — | H | H | — | — | — | — | — | — |
| 91 | Rh | 2 | 1 | Ph | Iq2 | Ph | Pr | — | — | — | H | H | H | H | H | H | H | H |
| 92 | Rh | 2 | 1 | Ph | Iq2 | Ph | Pr | — | — | — | H | CH3 | H | H | H | H | H | H |
| 93 | Rh | 2 | 1 | Ph | Iq2 | Ph | Pr | — | — | — | H | H | CH3 | H | H | H | H | H |
| 94 | Rh | 2 | 1 | Ph | Iq2 | — | — | CH3 | CH3 | H | H | H | H | H | — | — | — | — |
| 95 | Pt | 2 | 0 | Ph | Iq2 | — | — | — | — | — | H | H | H | H | — | — | — | — |
| 96 | Pt | 2 | 0 | Ph | Iq2 | — | — | — | — | — | H | CH3 | H | H | — | — | — | — |
| 97 | Pt | 2 | 0 | Ph | Iq2 | — | — | — | — | — | H | CH3 | CH3 | H | — | — | — | — |
| 98 | Pt | 2 | 0 | Ph | Iq2 | — | — | — | — | — | H | F | H | H | — | — | — | — |
| 99 | Pt | 2 | 0 | Ph | Iq2 | — | — | — | — | — | H | H | F | H | — | — | — | — |
| 100 | Pt | 2 | 0 | Tn1 | Iq2 | — | — | — | — | — | H | H | — | — | — | — | — | — |

| | B | | | | | | B' | | | |
|---|---|---|---|---|---|---|---|---|---|---|
| No | R5 | R6 | R7 | R8 | R9 | R10 | R5 | R6 | R7 | R8 |
| 61 | H | H | H | H | H | H | — | — | — | — |
| 62 | H | H | H | H | H | H | — | — | — | — |
| 63 | H | H | H | H | H | H | — | — | — | — |
| 64 | H | H | H | H | H | H | H | H | H | H |
| 65 | H | H | H | H | H | H | H | H | H | H |
| 66 | H | H | H | H | H | H | H | H | H | H |
| 67 | H | H | H | H | H | H | H | H | H | H |
| 68 | H | H | H | H | H | H | H | H | H | H |
| 69 | H | H | H | H | H | H | H | H | H | H |
| 70 | H | H | H | H | H | H | H | H | H | H |
| 71 | H | H | H | H | H | H | H | H | H | H |
| 72 | H | H | H | H | H | H | H | H | H | H |
| 73 | H | H | H | H | H | H | H | H | H | H |
| 74 | H | H | H | H | H | H | H | H | H | H |
| 75 | H | H | H | H | H | H | — | — | — | — |
| 76 | H | H | H | H | H | H | — | — | — | — |
| 77 | H | H | H | H | H | H | — | — | — | — |
| 78 | H | H | H | H | H | H | — | — | — | — |
| 79 | H | H | H | H | H | H | — | — | — | — |
| 80 | H | H | H | H | H | H | — | — | — | — |
| 81 | H | H | H | H | F | H | — | — | — | — |
| 82 | H | H | H | H | CF3 | H | — | — | — | — |
| 83 | H | H | H | CF3 | H | H | — | — | — | — |
| 84 | H | H | H | F | H | H | — | — | — | — |
| 85 | H | H | H | CF3 | H | H | — | — | — | — |
| 86 | H | H | H | H | H | H | — | — | — | — |
| 87 | H | H | H | H | H | H | — | — | — | — |
| 88 | H | H | H | H | H | H | — | — | — | — |
| 89 | H | H | H | H | H | H | — | — | — | — |
| 90 | H | H | H | H | H | H | — | — | — | — |
| 91 | H | H | H | H | H | H | H | H | H | H |
| 92 | H | H | H | H | H | H | H | H | H | H |
| 93 | H | H | H | H | H | H | H | H | H | H |
| 94 | H | H | H | H | H | H | — | — | — | — |
| 95 | H | H | H | H | H | H | — | — | — | — |
| 96 | H | H | H | H | H | H | — | — | — | — |
| 97 | H | H | H | H | H | H | — | — | — | — |
| 98 | H | H | H | H | H | H | — | — | — | — |
| 99 | H | H | H | H | H | H | — | — | — | — |
| 100 | H | H | H | H | H | H | — | — | — | — |

TABLE 5

| No | M | m | n | A | B | A' | B' | E | G | J | A R1 | R2 | R3 | R4 |
|---|---|---|---|---|---|---|---|---|---|---|---|---|---|---|
| 101 | Pt | 2 | 0 | Tn3 | Iq2 | — | — | — | — | — | H | H | — | — |
| 102 | Pt | 1 | 1 | Ph | Iq2 | Ph | Pr | — | — | — | H | H | H | H |
| 103 | Pt | 1 | 1 | Ph | Iq2 | Ph | Pr | — | — | — | H | H | CH3 | H |
| 104 | Pt | 1 | 1 | Ph | Iq2 | Ph | Pr | — | — | — | H | CH3 | CH3 | H |
| 105 | Pt | 1 | 1 | Ph | Iq2 | Ph | Pr | — | — | — | H | F | H | H |
| 106 | Pd | 2 | 0 | Ph | Iq2 | — | — | — | — | — | H | H | H | H |
| 107 | Pd | 2 | 0 | Ph | Iq2 | — | — | — | — | — | H | H | CH3 | H |
| 108 | Pd | 2 | 0 | Tn1 | Iq2 | — | — | — | — | — | H | H | — | — |
| 109 | Pd | 2 | 0 | Tn3 | Iq2 | — | — | — | — | — | H | H | — | — |
| 110 | Pd | 1 | 1 | Ph | Iq2 | Ph | Pr | — | — | — | H | H | H | H |
| 111 | Ir | 2 | 1 | Ph | Iq2 | — | — | CH3 | CH3 | CH3 | H | H | H | H |
| 112 | Ir | 2 | 1 | Ph | Iq2 | — | — | C(CH3)3 | C(CH3)3 | H | H | H | H | H |
| 113 | Ir | 2 | 1 | Ph | Iq2 | — | — | CH3 | C4H9 | CH3 | H | H | H | H |
| 114 | Ir | 2 | 1 | Tn1 | Iq2 | — | — | CH3 | CH3 | CH3 | H | H | — | — |
| 115 | Ir | 2 | 1 | Tn1 | Iq2 | — | — | C(CH3)3 | C(CH3)3 | H | H | H | — | — |
| 116 | Ir | 2 | 1 | Tn1 | Iq2 | — | — | CH3 | C3H7 | CH3 | H | H | — | — |
| 117 | Ir | 2 | 1 | Tn2 | Iq2 | — | — | CH3 | CH3 | CH3 | H | H | — | — |
| 118 | Ir | 2 | 1 | Tn2 | Iq2 | — | — | C(CH3)3 | C(CH3)3 | H | H | H | — | — |
| 119 | Ir | 2 | 1 | Tn2 | Iq2 | — | — | CH3 | C6H13 | CH3 | H | H | — | — |
| 120 | Ir | 2 | 1 | Tn3 | Iq2 | — | — | CH3 | CH3 | CH3 | H | H | — | — |
| 121 | Ir | 2 | 1 | Tn3 | Iq2 | — | — | C(CH3)3 | C(CH3)3 | H | H | H | — | — |
| 122 | Ir | 2 | 1 | Tn3 | Iq2 | — | — | CH3 | C4H9 | CH3 | H | H | — | — |
| 123 | Ir | 2 | 1 | Tn4 | Iq2 | — | — | CH3 | CH3 | CH3 | H | H | — | — |
| 124 | Ir | 2 | 1 | Tn4 | Iq2 | — | — | C(CH3)3 | C(CH3)3 | H | H | H | — | — |
| 125 | Ir | 2 | 1 | Tn4 | Iq2 | — | — | CH3 | C5H11 | CH3 | H | H | — | — |
| 126 | Ir | 2 | 1 | Ph | Iq2 | — | — | CH3 | CH3 | CH3 | H | CH3 | H | H |
| 127 | Ir | 2 | 1 | Ph | Iq2 | — | — | C(CH3)3 | C(CH3)3 | H | H | CH3 | H | H |
| 128 | Ir | 2 | 1 | Ph | Iq2 | — | — | CH3 | C4H9 | CH3 | H | CH3 | H | H |
| 129 | Ir | 2 | 1 | Fl | Iq2 | — | — | CH3 | CH3 | CH3 | H | H | — | — |
| 130 | Ir | 2 | 1 | Fl | Iq2 | — | — | C(CH3)3 | C(CH3)3 | H | H | H | — | — |
| 131 | Ir | 2 | 1 | Fl | Iq2 | — | — | CH3 | C4H9 | CH3 | H | H | — | — |
| 132 | Ir | 2 | 1 | Np1 | Iq2 | — | — | CH3 | CH3 | CH3 | H | H | — | — |
| 133 | Ir | 2 | 1 | Np1 | Iq2 | — | — | C(CH3)3 | C(CH3)3 | H | H | H | — | — |
| 134 | Ir | 2 | 1 | Np1 | Iq2 | — | — | CH3 | C4H9 | CH3 | H | H | — | — |
| 135 | Ir | 3 | 0 | Ph | Iq2 | — | — | — | — | — | H | C2H5 | H | H |
| 136 | Ir | 2 | 1 | Ph | Iq2 | Ph | Pr | — | — | — | H | C2H5 | H | H |
| 137 | Ir | 2 | 1 | Ph | Iq2 | — | — | CH3 | CH3 | CH3 | H | C2H5 | H | H |
| 138 | Ir | 2 | 1 | Ph | Iq2 | — | — | CH3 | CH3 | CH3 | H | C2H5 | H | H |
| 139 | Ir | 2 | 1 | Ph | Iq2 | — | — | C(CH3)3 | C(CH3)3 | H | H | C2H5 | H | H |
| 140 | Ir | 2 | 1 | Ph | Iq2 | — | — | CH3 | C4H9 | CH3 | H | C2H5 | H | H |

| No | A' R1 | R2 | R3 | R4 | B R5 | R6 | R7 | R8 | R9 | R10 | B' R5 | R6 | R7 | R8 |
|---|---|---|---|---|---|---|---|---|---|---|---|---|---|---|
| 101 | — | — | — | — | H | H | H | H | H | H | — | — | — | — |
| 102 | H | H | H | H | H | H | H | H | H | H | H | H | H | H |
| 103 | H | H | H | H | H | H | H | H | H | H | H | H | H | H |
| 104 | H | H | H | H | H | H | H | H | H | H | H | H | H | H |
| 105 | H | H | H | H | H | H | H | H | H | H | H | H | H | H |
| 106 | — | — | — | — | H | H | H | H | H | H | — | — | — | — |
| 107 | — | — | — | — | H | H | H | H | H | H | — | — | — | — |
| 108 | — | — | — | — | H | H | H | H | H | H | — | — | — | — |
| 109 | — | — | — | — | H | H | H | H | H | H | — | — | — | — |
| 110 | H | H | H | H | H | H | H | H | H | H | H | H | H | H |
| 111 | — | — | — | — | H | H | H | H | H | H | — | — | — | — |
| 112 | — | — | — | — | H | H | H | H | H | H | — | — | — | — |
| 113 | — | — | — | — | H | H | H | H | H | H | — | — | — | — |
| 114 | — | — | — | — | H | H | H | H | H | H | — | — | — | — |
| 115 | — | — | — | — | H | H | H | H | H | H | — | — | — | — |
| 116 | — | — | — | — | H | H | H | H | H | H | — | — | — | — |
| 117 | — | — | — | — | H | H | H | H | H | H | — | — | — | — |
| 118 | — | — | — | — | H | H | H | H | H | H | — | — | — | — |
| 119 | — | — | — | — | H | H | H | H | H | H | — | — | — | — |
| 120 | — | — | — | — | H | H | H | H | H | H | — | — | — | — |
| 121 | — | — | — | — | H | H | H | H | H | H | — | — | — | — |
| 122 | — | — | — | — | H | H | H | H | H | H | — | — | — | — |
| 123 | — | — | — | — | H | H | H | H | H | H | — | — | — | — |
| 124 | — | — | — | — | H | H | H | H | H | H | — | — | — | — |
| 125 | — | — | — | — | H | H | H | H | H | H | — | — | — | — |
| 126 | — | — | — | — | H | H | H | H | H | H | — | — | — | — |
| 127 | — | — | — | — | H | H | H | H | H | H | — | — | — | — |
| 128 | — | — | — | — | H | H | H | H | H | H | — | — | — | — |
| 129 | — | — | — | — | H | H | H | H | H | H | — | — | — | — |
| 130 | — | — | — | — | H | H | H | H | H | H | — | — | — | — |

TABLE 5-continued

| | | | | | | | | | | | | | | | |
|---|---|---|---|---|---|---|---|---|---|---|---|---|---|---|---|
| 131 | — | — | — | — | H | H | H | H | H | H | — | — | — | — |
| 132 | — | — | — | — | H | H | H | H | H | H | — | — | — | — |
| 133 | — | — | — | — | H | H | H | H | H | H | — | — | — | — |
| 134 | — | — | — | — | H | H | H | H | H | H | — | — | — | — |
| 135 | — | — | — | — | H | H | H | H | H | H | — | — | — | — |
| 136 | H | H | H | H | H | H | H | H | H | H | H | H | H | H |
| 137 | — | — | — | — | H | H | H | H | H | H | — | — | — | — |
| 138 | — | — | — | — | H | H | H | H | H | H | — | — | — | — |
| 139 | — | — | — | — | H | H | H | H | H | H | — | — | — | — |
| 140 | — | — | — | — | H | H | H | H | H | H | — | — | — | — |

TABLE 6

| No | M | m | n | A | B | A' | B' | E | G | J | B" | A R1 | A R2 | A R3 | A R4 | A' R1 | A' R2 | A' R3 | A' R4 |
|---|---|---|---|---|---|---|---|---|---|---|---|---|---|---|---|---|---|---|---|
| 141 | Ir | 2 | 1 | Ph | Iq2 | — | — | — | — | — | Pr | H | C2H5 | H | H | — | — | — | — |
| 142 | Ir | 2 | 1 | Ph | Iq2 | — | — | — | — | — | Pr | H | C2H5 | H | H | — | — | — | — |
| 143 | Ir | 2 | 1 | Ph | Iq2 | — | — | — | — | — | Iq2 | H | C2H5 | H | H | — | — | — | — |
| 144 | Ir | 3 | 0 | Ph | Iq2 | — | — | — | — | — | — | H | C3H7 | H | H | — | — | — | — |
| 145 | Ir | 3 | 0 | Ph | Iq2 | — | — | — | — | — | — | H | C3H7 | H | H | — | — | — | — |
| 146 | Ir | 3 | 0 | Ph | Iq2 | — | — | — | — | — | — | H | CH(CH3)2 | H | H | — | — | — | — |
| 147 | Ir | 2 | 1 | Ph | Iq2 | Ph | Pr | — | — | — | — | H | C3H7 | H | H | H | H | H | H |
| 148 | Ir | 2 | 1 | Ph | Iq2 | — | — | CH3 | CH3 | H | — | H | C3H7 | H | H | — | — | — | — |
| 149 | Ir | 2 | 1 | Ph | Iq2 | — | — | CH3 | CH3 | CH3 | — | H | C3H7 | H | H | — | — | — | — |
| 150 | Ir | 2 | 1 | Ph | Iq2 | — | — | C(CH3)3 | C(CH3)3 | H | — | H | C3H7 | H | H | — | — | — | — |
| 151 | Ir | 2 | 1 | Ph | Iq2 | — | — | CH3 | C4H9 | CH3 | — | H | C3H7 | H | H | — | — | — | — |
| 152 | Ir | 2 | 1 | Ph | Iq2 | — | — | — | — | — | Pr | H | C3H7 | H | H | — | — | — | — |
| 153 | Ir | 2 | 1 | Ph | Iq2 | — | — | — | — | — | Pr | H | C3H7 | H | H | — | — | — | — |
| 154 | Ir | 2 | 1 | Ph | Iq2 | — | — | — | — | — | Iq2 | H | C3H7 | H | H | — | — | — | — |
| 155 | Ir | 3 | 0 | Ph | Iq2 | — | — | — | — | — | — | H | H | H | H | — | — | — | — |
| 156 | Ir | 3 | 0 | Ph | Iq2 | — | — | — | — | — | — | H | H | H | H | — | — | — | — |
| 157 | Ir | 3 | 0 | Ph | Iq2 | — | — | — | — | — | — | H | CH3 | H | H | — | — | — | — |
| 158 | Ir | 3 | 0 | Ph | Iq2 | — | — | — | — | — | — | H | CH3 | H | H | — | — | — | — |
| 159 | Ir | 3 | 0 | Ph | Iq2 | — | — | — | — | — | — | H | C4H9 | H | H | — | — | — | — |
| 160 | Ir | 3 | 0 | Ph | Iq2 | — | — | — | — | — | — | H | C4H9 | H | H | — | — | — | — |
| 161 | Ir | 3 | 0 | Ph | Iq2 | — | — | — | — | — | — | H | C4H9 | H | H | — | — | — | — |
| 162 | Ir | 2 | 1 | Ph | Iq2 | Ph | Pr | — | — | — | — | H | C4H9 | H | H | H | H | H | H |
| 163 | Ir | 2 | 1 | Ph | Iq2 | — | — | CH3 | CH3 | H | — | H | C4H9 | H | H | — | — | — | — |
| 164 | Ir | 2 | 1 | Ph | Iq2 | — | — | CH3 | CH3 | CH3 | — | H | C4H9 | H | H | — | — | — | — |
| 165 | Ir | 2 | 1 | Ph | Iq2 | — | — | C(CH3)3 | C(CH3)3 | H | — | H | C4H9 | H | H | — | — | — | — |
| 166 | Ir | 2 | 1 | Ph | Iq2 | — | — | CH3 | C4H9 | CH3 | — | H | C4H9 | H | H | — | — | — | — |
| 167 | Ir | 2 | 1 | Ph | Iq2 | — | — | — | — | — | Pr | H | C4H9 | H | H | — | — | — | — |
| 168 | Ir | 2 | 1 | Ph | Iq2 | — | — | — | — | — | Pr | H | C4H9 | H | H | — | — | — | — |
| 169 | Ir | 2 | 1 | Ph | Iq2 | — | — | — | — | — | Iq2 | H | C4H9 | H | H | — | — | — | — |
| 170 | Ir | 3 | 0 | Ph | Iq2 | — | — | — | — | — | — | H | C(CH3)3 | H | H | — | — | — | — |
| 171 | Ir | 3 | 0 | Ph | Iq2 | — | — | — | — | — | — | H | C(CH3)3 | H | H | — | — | — | — |
| 172 | Ir | 3 | 0 | Ph | Iq2 | — | — | — | — | — | — | H | C(CH3)3 | H | H | — | — | — | — |
| 173 | Ir | 2 | 1 | Ph | Iq2 | Ph | Pr | — | — | — | — | H | C(CH3)3 | H | H | H | H | H | H |
| 174 | Ir | 2 | 1 | Ph | Iq2 | — | — | CH3 | CH3 | H | — | H | C(CH3)3 | H | H | — | — | — | — |
| 175 | Ir | 2 | 1 | Ph | Iq2 | — | — | CH3 | CH3 | CH3 | — | H | C(CH3)3 | H | H | — | — | — | — |
| 176 | Ir | 2 | 1 | Ph | Iq2 | — | — | C(CH3)3 | C(CH3)3 | H | — | H | C(CH3)3 | H | H | — | — | — | — |
| 177 | Ir | 2 | 1 | Ph | Iq2 | — | — | CH3 | C4H9 | CH3 | — | H | C(CH3)3 | H | H | — | — | — | — |
| 178 | Ir | 2 | 1 | Ph | Iq2 | — | — | — | — | — | Pr | H | C(CH3)3 | H | H | — | — | — | — |
| 179 | Ir | 2 | 1 | Ph | Iq2 | — | — | — | — | — | Pr | H | C(CH3)3 | H | H | — | — | — | — |
| 180 | Ir | 2 | 1 | Ph | Iq2 | — | — | — | — | — | Iq2 | H | C(CH3)3 | H | H | — | — | — | — |

| No | B R5 | B R6 | B R7 | B R8 | B R9 | B R10 | B' R5 | B' R6 | B' R7 | B' R8 | B" R5 | B" R6 | B" R7 | B" R8 | B" R9 | B" R10 |
|---|---|---|---|---|---|---|---|---|---|---|---|---|---|---|---|---|
| 141 | H | H | H | H | H | H | — | — | — | — | H | H | H | H | — | — |
| 142 | H | H | H | H | H | H | — | — | — | — | H | H | C4H9 | H | — | — |
| 143 | H | H | H | H | H | H | — | — | — | — | H | H | H | H | H | H |
| 144 | H | H | H | H | H | H | — | — | — | — | — | — | — | — | — | — |
| 145 | H | H | H | F | H | H | — | — | — | — | — | — | — | — | — | — |
| 146 | H | H | H | H | H | H | — | — | — | — | — | — | — | — | — | — |
| 147 | H | H | H | H | H | H | H | H | H | — | — | — | — | — | — | — |
| 148 | H | H | H | H | H | H | — | — | — | — | — | — | — | — | — | — |
| 149 | H | H | H | H | H | H | — | — | — | — | — | — | — | — | — | — |
| 150 | H | H | H | H | H | H | — | — | — | — | — | — | — | — | — | — |
| 151 | H | H | H | H | H | H | — | — | — | — | — | — | — | — | — | — |
| 152 | H | H | H | H | H | H | — | — | — | — | H | H | H | H | — | — |
| 153 | H | H | H | H | H | H | — | — | — | — | H | H | C4H9 | H | — | — |
| 154 | H | H | H | H | H | H | — | — | — | — | H | H | H | H | H | H |

TABLE 6-continued

| No | A | B | A' | B' | E | G | J | B" | R1 | R2 | R3 | R4 | R1 | R2 | R3 | R4 |
|---|---|---|---|---|---|---|---|---|---|---|---|---|---|---|---|---|
| 155 | H | H | H | F | H | H | — | — | — | — | — | — | — | — | — | — |
| 156 | H | H | H | H | C6H13 | H | — | — | — | — | — | — | — | — | — | — |
| 157 | H | H | H | F | H | H | — | — | — | — | — | — | — | — | — | — |
| 158 | H | H | H | H | C6H13 | H | — | — | — | — | — | — | — | — | — | — |
| 159 | H | H | H | H | H | H | — | — | — | — | — | — | — | — | — | — |
| 160 | H | H | H | F | H | H | — | — | — | — | — | — | — | — | — | — |
| 161 | H | H | H | H | C6H13 | H | — | — | — | — | — | — | — | — | — | — |
| 162 | H | H | H | H | H | H | H | H | H | H | — | — | — | — | — | — |
| 163 | H | H | H | H | H | H | — | — | — | — | — | — | — | — | — | — |
| 164 | H | H | H | H | H | H | — | — | — | — | — | — | — | — | — | — |
| 165 | H | H | H | H | H | H | — | — | — | — | — | — | — | — | — | — |
| 166 | H | H | H | H | H | H | — | — | — | — | — | — | — | — | — | — |
| 167 | H | H | H | H | H | H | — | — | — | — | H | H | H | H | — | — |
| 168 | H | H | H | H | H | H | — | — | — | — | H | H | C4H9 | H | — | — |
| 169 | H | H | H | H | H | H | — | — | — | — | H | H | H | H | H | H |
| 170 | H | H | H | H | H | H | — | — | — | — | — | — | — | — | — | — |
| 171 | H | H | H | F | H | H | — | — | — | — | — | — | — | — | — | — |
| 172 | H | H | H | H | C6H13 | H | — | — | — | — | — | — | — | — | — | — |
| 173 | H | H | H | H | H | H | H | H | H | H | — | — | — | — | — | — |
| 174 | H | H | H | H | H | H | — | — | — | — | — | — | — | — | — | — |
| 175 | H | H | H | H | H | H | — | — | — | — | — | — | — | — | — | — |
| 176 | H | H | H | H | H | H | — | — | — | — | — | — | — | — | — | — |
| 177 | H | H | H | H | H | H | — | — | — | — | — | — | — | — | — | — |
| 178 | H | H | H | H | H | H | — | — | — | — | H | H | H | H | — | — |
| 179 | H | H | H | H | H | H | — | — | — | — | H | H | C4H9 | H | — | — |
| 180 | H | H | H | H | H | H | — | — | — | — | H | H | H | H | H | H |

TABLE 7

| No | M | m | n | A | B | A' | B' | E | G | J | B" | A R1 | A R2 | A R3 | A R4 | A' R1 | A' R2 | A' R3 | A' R4 |
|---|---|---|---|---|---|---|---|---|---|---|---|---|---|---|---|---|---|---|---|
| 181 | Ir | 3 | 0 | Ph | Iq2 | — | — | — | — | — | — | H | C5H11 | H | H | — | — | — | — |
| 182 | Ir | 3 | 0 | Ph | Iq2 | — | — | — | — | — | — | H | C5H11 | H | H | — | — | — | — |
| 183 | Ir | 3 | 0 | Ph | Iq2 | — | — | — | — | — | — | H | C5H11 | H | H | — | — | — | — |
| 184 | Ir | 2 | 1 | Ph | Iq2 | Ph | Pr | — | — | — | — | H | C5H11 | H | H | H | H | H | H |
| 185 | Ir | 2 | 1 | Ph | Iq2 | — | — | CH3 | CH3 | H | — | H | C5H11 | H | H | — | — | — | — |
| 186 | Ir | 2 | 1 | Ph | Iq2 | — | — | CH3 | CH3 | CH3 | — | H | C5H11 | H | H | — | — | — | — |
| 187 | Ir | 2 | 1 | Ph | Iq2 | — | — | C(CH3)3 | C(CH3)3 | H | — | H | C5H11 | H | H | — | — | — | — |
| 188 | Ir | 2 | 1 | Ph | Iq2 | — | — | CH3 | C4H9 | CH3 | — | H | C5H11 | H | H | — | — | — | — |
| 189 | Ir | 2 | 1 | Ph | Iq2 | — | — | — | — | — | Pr | H | C5H11 | H | H | — | — | — | — |
| 190 | Ir | 2 | 1 | Ph | Iq2 | — | — | — | — | — | Pr | H | C5H11 | H | H | — | — | — | — |
| 191 | Ir | 2 | 1 | Ph | Iq2 | — | — | — | — | — | Iq2 | H | C5H11 | H | H | — | — | — | — |
| 192 | Ir | 3 | 0 | Ph | Iq2 | — | — | — | — | — | — | H | C6H13 | H | H | — | — | — | — |
| 193 | Ir | 3 | 0 | Ph | Iq2 | — | — | — | — | — | — | H | C6H13 | H | H | — | — | — | — |
| 194 | Ir | 3 | 0 | Ph | Iq2 | — | — | — | — | — | — | H | C6H13 | H | H | — | — | — | — |
| 195 | Ir | 2 | 1 | Ph | Iq2 | Ph | Pr | — | — | — | — | H | C6H13 | H | H | H | H | H | H |
| 196 | Ir | 2 | 1 | Ph | Iq2 | — | — | CH3 | CH3 | H | — | H | C6H13 | H | H | — | — | — | — |
| 197 | Ir | 2 | 1 | Ph | Iq2 | — | — | CH3 | CH3 | CH3 | — | H | C6H13 | H | H | — | — | — | — |
| 198 | Ir | 2 | 1 | Ph | Iq2 | — | — | C(CH3)3 | C(CH3)3 | H | — | H | C6H13 | H | H | — | — | — | — |
| 199 | Ir | 2 | 1 | Ph | Iq2 | — | — | CH3 | C4H9 | CH3 | — | H | C6H13 | H | H | — | — | — | — |
| 200 | Ir | 2 | 1 | Ph | Iq2 | — | — | — | — | — | Pr | H | C6H13 | H | H | — | — | — | — |
| 201 | Ir | 2 | 1 | Ph | Iq2 | — | — | — | — | — | Pr | H | C6H13 | H | H | — | — | — | — |
| 202 | Ir | 2 | 1 | Ph | Iq2 | — | — | — | — | — | Iq2 | H | C6H13 | H | H | — | — | — | — |
| 203 | Ir | 3 | 0 | Ph | Iq2 | — | — | — | — | — | — | H | C7H15 | H | H | — | — | — | — |
| 204 | Ir | 3 | 0 | Ph | Iq2 | — | — | — | — | — | — | H | C7H15 | H | H | — | — | — | — |
| 205 | Ir | 3 | 0 | Ph | Iq2 | — | — | — | — | — | — | H | C7H15 | H | H | — | — | — | — |
| 206 | Ir | 2 | 1 | Ph | Iq2 | Ph | Pr | — | — | — | — | H | C7H15 | H | H | H | H | H | H |
| 207 | Ir | 2 | 1 | Ph | Iq2 | — | — | CH3 | CH3 | H | — | H | C7H15 | H | H | — | — | — | — |
| 208 | Ir | 2 | 1 | Ph | Iq2 | — | — | CH3 | CH3 | CH3 | — | H | C7H15 | H | H | — | — | — | — |
| 209 | Ir | 2 | 1 | Ph | Iq2 | — | — | C(CH3)3 | C(CH3)3 | H | — | H | C7H15 | H | H | — | — | — | — |
| 210 | Ir | 2 | 1 | Ph | Iq2 | — | — | CH3 | C4H9 | CH3 | — | H | C7H15 | H | H | — | — | — | — |
| 211 | Ir | 2 | 1 | Ph | Iq2 | — | — | — | — | — | Pr | H | C7H15 | H | H | — | — | — | — |
| 212 | Ir | 2 | 1 | Ph | Iq2 | — | — | — | — | — | Pr | H | C7H15 | H | H | — | — | — | — |
| 213 | Ir | 2 | 1 | Ph | Iq2 | — | — | — | — | — | Iq2 | H | C7H15 | H | H | — | — | — | — |
| 214 | Ir | 3 | 0 | Ph | Iq2 | — | — | — | — | — | — | H | C8H17 | H | H | — | — | — | — |
| 215 | Ir | 3 | 0 | Ph | Iq2 | — | — | — | — | — | — | H | C8H17 | H | H | — | — | — | — |
| 216 | Ir | 3 | 0 | Ph | Iq2 | — | — | — | — | — | — | H | C8H17 | H | H | — | — | — | — |
| 217 | Ir | 2 | 1 | Ph | Iq2 | Ph | Pr | — | — | — | — | H | C8H17 | H | H | H | H | H | H |
| 218 | Ir | 2 | 1 | Ph | Iq2 | — | — | CH3 | CH3 | H | — | H | C8H17 | H | H | — | — | — | — |
| 219 | Ir | 2 | 1 | Ph | Iq2 | — | — | CH3 | CH3 | CH3 | — | H | C8H17 | H | H | — | — | — | — |
| 220 | Ir | 3 | 0 | Ph | Iq2 | — | — | — | — | — | — | H | H | H | H | — | — | — | — |

TABLE 7-continued

| | | B | | | | | | B' | | | | B'' | | | | |
|---|---|---|---|---|---|---|---|---|---|---|---|---|---|---|---|---|
| No | R5 | R6 | R7 | R8 | R9 | R10 | R5 | R6 | R7 | R8 | R5 | R6 | R7 | R8 | R9 | R10 |
| 181 | H | H | H | H | H | H | — | — | — | — | — | — | — | — | — | — |
| 182 | H | H | H | F | H | H | — | — | — | — | — | — | — | — | — | — |
| 183 | H | H | H | H | C6H13 | H | — | — | — | — | — | — | — | — | — | — |
| 184 | H | H | H | H | H | H | H | H | H | H | — | — | — | — | — | — |
| 185 | H | H | H | H | H | H | — | — | — | — | — | — | — | — | — | — |
| 186 | H | H | H | H | H | H | — | — | — | — | — | — | — | — | — | — |
| 187 | H | H | H | H | H | H | — | — | — | — | — | — | — | — | — | — |
| 188 | H | H | H | H | H | H | — | — | — | — | — | — | — | — | — | — |
| 189 | H | H | H | H | H | H | — | — | — | — | H | H | H | H | — | — |
| 190 | H | H | H | H | H | H | — | — | — | — | H | H | C4H9 | H | — | — |
| 191 | H | H | H | H | H | H | — | — | — | — | H | H | H | H | H | H |
| 192 | H | H | H | H | H | H | — | — | — | — | — | — | — | — | — | — |
| 193 | H | H | H | F | H | H | — | — | — | — | — | — | — | — | — | — |
| 194 | H | H | H | H | C6H13 | H | — | — | — | — | — | — | — | — | — | — |
| 195 | H | H | H | H | H | H | H | H | H | H | — | — | — | — | — | — |
| 196 | H | H | H | H | H | H | — | — | — | — | — | — | — | — | — | — |
| 197 | H | H | H | H | H | H | — | — | — | — | — | — | — | — | — | — |
| 198 | H | H | H | H | H | H | — | — | — | — | — | — | — | — | — | — |
| 199 | H | H | H | H | H | H | — | — | — | — | — | — | — | — | — | — |
| 200 | H | H | H | H | H | H | — | — | — | — | H | H | H | H | — | — |
| 201 | H | H | H | H | H | H | — | — | — | — | H | H | C4H9 | H | — | — |
| 202 | H | H | H | H | H | H | — | — | — | — | H | H | H | H | H | H |
| 203 | H | H | H | H | H | H | — | — | — | — | — | — | — | — | — | — |
| 204 | H | H | H | F | H | H | — | — | — | — | — | — | — | — | — | — |
| 205 | H | H | H | H | C6H13 | H | — | — | — | — | — | — | — | — | — | — |
| 206 | H | H | H | H | H | H | H | H | H | H | — | — | — | — | — | — |
| 207 | H | H | H | H | H | H | — | — | — | — | — | — | — | — | — | — |
| 208 | H | H | H | H | H | H | — | — | — | — | — | — | — | — | — | — |
| 209 | H | H | H | H | H | H | — | — | — | — | — | — | — | — | — | — |
| 210 | H | H | H | H | H | H | — | — | — | — | — | — | — | — | — | — |
| 211 | H | H | H | H | H | H | — | — | — | — | H | H | H | H | — | — |
| 212 | H | H | H | H | H | H | — | — | — | — | H | H | C4H9 | H | — | — |
| 213 | H | H | H | H | H | H | — | — | — | — | H | H | H | H | H | H |
| 214 | H | H | H | H | H | H | — | — | — | — | — | — | — | — | — | — |
| 215 | H | H | H | F | H | H | — | — | — | — | — | — | — | — | — | — |
| 216 | H | H | H | H | C6H13 | H | — | — | — | — | — | — | — | — | — | — |
| 217 | H | H | H | H | H | H | H | H | H | H | — | — | — | — | — | — |
| 218 | H | H | H | H | H | H | — | — | — | — | — | — | — | — | — | — |
| 219 | H | H | H | H | H | H | — | — | — | — | — | — | — | — | — | — |
| 220 | H | H | H | C8H17 | H | H | — | — | — | — | — | — | — | — | — | — |

TABLE 8

| | | | | | | | | | | | | A | | | | A' | | | |
|---|---|---|---|---|---|---|---|---|---|---|---|---|---|---|---|---|---|---|---|
| No | M | m | n | A | B | A' | B' | E | G | J | B'' | R1 | R2 | R3 | R4 | R1 | R2 | R3 | R4 |
| 221 | Ir | 2 | 1 | Ph | Iq2 | — | — | CH3 | C4H9 | CH3 | — | H | C8H17 | H | H | — | — | — | — |
| 222 | Ir | 2 | 1 | Ph | Iq2 | — | — | CH3 | CH3 | H | — | H | F | CH3 | H | — | — | — | — |
| 223 | Ir | 2 | 1 | Ph | Iq2 | — | — | — | — | — | Pr | H | C8H17 | H | H | — | — | — | — |
| 224 | Ir | 2 | 1 | Ph | Iq2 | — | — | — | — | — | Iq2 | H | C8H17 | H | H | — | — | — | — |
| 225 | Ir | 3 | 0 | Ph | Iq2 | — | — | — | — | — | — | H | C9H19 | H | H | — | — | — | — |
| 226 | Ir | 3 | 0 | Ph | Iq2 | — | — | — | — | — | — | H | F | CH3 | H | — | — | — | — |
| 227 | Ir | 3 | 0 | Ph | Iq2 | — | — | — | — | — | — | H | H | F | H | — | — | — | — |
| 228 | Ir | 3 | 0 | Ph | Iq2 | — | — | — | — | — | — | H | F | H | H | — | — | — | — |
| 229 | Ir | 3 | 0 | Ph | Iq2 | — | — | — | — | — | — | H | F | H | H | — | — | — | — |
| 230 | Ir | 3 | 0 | Ph | Iq2 | — | — | — | — | — | — | H | F | H | H | — | — | — | — |
| 231 | Ir | 3 | 0 | Ph | Iq2 | — | — | — | — | — | — | H | F | H | H | — | — | — | — |
| 232 | Ir | 3 | 0 | Ph | Iq2 | — | — | — | — | — | — | F | F | F | H | — | — | — | — |
| 233 | Ir | 3 | 0 | Ph | Iq2 | — | — | — | — | — | — | F | H | F | H | — | — | — | — |
| 234 | Ir | 2 | 1 | Ph | Iq2 | — | — | — | — | — | Pr | H | C9H19 | H | H | — | — | — | — |
| 235 | Ir | 2 | 1 | Ph | Iq2 | — | — | — | — | — | Iq2 | H | C9H19 | H | H | — | — | — | — |
| 236 | Ir | 3 | 0 | Ph | Iq2 | — | — | — | — | — | — | H | C10H21 | H | H | — | — | — | — |
| 237 | Ir | 3 | 0 | Ph | Iq2 | — | — | — | — | — | — | H | C10H21 | H | H | — | — | — | — |
| 238 | Ir | 3 | 0 | Ph | Iq2 | — | — | — | — | — | — | H | C10H21 | H | H | — | — | — | — |
| 239 | Ir | 2 | 1 | Ph | Iq2 | Ph | Pr | — | — | — | — | H | C10H21 | H | H | H | H | H | H |
| 240 | Ir | 2 | 1 | Ph | Iq2 | — | — | CH3 | CH3 | H | — | H | C10H21 | H | H | — | — | — | — |
| 241 | Ir | 2 | 1 | Ph | Iq2 | — | — | CH3 | CH3 | CH3 | — | H | C10H21 | H | H | — | — | — | — |
| 242 | Ir | 2 | 1 | Ph | Iq2 | — | — | C(CH3)3 | C(CH3)3 | H | — | H | C10H21 | H | H | — | — | — | — |
| 243 | Ir | 2 | 1 | Ph | Iq2 | — | — | CH3 | C4H9 | CH3 | — | H | C10H21 | H | H | — | — | — | — |
| 244 | Ir | 2 | 1 | Ph | Iq2 | — | — | — | — | — | Pr | H | C10H21 | H | H | — | — | — | — |
| 245 | Ir | 2 | 1 | Ph | Iq2 | — | — | — | — | — | Pr | H | C10H21 | H | H | — | — | — | — |

TABLE 8-continued

| No | M | m | n | A | B | A' | B' | E | G | J | B" | R1 | R2 | R3 | R4 | R1 | R2 | R3 | R4 |
|---|---|---|---|---|---|---|---|---|---|---|---|---|---|---|---|---|---|---|---|
| 246 | Ir | 2 | 1 | Ph | Iq2 | — | — | — | — | — | Iq2 | H | C10H21 | H | H | — | — | — | — |
| 247 | Ir | 3 | 0 | Ph | Iq2 | — | — | — | — | — | — | H | C11H23 | H | H | — | — | — | — |
| 248 | Ir | 3 | 0 | Ph | Iq2 | — | — | — | — | — | — | F | H | F | H | — | — | — | — |
| 249 | Ir | 3 | 0 | Ph | Iq2 | — | — | — | — | — | — | H | H | H | H | — | — | — | — |
| 250 | Ir | 3 | 0 | Ph | Iq2 | — | — | — | — | — | — | F | F | F | H | — | — | — | — |
| 251 | Ir | 3 | 0 | Ph | Iq2 | — | — | — | — | — | — | F | F | F | H | — | — | — | — |
| 252 | Ir | 3 | 0 | Ph | Iq2 | — | — | — | — | — | — | F | F | F | H | — | — | — | — |
| 253 | Ir | 3 | 0 | Ph | Iq2 | — | — | — | — | — | — | F | F | F | H | — | — | — | — |
| 254 | Ir | 3 | 0 | Ph | Iq2 | — | — | — | — | — | — | H | CF3 | H | H | — | — | — | — |
| 255 | Ir | 3 | 0 | Ph | Iq2 | — | — | — | — | — | — | H | CF3 | H | H | — | — | — | — |
| 256 | Ir | 3 | 0 | Ph | Iq2 | — | — | — | — | — | — | H | CF3 | H | H | — | — | — | — |
| 257 | Ir | 2 | 1 | Ph | Iq2 | — | — | — | — | — | Iq2 | H | C11H23 | H | H | — | — | — | — |
| 258 | Ir | 3 | 0 | Ph | Iq2 | — | — | — | — | — | — | H | C12H25 | H | H | — | — | — | — |
| 259 | Ir | 3 | 0 | Ph | Iq2 | — | — | — | — | — | — | H | C12H25 | H | H | — | — | — | — |
| 260 | Ir | 3 | 0 | Ph | Iq2 | — | — | — | — | — | — | H | CF3 | H | H | — | — | — | — |

| | B | | | | | | B' | | | | B" | | | | | |
|---|---|---|---|---|---|---|---|---|---|---|---|---|---|---|---|---|
| No | R5 | R6 | R7 | R8 | R9 | R10 | R5 | R6 | R7 | R8 | R5 | R6 | R7 | R8 | R9 | R10 |
| 221 | H | H | H | H | H | H | — | — | — | — | — | — | — | — | — | — |
| 222 | H | H | H | H | H | H | — | — | — | — | — | — | — | — | — | — |
| 223 | H | H | H | H | H | H | — | — | — | — | H | H | C4H9 | H | — | — |
| 224 | H | H | H | H | H | H | — | — | — | — | H | H | H | H | H | H |
| 225 | H | H | H | H | H | H | — | — | — | — | — | — | — | — | — | — |
| 226 | H | H | H | H | H | H | — | — | — | — | — | — | — | — | — | — |
| 227 | H | H | H | H | CF3 | H | — | — | — | — | — | — | — | — | — | — |
| 228 | H | H | H | F | H | H | — | — | — | — | — | — | — | — | — | — |
| 229 | H | H | H | CF3 | H | H | — | — | — | — | — | — | — | — | — | — |
| 230 | H | H | H | H | F | H | — | — | — | — | — | — | — | — | — | — |
| 231 | H | H | H | H | CF3 | H | — | — | — | — | — | — | — | — | — | — |
| 232 | H | H | H | F | H | H | — | — | — | — | — | — | — | — | — | — |
| 233 | H | H | H | CF3 | H | H | — | — | — | — | H | H | C4H9 | H | — | — |
| 234 | H | H | H | H | H | H | — | — | — | — | H | H | H | H | H | H |
| 235 | H | H | H | H | H | H | — | — | — | — | H | H | H | H | H | H |
| 236 | H | H | H | H | H | H | — | — | — | — | — | — | — | — | — | — |
| 237 | H | H | H | F | H | H | — | — | — | — | — | — | — | — | — | — |
| 238 | H | H | H | H | C6H13 | H | — | — | — | — | — | — | — | — | — | — |
| 239 | H | H | H | H | H | H | H | H | H | H | — | — | — | — | — | — |
| 240 | H | H | H | F | H | H | — | — | — | — | — | — | — | — | — | — |
| 241 | H | H | H | H | H | H | — | — | — | — | — | — | — | — | — | — |
| 242 | H | H | H | H | H | H | — | — | — | — | — | — | — | — | — | — |
| 243 | H | H | H | H | H | H | — | — | — | — | — | — | — | — | — | — |
| 244 | H | H | H | H | H | H | — | — | — | — | H | H | H | H | — | — |
| 245 | H | H | H | H | H | H | — | — | — | — | H | H | C4H9 | H | — | — |
| 246 | H | H | H | H | H | H | — | — | — | — | H | H | H | H | H | H |
| 247 | H | H | H | H | H | H | — | — | — | — | — | — | — | — | — | — |
| 248 | H | H | H | H | F | H | — | — | — | — | — | — | — | — | — | — |
| 249 | H | H | H | H | CF3 | H | — | — | — | — | — | — | — | — | — | — |
| 250 | H | H | H | CF3 | H | H | — | — | — | — | — | — | — | — | — | — |
| 251 | H | H | H | F | H | H | — | — | — | — | — | — | — | — | — | — |
| 252 | H | H | H | H | F | H | — | — | — | — | — | — | — | — | — | — |
| 253 | H | H | H | H | CF3 | H | — | — | — | — | — | — | — | — | — | — |
| 254 | H | H | H | F | H | H | — | — | — | — | — | — | — | — | — | — |
| 255 | H | H | H | CF3 | H | H | — | — | — | — | — | — | — | — | — | — |
| 256 | H | H | H | H | F | H | — | — | — | — | — | — | — | — | — | — |
| 257 | H | H | H | H | H | H | — | — | — | — | H | H | H | H | H | H |
| 258 | H | H | H | H | H | H | — | — | — | — | — | — | — | — | — | — |
| 259 | H | H | H | F | H | H | — | — | — | — | — | — | — | — | — | — |
| 260 | H | H | H | H | CF3 | H | — | — | — | — | — | — | — | — | — | — |

TABLE 9

| | | | | | | | | | | | | | A | | | | A' | | |
|---|---|---|---|---|---|---|---|---|---|---|---|---|---|---|---|---|---|---|---|
| No | M | m | n | A | B | A' | B' | E | G | J | B" | R1 | R2 | R3 | R4 | R1 | R2 | R3 | R4 |
| 261 | Ir | 2 | 1 | Ph | Iq2 | Ph | Pr | — | — | — | — | H | C12H25 | H | H | H | H | H | H |
| 262 | Ir | 3 | 0 | Ph | Iq2 | — | — | — | — | — | — | H | H | CF3 | H | — | — | — | — |
| 263 | Ir | 3 | 0 | Ph | Iq2 | — | — | — | — | — | — | H | H | CF3 | H | — | — | — | — |
| 264 | Ir | 3 | 0 | Ph | Iq2 | — | — | — | — | — | — | H | H | CF3 | H | — | — | — | — |
| 265 | Ir | 3 | 0 | Ph | Iq2 | — | — | — | — | — | — | H | H | CF3 | H | — | — | — | — |
| 266 | Ir | 3 | 0 | Ph | Iq2 | — | — | — | — | — | — | H | H | CF3 | H | — | — | — | — |
| 267 | Ir | 3 | 0 | Ph | Iq2 | — | — | — | — | — | — | F | F | F | F | — | — | — | — |
| 268 | Ir | 3 | 0 | Ph | Iq2 | — | — | — | — | — | — | F | F | F | F | — | — | — | — |
| 269 | Ir | 3 | 0 | Ph | Iq2 | — | — | — | — | — | — | H | C13H27 | H | H | — | — | — | — |

TABLE 9-continued

| No | | | | | | | | | | | | | | | | | | |
|---|---|---|---|---|---|---|---|---|---|---|---|---|---|---|---|---|---|---|
| 270 | Ir | 3 | 0 | Ph | Iq2 | — | — | — | — | — | — | H | H | C7H15O | H | — | — | — |
| 271 | Ir | 3 | 0 | Ph | Iq2 | — | — | — | — | — | — | H | C15H31 | H | H | — | — | — |
| 272 | Ir | 3 | 0 | Ph | Iq2 | — | — | — | — | — | — | F | F | F | F | — | — | — |
| 273 | Ir | 3 | 0 | Ph | Iq2 | — | — | — | — | — | — | H | CF3O | H | H | — | — | — |
| 274 | Ir | 3 | 0 | Ph | Iq2 | — | — | — | — | — | — | H | C3H7O | H | H | — | — | — |
| 275 | Ir | 3 | 0 | Ph | Iq2 | — | — | — | — | — | — | H | C4H9O | H | H | — | — | — |
| 276 | Ir | 2 | 1 | Ph | Iq2 | Ph | Pr | — | — | — | — | H | C18H37 | H | H | H | H | H |
| 277 | Ir | 3 | 0 | Ph | Iq2 | — | — | — | — | — | — | H | C19H39 | H | H | — | — | — |
| 278 | Ir | 2 | 1 | Ph | Iq2 | — | — | C(CH3)3 | C(CH3)3 | H | — | H | C19H39 | H | H | — | — | — |
| 279 | Ir | 3 | 0 | Ph | Iq2 | — | — | — | — | — | — | H | C20H41 | H | H | — | — | — |
| 280 | Ir | 2 | 1 | Ph | Iq2 | — | — | — | — | — | Pr | H | C20H41 | H | H | — | — | — |
| 281 | Ir | 2 | 1 | Ph | Iq2 | Ph | Iq2 | — | — | — | — | H | CH3 | H | H | H | H | H |
| 282 | Ir | 2 | 1 | Ph | Iq2 | Ph | Iq2 | — | — | — | — | H | C2H5 | H | H | H | H | H |
| 283 | Ir | 2 | 1 | Ph | Iq2 | Ph | Iq2 | — | — | — | — | H | C3H7 | H | H | H | H | H |
| 284 | Ir | 2 | 1 | Ph | Iq2 | Ph | Iq2 | — | — | — | — | H | C4H9 | H | H | H | H | H |
| 285 | Ir | 2 | 1 | Ph | Iq2 | Ph | Iq2 | — | — | — | — | H | C(CH3)3 | H | H | H | H | H |
| 286 | Ir | 2 | 1 | Ph | Iq2 | Ph | Iq2 | — | — | — | — | H | C5H11 | H | H | H | H | H |
| 287 | Ir | 2 | 1 | Ph | Iq2 | Ph | Iq2 | — | — | — | — | H | C6H13 | H | H | H | H | H |
| 288 | Ir | 2 | 1 | Ph | Iq2 | Ph | Iq2 | — | — | — | — | H | C7H15 | H | H | H | H | H |
| 289 | Ir | 2 | 1 | Ph | Iq2 | Ph | Iq2 | — | — | — | — | H | C8H17 | H | H | H | H | H |
| 290 | Ir | 2 | 1 | Ph | Iq2 | Ph | Iq2 | — | — | — | — | H | C9H19 | H | H | H | H | H |
| 291 | Ir | 2 | 1 | Ph | Iq2 | Ph | Iq2 | — | — | — | — | H | C10H21 | H | H | H | H | H |
| 292 | Ir | 2 | 1 | Ph | Iq2 | Ph | Iq2 | — | — | — | — | H | C11H23 | H | H | H | H | H |
| 293 | Ir | 2 | 1 | Ph | Iq2 | Ph | Iq2 | — | — | — | — | H | C12H25 | H | H | H | H | H |
| 294 | Ir | 2 | 1 | Ph | Iq2 | Ph | Iq2 | — | — | — | — | H | C15H31 | H | H | F | H | H |
| 295 | Ir | 2 | 1 | Ph | Iq2 | Ph | Iq2 | — | — | — | — | H | C18H37 | H | H | H | CF3 | H |
| 296 | Ir | 2 | 1 | Ph | Iq2 | Ph | Iq2 | — | — | — | — | H | C20H41 | H | H | H | H | H |
| 297 | Ir | 2 | 1 | Ph | Iq2 | Ph | Iq2 | — | — | — | — | H | H | H | H | CH3 | H | H |
| 298 | Ir | 2 | 1 | Ph | Iq2 | Ph | Iq2 | — | — | — | — | H | H | H | H | C2H5 | H | H |
| 299 | Ir | 2 | 1 | Ph | Iq2 | Ph | Iq2 | — | — | — | — | H | H | H | H | C3H7 | H | H |
| 300 | Ir | 2 | 1 | Ph | Iq2 | Ph | Iq2 | — | — | — | — | H | H | H | H | C4H9 | H | H |

| | B | | | | | | B' | | | | | | B" | | | |
|---|---|---|---|---|---|---|---|---|---|---|---|---|---|---|---|---|
| No | R5 | R6 | R7 | R8 | R9 | R10 | R5 | R6 | R7 | R8 | R9 | R10 | R5 | R6 | R7 | R8 |
| 261 | H | H | H | H | H | H | H | H | H | H | — | — | — | — | — | — |
| 262 | H | H | H | H | H | H | — | — | — | — | — | — | — | — | — | — |
| 263 | H | H | H | H | F | H | — | — | — | — | — | — | — | — | — | — |
| 264 | H | H | H | H | CF3 | H | — | — | — | — | — | — | — | — | — | — |
| 265 | H | H | H | F | H | H | — | — | — | — | — | — | — | — | — | — |
| 266 | H | H | H | CF3 | H | H | — | — | — | — | — | — | — | — | — | — |
| 267 | H | H | H | H | H | H | — | — | — | — | — | — | — | — | — | — |
| 268 | H | H | H | H | CF3 | H | — | — | — | — | — | — | — | — | — | — |
| 269 | H | H | H | H | H | H | — | — | — | — | — | — | — | — | — | — |
| 270 | H | H | H | H | H | H | — | — | — | — | — | — | — | — | — | — |
| 271 | H | H | H | H | H | H | — | — | — | — | — | — | — | — | — | — |
| 272 | H | H | H | CF3 | H | H | — | — | — | — | — | — | — | — | — | — |
| 273 | H | H | H | H | H | H | — | — | — | — | — | — | — | — | — | — |
| 274 | H | H | H | H | H | H | — | — | — | — | — | — | — | — | — | — |
| 275 | H | H | H | H | H | H | — | — | — | — | — | — | — | — | — | — |
| 276 | H | H | H | H | H | H | H | H | H | H | — | — | — | — | — | — |
| 277 | H | H | H | H | H | H | — | — | — | — | — | — | — | — | — | — |
| 278 | H | H | H | H | H | H | — | — | — | — | — | — | — | — | — | — |
| 279 | H | H | H | H | H | H | — | — | — | — | — | — | — | — | — | — |
| 280 | H | H | H | H | H | H | — | — | — | — | — | — | H | H | H | H |
| 281 | H | H | H | H | H | H | H | H | H | H | H | H | — | — | — | — |
| 282 | H | H | H | H | H | H | H | H | H | H | H | H | — | — | — | — |
| 283 | H | H | H | H | H | H | H | H | H | H | H | H | — | — | — | — |
| 284 | H | H | H | H | H | H | H | H | H | H | H | H | — | — | — | — |
| 285 | H | H | H | H | H | H | H | H | H | H | H | H | — | — | — | — |
| 286 | H | H | H | H | H | H | H | H | H | H | H | H | — | — | — | — |
| 287 | H | H | H | H | H | H | H | H | H | H | H | H | — | — | — | — |
| 288 | H | H | H | H | H | H | H | H | H | H | H | H | — | — | — | — |
| 289 | H | H | H | H | H | H | H | H | H | H | H | H | — | — | — | — |
| 290 | H | H | H | H | H | H | H | H | H | H | H | H | — | — | — | — |
| 291 | H | H | H | H | H | H | H | H | H | H | H | H | — | — | — | — |
| 292 | H | H | H | H | H | H | H | H | H | H | H | H | — | — | — | — |
| 293 | H | H | H | F | H | H | H | H | H | H | H | H | — | — | — | — |
| 294 | H | H | H | H | H | H | H | H | H | H | H | H | — | — | — | — |
| 295 | H | H | H | H | H | H | H | H | H | H | H | H | — | — | — | — |
| 296 | H | H | H | —C≡CC4H9 | H | H | H | H | H | H | H | H | — | — | — | — |
| 297 | H | H | H | H | H | H | — | — | — | — | — | — | — | — | — | — |
| 298 | H | H | H | H | H | H | — | — | — | — | — | — | — | — | — | — |
| 299 | H | H | H | H | H | H | — | — | — | — | — | — | — | — | — | — |
| 300 | H | H | H | H | H | H | — | — | — | — | — | — | — | — | — | — |

TABLE 10

| No | M | m | n | A | B | A' | B' | R1 | A R2 | R3 | R4 | R1 | A' R2 | R3 | R4 |
|---|---|---|---|---|---|---|---|---|---|---|---|---|---|---|---|
| 301 | Ir | 2 | 1 | Ph | Iq2 | Ph | Iq2 | H | H | H | H | H | C(CH3)3 | H | H |
| 302 | Ir | 2 | 1 | Ph | Iq2 | Ph | Iq2 | H | H | H | H | H | C5H11 | H | H |
| 303 | Ir | 2 | 1 | Ph | Iq2 | Ph | Iq2 | H | H | H | H | H | C6H13 | H | H |
| 304 | Ir | 2 | 1 | Ph | Iq2 | Ph | Iq2 | H | H | H | H | H | C7H15 | H | H |
| 305 | Ir | 2 | 1 | Ph | Iq2 | Ph | Iq2 | H | H | H | H | H | C8H17 | H | H |
| 306 | Ir | 2 | 1 | Ph | Iq2 | Ph | Iq2 | H | CH2OC5H11 | H | H | H | C9H19 | H | H |
| 307 | Ir | 2 | 1 | Ph | Iq2 | Ph | Iq2 | H | H | H | H | H | C10H21 | H | H |
| 308 | Ir | 2 | 1 | Ph | Iq2 | Ph | Iq2 | H | H | H | H | H | C11H23 | H | H |
| 309 | Ir | 2 | 1 | Ph | Iq2 | Ph | Iq2 | H | H | H | H | H | C12H25 | H | H |
| 310 | Ir | 2 | 1 | Ph | Iq2 | Ph | Iq2 | H | H | H | H | H | C15H31 | H | H |
| 311 | Ir | 2 | 1 | Ph | Iq2 | Ph | Iq2 | H | H | H | H | H | C18H37 | H | H |
| 312 | Ir | 2 | 1 | Ph | Iq2 | Ph | Iq2 | H | H | H | H | H | C20H41 | H | H |
| 313 | Ir | 3 | 0 | Ph | Iq2 | — | — | H | H | CH3 | H | — | — | — | — |
| 314 | Ir | 3 | 0 | Ph | Iq2 | — | — | H | H | C2H5 | H | — | — | — | — |
| 315 | Ir | 3 | 0 | Ph | Iq2 | — | — | H | H | CH(CH3)2 | H | — | — | — | — |
| 316 | Ir | 3 | 0 | Ph | Iq2 | — | — | H | H | C4H9 | H | — | — | — | — |
| 317 | Ir | 3 | 0 | Ph | Iq2 | — | — | H | H | C(CH3)3 | H | — | — | — | — |
| 318 | Ir | 3 | 0 | Ph | Iq2 | — | — | H | H | C5H11 | H | — | — | — | — |
| 319 | Ir | 3 | 0 | Ph | Iq2 | — | — | H | H | C6H13 | H | — | — | — | — |
| 320 | Ir | 3 | 0 | Ph | Iq2 | — | — | H | H | C7H15 | H | — | — | — | — |
| 321 | Ir | 3 | 0 | Ph | Iq2 | — | — | H | H | C8H17 | H | — | — | — | — |
| 322 | Ir | 3 | 0 | Ph | Iq2 | — | — | H | H | C9H19 | H | — | — | — | — |
| 323 | Ir | 3 | 0 | Ph | Iq2 | — | — | H | H | C10H21 | H | — | — | — | — |
| 324 | Ir | 3 | 0 | Ph | Iq2 | — | — | H | H | C11H23 | H | — | — | — | — |
| 325 | Ir | 3 | 0 | Ph | Iq2 | — | — | H | H | C12H25 | H | — | — | — | — |
| 326 | Ir | 3 | 0 | Ph | Iq2 | — | — | H | H | C15H31 | H | — | — | — | — |
| 327 | Ir | 3 | 0 | Ph | Iq2 | — | — | H | H | C18H37 | H | — | — | — | — |
| 328 | Ir | 3 | 0 | Ph | Iq2 | — | — | H | H | C20H41 | H | — | — | — | — |
| 329 | Ir | 2 | 1 | Ph | Iq2 | Ph | Iq2 | H | H | CH3 | H | H | H | H | H |
| 330 | Ir | 2 | 1 | Ph | Iq2 | Ph | Iq2 | H | H | C2H5 | H | H | H | H | H |
| 331 | Ir | 2 | 1 | Ph | Iq2 | Ph | Iq2 | H | H | C3H7 | H | H | H | H | H |
| 332 | Ir | 2 | 1 | Ph | Iq2 | Ph | Iq2 | H | H | C4H9 | H | H | H | H | H |
| 333 | Ir | 2 | 1 | Ph | Iq2 | Ph | Iq2 | H | H | C(CH3)3 | H | H | H | H | H |
| 334 | Ir | 2 | 1 | Ph | Iq2 | Ph | Iq2 | H | H | C5H11 | H | H | H | H | H |
| 335 | Ir | 3 | 0 | Ph | Iq2 | Ph | Iq2 | H | H | C6H13 | H | H | H | H | H |
| 336 | Ir | 2 | 1 | Ph | Iq2 | Ph | Iq2 | H | H | C7H15 | H | H | H | H | H |
| 337 | Ir | 2 | 1 | Ph | Iq2 | Ph | Iq2 | H | H | C8H17 | H | H | H | H | H |
| 338 | Ir | 2 | 1 | Ph | Iq2 | Ph | Iq2 | H | H | C9H19 | H | H | H | H | H |
| 339 | Ir | 2 | 1 | Ph | Iq2 | Ph | Iq2 | H | H | C10H21 | H | H | H | H | H |
| 340 | Ir | 2 | 1 | Ph | Iq2 | Ph | Iq2 | H | H | C11H23 | H | H | H | H | H |

| No | B R5 | R6 | R7 | R8 | R9 | R10 | B' R5 | R6 | R7 | R8 | R9 | R10 |
|---|---|---|---|---|---|---|---|---|---|---|---|---|
| 301 | H | H | H | H | H | H | H | H | H | H | H | H |
| 302 | H | H | H | H | H | H | H | H | H | H | H | H |
| 303 | H | H | H | H | H | H | H | H | H | H | H | H |
| 304 | H | H | H | H | H | H | H | H | H | H | H | H |
| 305 | H | H | H | H | H | H | H | H | H | H | H | H |
| 306 | H | H | H | H | H | H | H | H | H | H | H | H |
| 307 | H | H | H | H | H | H | H | H | H | H | H | H |
| 308 | H | H | H | H | H | H | H | H | H | H | H | H |
| 309 | H | H | H | H | H | H | H | H | H | H | H | H |
| 310 | H | H | H | —CH=CH—CH3 | H | H | H | H | H | H | H | H |
| 311 | H | H | H | H | H | H | H | H | H | H | H | H |
| 312 | H | H | H | H | H | H | H | H | H | H | H | H |
| 313 | H | H | H | H | H | H | — | — | — | — | — | — |
| 314 | H | H | H | H | H | H | — | — | — | — | — | — |
| 315 | H | H | H | H | H | H | — | — | — | — | — | — |
| 316 | H | H | H | H | H | H | — | — | — | — | — | — |
| 317 | H | H | H | H | H | H | — | — | — | — | — | — |
| 318 | H | H | H | H | H | H | — | — | — | — | — | — |
| 319 | H | H | H | H | H | H | — | — | — | — | — | — |
| 320 | H | H | H | H | H | H | — | — | — | — | — | — |
| 321 | H | H | H | H | H | H | — | — | — | — | — | — |
| 322 | H | H | H | H | H | H | — | — | — | — | — | — |
| 323 | H | H | H | H | H | H | — | — | — | — | — | — |
| 324 | H | H | H | H | H | H | — | — | — | — | — | — |
| 325 | H | H | H | H | H | H | — | — | — | — | — | — |
| 326 | H | H | H | COOC6H13 | H | H | — | — | — | — | — | — |
| 327 | H | H | H | H | H | H | — | — | — | — | — | — |
| 328 | H | H | H | OCH2C3F7 | H | H | — | — | — | — | — | — |
| 329 | H | H | H | H | H | H | H | H | H | H | H | H |
| 330 | H | H | H | H | H | H | H | H | H | H | H | H |

TABLE 10-continued

| | | | | | | | | | | | | |
|---|---|---|---|---|---|---|---|---|---|---|---|---|
| 331 | H | H | H | H | H | H | H | H | H | H | H | H |
| 332 | H | H | H | H | H | H | H | H | H | H | H | H |
| 333 | H | H | H | H | H | H | H | H | H | H | H | H |
| 334 | H | H | H | H | H | H | H | H | H | H | H | H |
| 335 | H | H | H | H | H | H | H | H | H | H | H | H |
| 336 | H | H | H | H | H | H | H | H | H | H | H | H |
| 337 | H | H | H | H | H | H | H | H | H | H | H | H |
| 338 | H | H | H | H | H | H | H | H | H | H | H | H |
| 339 | H | H | H | H | H | H | H | H | H | H | H | H |
| 340 | H | H | H | H | H | H | H | H | H | H | H | H |

TABLE 11-1

| No | M | m | n | A | B | A' | B' | E | G | J | B" | R1 | A R2 | R3 | R4 | A' R1 | R2 | R3 | R4 |
|---|---|---|---|---|---|---|---|---|---|---|---|---|---|---|---|---|---|---|---|
| 341 | Ir | 2 | 1 | Ph | Iq2 | Ph | Iq2 | — | — | — | — | H | H | C12H25 | H | H | H | H | H |
| 342 | Ir | 2 | 1 | Ph | Iq2 | Ph | Iq2 | — | — | — | — | H | H | C15H31 | H | H | H | H | H |
| 343 | Ir | 2 | 1 | Ph | Iq2 | Ph | Iq2 | — | — | — | — | H | H | C18H37 | H | H | H | H | H |
| 344 | Ir | 2 | 1 | Ph | Iq2 | Ph | Iq2 | — | — | — | — | H | H | C20H41 | H | H | H | H | H |
| 345 | Ir | 2 | 1 | Ph | Iq2 | Ph | Iq2 | — | — | — | — | H | H | H | H | H | H | CH3 | H |
| 346 | Ir | 2 | 1 | Ph | Iq2 | Ph | Iq2 | — | — | — | — | H | H | H | H | H | H | C2H5 | H |
| 347 | Ir | 2 | 1 | Ph | Iq2 | Ph | Iq2 | — | — | — | — | H | H | H | H | H | H | C3H7 | H |
| 348 | Ir | 2 | 1 | Ph | Iq2 | Ph | Iq2 | — | — | — | — | H | H | H | H | H | H | C4H9 | H |
| 349 | Ir | 2 | 1 | Ph | Iq2 | Ph | Iq2 | — | — | — | — | H | H | H | H | H | H | C(CH3)3 | H |
| 350 | Ir | 2 | 1 | Ph | Iq2 | Ph | Iq2 | — | — | — | — | H | H | H | H | H | H | C5H11 | H |
| 351 | Ir | 2 | 1 | Ph | Iq2 | Ph | Iq2 | — | — | — | — | H | H | H | H | H | H | C6H13 | H |
| 352 | Ir | 2 | 1 | Ph | Iq2 | Ph | Iq2 | — | — | — | — | H | H | H | H | H | H | C7H15 | H |
| 353 | Ir | 2 | 1 | Ph | Iq2 | Ph | Iq2 | — | — | — | — | H | H | H | H | H | H | C8H17 | H |
| 354 | Ir | 2 | 1 | Ph | Iq2 | Ph | Iq2 | — | — | — | — | H | H | H | H | H | H | C9H19 | H |
| 355 | Ir | 2 | 1 | Ph | Iq2 | Ph | Iq2 | — | — | — | — | H | H | H | H | H | H | C10H21 | H |
| 356 | Ir | 2 | 1 | Ph | Iq2 | Ph | Iq2 | — | — | — | — | H | H | COCH3 | H | H | H | C11H23 | H |
| 357 | Ir | 2 | 1 | Ph | Iq2 | Ph | Iq2 | — | — | — | — | H | H | H | H | H | H | C12H25 | H |
| 358 | Ir | 2 | 1 | Ph | Iq2 | Ph | Iq2 | — | — | — | — | H | H | C7H15O | H | H | H | C15H31 | H |
| 359 | Ir | 2 | 1 | Ph | Iq2 | Ph | Iq2 | — | — | — | — | H | H | H | H | H | H | C18H37 | H |
| 360 | Ir | 2 | 1 | Ph | Iq2 | Ph | Iq2 | — | — | — | — | H | H | CN | H | H | H | C20H41 | H |
| 361 | Ir | 3 | 0 | Ph | Iq2 | — | — | — | — | — | — | H | 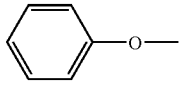 | H | H | — | — | — | — |
| 362 | Ir | 3 | 0 | Ph | Iq2 | — | — | — | — | — | — | H | 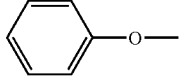 | H | H | — | — | — | — |
| 363 | Ir | 3 | 0 | Ph | Iq2 | — | — | — | — | — | — | H | 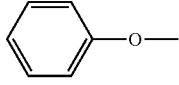 | H | H | — | — | — | — |
| 364 | Ir | 2 | 1 | Ph | Iq2 | Ph | Pr | — | — | — | — | H | 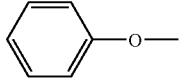 | H | H | H | H | H | H |
| 365 | Ir | 2 | 1 | Ph | Iq2 | — | — | CH3 | CH3 | H | — | H | 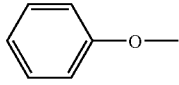 | H | H | — | — | — | — |
| 366 | Ir | 2 | 1 | Ph | Iq2 | — | — | CH3 | CH3 | CH3 | — | H | 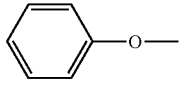 | H | H | — | — | — | — |
| 367 | Ir | 2 | 1 | Ph | Iq2 | — | — | C(CH3)3 | C(CH3)3 | H | — | H | 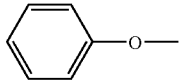 | H | H | — | — | — | — |

TABLE 11-1-continued

| | | | | | | | | | | | | | Structure | | | | | |
|---|---|---|---|---|---|---|---|---|---|---|---|---|---|---|---|---|---|---|
| 368 | Ir | 2 | 1 | Ph | Iq2 | — | — | CH3 | C4H9 | CH3 | — | H | Ph-O-CH3 | H | H | — | — | — |
| 369 | Ir | 2 | 1 | Ph | Iq2 | — | — | — | — | — | Pr | H | Ph-O-CH3 | H | H | — | — | — |
| 370 | Ir | 2 | 1 | Ph | Iq2 | — | — | — | — | — | Pr | H | Ph-O-CH3 | H | H | — | — | — |
| 371 | Ir | 2 | 1 | Ph | Iq2 | — | — | — | — | — | Iq2 | H | Ph-O-CH3 | H | H | — | — | — |
| 372 | Ir | 3 | 0 | Ph | Iq2 | — | — | — | — | — | — | H | CH3O | H | H | — | — | — |
| 373 | Ir | 3 | 0 | Ph | Iq2 | — | — | — | — | — | — | H | CH3O | H | H | H | H | H |
| 374 | Ir | 2 | 1 | Ph | Iq2 | Ph | Pr | — | — | — | — | H | CH3O | H | H | — | — | — |
| 375 | Ir | 3 | 0 | Ph | Iq2 | — | — | — | — | — | — | H | H | CH3O | H | H | — | — |
| 376 | Ir | 2 | 1 | Ph | Iq2 | — | — | CH3 | CH3 | CH3 | — | H | CH3O | H | H | — | — | — |
| 377 | Ir | 2 | 1 | Ph | Iq2 | — | — | C(CH3)3 | C(CH3)3 | H | — | H | CH3O | H | H | — | — | — |
| 378 | Ir | 2 | 1 | Ph | Iq2 | — | — | CH3 | C4H9 | CH3 | — | H | CH3O | H | H | — | — | — |
| 379 | Ir | 2 | 1 | Ph | Iq2 | — | — | — | — | — | Pr | H | CH3O | H | H | — | — | — |
| 380 | Ir | 2 | 1 | Ph | Iq2 | — | — | — | — | — | Pr | H | CH3O | H | H | — | — | — |

| B | | | | | | B' | | | | | | B" | | | | | |
|---|---|---|---|---|---|---|---|---|---|---|---|---|---|---|---|---|---|
| R5 | R6 | R7 | R8 | R9 | R10 | R5 | R6 | R7 | R8 | R9 | R10 | R5 | R6 | R7 | R8 | R9 | R10 |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | H | H | H | H | H | H | H | H | H | H | — | — |
| H | H | H | H | H | H | H | H | H | H | H | H | H | H | C4H9 | H | — | — |
| H | H | H | H | H | H | — | — | — | — | — | — | H | H | H | H | H | H |
| H | H | H | F | H | H | — | — | — | — | — | — | — | — | — | — | — | — |
| H | H | H | H | C6H13 | H | — | — | — | — | — | — | — | — | — | — | — | — |
| H | H | H | H | H | H | H | H | H | H | — | — | — | — | — | — | — | — |
| H | H | H | H | H | H | — | — | — | — | — | — | — | — | — | — | — | — |
| H | H | H | H | H | H | — | — | — | — | — | — | — | — | — | — | — | — |
| H | H | H | H | H | H | — | — | — | — | — | — | — | — | — | — | — | — |
| H | H | H | H | H | H | — | — | — | — | — | — | — | — | — | — | — | — |
| H | H | H | F | H | H | — | — | — | — | — | — | — | — | — | — | — | — |
| H | H | H | H | C6H13 | H | — | — | — | — | — | — | — | — | — | — | — | — |
| H | H | H | H | H | H | H | H | H | H | — | — | — | — | — | — | — | — |
| H | H | H | H | H | H | — | — | — | — | — | — | — | — | — | — | — | — |
| H | H | H | H | H | H | — | — | — | — | — | — | — | — | — | — | — | — |
| H | H | H | H | H | H | — | — | — | — | — | — | — | — | — | — | — | — |
| H | H | H | H | H | H | — | — | — | — | — | — | H | H | H | H | — | — |
| H | H | H | H | H | H | — | — | — | — | — | — | H | H | C4H9 | H | — | — |

TABLE 12

| No | M | m | n | A B | A | B | E | G | J | B | A R1 | R2 | R3 | R4 | A' R1 | R2 | R3 | R4 |
|---|---|---|---|---|---|---|---|---|---|---|---|---|---|---|---|---|---|---|
| 381 | Ir | 2 | 1 | Ph Iq2 | — | — | — | — | — | Iq2 | H | CH3O | H | H | — | — | — | — |
| 382 | Ir | 3 | 0 | Ph Iq2 | — | — | — | — | — | — | H | C2H5O | H | H | — | — | — | — |
| 383 | Ir | 3 | 0 | Ph Iq2 | — | — | — | — | — | — | H | C2H5O | H | H | — | — | — | — |
| 384 | Ir | 3 | 0 | Ph Iq2 | — | — | — | — | — | — | H | C2H5O | H | H | — | — | — | — |
| 385 | Ir | 2 | 1 | Ph Iq2 | Ph | Pr | — | — | — | — | H | C2H5O | H | H | H | H | H | H |
| 386 | Ir | 2 | 1 | Ph Iq2 | — | — | CH3 | CH3 | H | — | H | C2H5O | H | H | — | — | — | — |
| 387 | Ir | 2 | 1 | Ph Iq2 | — | — | CH3 | CH3 | CH3 | — | H | C2H5O | H | H | — | — | — | — |
| 388 | Ir | 2 | 1 | Ph Iq2 | — | — | C(CH3)3 | C(CH3)3 | H | — | H | C2H5O | H | H | — | — | — | — |
| 389 | Ir | 2 | 1 | Ph Iq2 | — | — | CH3 | C4H9 | CH3 | — | H | C2H5O | H | H | — | — | — | — |
| 390 | Ir | 2 | 1 | Ph Iq2 | — | — | — | — | — | Pr | H | C2H5O | H | H | — | — | — | — |
| 391 | Ir | 2 | 1 | Ph Iq2 | — | — | — | — | — | Pr | H | C2H5O | H | H | — | — | — | — |
| 392 | Ir | 2 | 1 | Ph Iq2 | — | — | — | — | — | Iq2 | H | C2H5O | H | H | — | — | — | — |
| 393 | Ir | 3 | 0 | Ph Iq2 | — | — | — | — | — | — | H | C6H13O | H | H | — | — | — | — |
| 394 | Ir | 3 | 0 | Ph Iq2 | — | — | — | — | — | — | H | C6H13O | H | H | — | — | — | — |
| 395 | Ir | 2 | 1 | Ph Iq2 | Ph | Pr | — | — | — | — | H | C6H13O | H | H | H | H | H | H |
| 396 | Ir | 2 | 1 | Ph Iq2 | — | — | CH3 | CH3 | H | — | H | C6H13O | H | H | — | — | — | — |
| 397 | Ir | 2 | 1 | Ph Iq2 | — | — | CH3 | CH3 | CH3 | — | H | C6H13O | H | H | — | — | — | — |
| 399 | Ir | 2 | 1 | Ph Iq2 | — | — | CH3 | C4H9 | CH3 | — | H | C6H13O | H | H | — | — | — | — |
| 400 | Ir | 2 | 1 | Ph Iq2 | — | — | — | — | — | Pr | H | C6H13O | H | H | — | — | — | — |
| 401 | Ir | 2 | 1 | Ph Iq2 | — | — | — | — | — | Pr | H | C6H13O | H | H | — | — | — | — |
| 402 | Ir | 2 | 1 | Ph Iq2 | — | — | — | — | — | Iq2 | H | C6H13O | H | H | — | — | — | — |
| 403 | Ir | 3 | 0 | Ph Iq2 | — | — | — | — | — | — | H | C7H15O | H | H | — | — | — | — |
| 404 | Ir | 3 | 0 | Ph Iq2 | — | — | — | — | — | — | H | C7H15O | H | H | — | — | — | — |
| 405 | Ir | 3 | 0 | Ph Iq2 | — | — | — | — | — | — | H | C7H15O | H | H | — | — | — | — |
| 406 | Ir | 3 | 0 | Ph Iq2 | — | — | — | — | — | — | H | (CH3)3CO | H | H | — | — | — | — |
| 407 | Ir | 3 | 0 | Ph Iq2 | — | — | — | — | — | — | H | C5H11O | H | H | — | — | — | — |
| 408 | Ir | 3 | 0 | Ph Iq2 | — | — | — | — | — | — | H | CF3O | H | H | — | — | — | — |
| 409 | Ir | 3 | 0 | Ph Iq2 | — | — | — | — | — | — | H | CF3O | H | H | — | — | — | — |
| 410 | Ir | 3 | 0 | Ph Iq2 | — | — | — | — | — | — | H | CF3O | H | H | — | — | — | — |
| 411 | Ir | 3 | 0 | Ph Iq2 | — | — | — | — | — | — | H | CF3O | H | H | — | — | — | — |
| 412 | Ir | 3 | 0 | Ph Iq2 | — | — | — | — | — | — | H | C7H15O | H | H | — | — | — | — |
| 413 | Ir | 2 | 1 | Ph Iq2 | — | — | — | — | — | Iq2 | H | C7H15O | H | H | — | — | — | — |
| 414 | Ir | 3 | 0 | Ph Iq2 | — | — | — | — | — | — | H | (C4H9)3Si | H | H | — | — | — | — |
| 415 | Ir | 3 | 0 | Ph Iq2 | — | — | — | — | — | — | H | C12H25O | H | H | — | — | — | — |
| 416 | Ir | 3 | 0 | Ph Iq2 | — | — | — | — | — | — | H | C12H25O | H | H | — | — | — | — |
| 417 | Ir | 2 | 1 | Ph Iq2 | Ph | Pr | — | — | — | — | H | C12H25O | H | H | H | H | H | H |
| 418 | Ir | 2 | 1 | Ph Iq2 | — | — | CH3 | CH3 | H | — | H | (CH3)3Si | H | H | — | — | — | — |
| 419 | Ir | 2 | 1 | Ph Iq2 | — | — | — | — | — | Pr | H | C18H37O | H | H | — | — | — | — |
| 420 | Ir | 2 | 1 | Ph Iq2 | — | — | — | — | — | Iq2 | H | C18H37O | H | H | — | — | — | — |

| No | B R5 | R6 | R7 | R8 | R9 | R10 | B' R5 | R6 | R7 | R8 | B'' R5 | R6 | R7 | R8 | R9 | R10 |
|---|---|---|---|---|---|---|---|---|---|---|---|---|---|---|---|---|
| 381 | H | H | H | H | H | H | — | — | — | — | H | H | H | H | H | H |
| 382 | H | H | H | H | H | H | — | — | — | — | — | — | — | — | — | — |
| 383 | H | H | H | F | H | H | — | — | — | — | — | — | — | — | — | — |
| 384 | H | H | H | H | C6H13 | H | — | — | — | — | — | — | — | — | — | — |
| 385 | H | H | H | H | H | H | H | H | H | H | — | — | — | — | — | — |
| 386 | H | H | H | H | H | H | — | — | — | — | — | — | — | — | — | — |
| 387 | H | H | H | H | H | H | — | — | — | — | — | — | — | — | — | — |
| 388 | H | H | H | H | H | H | — | — | — | — | — | — | — | — | — | — |
| 389 | H | H | H | H | H | H | — | — | — | — | — | — | — | — | — | — |
| 390 | H | H | H | H | H | H | — | — | — | — | H | H | H | H | — | — |
| 391 | H | H | H | H | H | H | — | — | — | — | H | H | C4H9 | H | — | — |
| 392 | H | H | H | H | H | H | — | — | — | — | H | H | H | H | H | H |
| 393 | H | H | H | F | H | H | — | — | — | — | — | — | — | — | — | — |
| 394 | H | H | H | H | C6H13 | H | — | — | — | — | — | — | — | — | — | — |
| 395 | H | H | H | H | H | H | H | H | H | H | — | — | — | — | — | — |
| 396 | H | H | H | H | H | H | — | — | — | — | — | — | — | — | — | — |
| 397 | H | H | H | H | H | H | — | — | — | — | — | — | — | — | — | — |
| 399 | H | H | H | H | H | H | — | — | — | — | — | — | — | — | — | — |
| 400 | H | H | H | H | H | H | — | — | — | — | H | H | H | H | — | — |
| 401 | H | H | H | H | H | H | — | — | — | — | H | H | C4H9 | H | — | — |
| 402 | H | H | H | H | H | H | — | — | — | — | H | H | H | H | H | H |
| 403 | H | H | H | H | H | H | — | — | — | — | — | — | — | — | — | — |
| 404 | H | H | H | F | H | H | — | — | — | — | — | — | — | — | — | — |
| 405 | H | H | H | H | C6H13 | H | — | — | — | — | — | — | — | — | — | — |
| 406 | H | H | H | H | H | H | — | — | — | — | — | — | — | — | — | — |
| 407 | H | H | H | H | H | H | — | — | — | — | — | — | — | — | — | — |
| 408 | H | H | H | F | H | H | — | — | — | — | — | — | — | — | — | — |
| 409 | H | H | H | H | F | H | — | — | — | — | — | — | — | — | — | — |
| 410 | H | H | H | CF3 | H | H | — | — | — | — | — | — | — | — | — | — |
| 411 | H | H | H | H | CF3 | H | — | — | — | — | — | — | — | — | — | — |
| 412 | H | H | H | F | H | H | — | — | — | — | — | — | — | — | — | — |

TABLE 12-continued

| No | | | | | | | | | | | | | | | |
|---|---|---|---|---|---|---|---|---|---|---|---|---|---|---|---|
| 413 | H | H | H | H | H | H | — | — | — | — | H | H | H | H | H | H |
| 414 | H | H | H | H | H | H | — | — | — | — | — | — | — | — | — | — |
| 415 | H | H | H | F | H | H | — | — | — | — | — | — | — | — | — | — |
| 416 | H | H | H | H | C6H13 | H | — | — | — | — | — | — | — | — | — | — |
| 417 | H | H | H | H | H | H | H | H | H | H | — | — | — | — | — | — |
| 418 | H | H | H | H | H | H | — | — | — | — | — | — | — | — | — | — |
| 419 | H | H | H | H | H | H | — | — | — | — | H | H | C4H9 | H | — | — |
| 420 | H | H | H | H | H | H | — | — | — | — | H | H | H | H | H | H |

TABLE 13

| No | M | m | n | A | B | A' | B' | E | G | J | B" | A R1 | R2 | R3 | R4 | A' R1 | R2 | R3 | R4 |
|---|---|---|---|---|---|---|---|---|---|---|---|---|---|---|---|---|---|---|---|
| 421 | Ir | 3 | 0 | Ph | Iq2 | — | — | — | — | — | — | F | H | F | H | — | — | — | — |
| 422 | Ir | 3 | 0 | Ph | Iq2 | — | — | — | — | — | — | F | H | F | H | — | — | — | — |
| 423 | Ir | 3 | 0 | Ph | Iq2 | — | — | — | — | — | — | F | H | F | H | — | — | — | — |
| 424 | Ir | 2 | 1 | Ph | Iq2 | Ph | Pr | — | — | — | — | F | H | F | H | H | H | H | H |
| 425 | Ir | 2 | 1 | Ph | Iq2 | — | — | CH3 | CH3 | H | — | F | H | F | H | — | — | — | — |
| 426 | Ir | 2 | 1 | Ph | Iq2 | — | — | CH3 | CH3 | CH3 | — | F | H | F | H | — | — | — | — |
| 427 | Ir | 2 | 1 | Ph | Iq2 | — | — | C(CH3)3 | C(CH3)3 | H | — | F | H | F | H | — | — | — | — |
| 428 | Ir | 2 | 1 | Ph | Iq2 | — | — | CH3 | C4H9 | CH3 | — | F | H | F | H | — | — | — | — |
| 429 | Ir | 2 | 1 | Ph | Iq2 | — | — | — | — | — | Pr | F | H | F | H | — | — | — | — |
| 430 | Ir | 2 | 1 | Ph | Iq2 | — | — | — | — | — | Pr | F | H | F | H | — | — | — | — |
| 431 | Ir | 2 | 1 | Ph | Iq2 | — | — | — | — | — | Iq2 | F | H | F | H | — | — | — | — |
| 432 | Ir | 3 | 0 | Ph | Iq2 | — | — | — | — | — | — | H | F | H | F | — | — | — | — |
| 433 | Ir | 3 | 0 | Ph | Iq2 | — | — | — | — | — | — | H | F | H | F | — | — | — | — |
| 434 | Ir | 3 | 0 | Ph | Iq2 | — | — | — | — | — | — | H | F | H | F | — | — | — | — |
| 435 | Ir | 2 | 1 | Ph | Iq2 | Ph | Pr | — | — | — | — | H | F | H | F | H | H | H | H |
| 436 | Ir | 2 | 1 | Ph | Iq2 | — | — | CH3 | CH3 | H | — | H | F | H | F | — | — | — | — |
| 437 | Ir | 2 | 1 | Ph | Iq2 | — | — | CH3 | CH3 | CH3 | — | H | F | H | F | — | — | — | — |
| 438 | Ir | 2 | 1 | Ph | Iq2 | — | — | C(CH3)3 | C(CH3)3 | H | — | H | F | H | F | — | — | — | — |
| 439 | Ir | 2 | 1 | Ph | Iq2 | — | — | CH3 | C4H9 | CH3 | — | H | F | H | F | — | — | — | — |
| 440 | Ir | 2 | 1 | Ph | Iq2 | — | — | — | — | — | Pr | H | F | H | F | — | — | — | — |
| 441 | Ir | 2 | 1 | Ph | Iq2 | — | — | — | — | — | Pr | H | F | H | F | — | — | — | — |
| 442 | Ir | 2 | 1 | Ph | Iq2 | — | — | — | — | — | Iq2 | H | F | H | F | — | — | — | — |
| 443 | Ir | 3 | 0 | Ph | Iq2 | — | — | — | — | — | — | F | F | F | F | — | — | — | — |
| 444 | Ir | 3 | 0 | Ph | Iq2 | — | — | — | — | — | — | F | F | F | F | — | — | — | — |
| 445 | Ir | 3 | 0 | Ph | Iq2 | — | — | — | — | — | — | F | F | F | F | — | — | — | — |
| 446 | Ir | 2 | 1 | Ph | Iq2 | Ph | Pr | — | — | — | — | F | F | F | F | H | H | H | H |
| 447 | Ir | 2 | 1 | Ph | Iq2 | — | — | CH3 | CH3 | H | — | F | F | F | F | — | — | — | — |
| 448 | Ir | 2 | 1 | Ph | Iq2 | — | — | CH3 | CH3 | CH3 | — | F | F | F | F | — | — | — | — |
| 449 | Ir | 2 | 1 | Ph | Iq2 | — | — | C(CH3)3 | C(CH3)3 | H | — | F | F | F | F | — | — | — | — |
| 450 | Ir | 2 | 1 | Ph | Iq2 | — | — | CH3 | C4H9 | CH3 | — | F | F | F | F | — | — | — | — |
| 451 | Ir | 2 | 1 | Ph | Iq2 | — | — | — | — | — | Pr | F | F | F | F | — | — | — | — |
| 452 | Ir | 2 | 1 | Ph | Iq2 | — | — | — | — | — | Pr | F | F | F | F | — | — | — | — |
| 453 | Ir | 2 | 1 | Ph | Iq2 | — | — | — | — | — | Iq2 | F | F | F | F | — | — | — | — |
| 454 | Ir | 3 | 0 | Ph | Iq2 | — | — | — | — | — | — | F | F | F | F | — | — | — | — |
| 455 | Ir | 3 | 0 | Ph | Iq2 | — | — | — | — | — | — | F | F | F | F | — | — | — | — |
| 456 | Ir | 2 | 1 | Ph | Iq2 | Ph | Pr | — | — | — | — | F | F | F | F | H | H | H | H |
| 457 | Ir | 2 | 1 | Ph | Iq2 | — | — | CH3 | CH3 | H | — | F | F | F | F | — | — | — | — |
| 458 | Ir | 2 | 1 | Ph | Iq2 | — | — | CH3 | CH3 | CH3 | — | F | F | F | F | — | — | — | — |
| 459 | Ir | 2 | 1 | Ph | Iq2 | — | — | C(CH3)3 | C(CH3)3 | H | — | F | F | F | F | — | — | — | — |

| No | B R5 | R6 | R7 | R8 | R9 | R10 | B' R5 | R6 | R7 | R8 | B" R5 | R6 | R7 | R8 | R9 | R10 |
|---|---|---|---|---|---|---|---|---|---|---|---|---|---|---|---|---|
| 421 | H | H | H | H | H | H | — | — | — | — | — | — | — | — | — | — |
| 422 | H | H | H | F | H | H | — | — | — | — | — | — | — | — | — | — |
| 423 | H | H | H | H | C6H13 | H | — | — | — | — | — | — | — | — | — | — |
| 424 | H | H | H | H | H | H | H | H | H | H | — | — | — | — | — | — |
| 425 | H | H | H | H | H | H | — | — | — | — | — | — | — | — | — | — |
| 426 | H | H | H | H | H | H | — | — | — | — | — | — | — | — | — | — |
| 427 | H | H | H | H | H | H | — | — | — | — | — | — | — | — | — | — |
| 428 | H | H | H | H | H | H | — | — | — | — | — | — | — | — | — | — |
| 429 | H | H | H | H | H | H | — | — | — | — | H | H | H | H | — | — |
| 430 | H | H | H | H | H | H | — | — | — | — | H | H | C4H9 | H | — | — |
| 431 | H | H | H | H | F | H | — | — | — | — | H | H | H | H | H | H |
| 432 | H | H | H | H | F | H | — | — | — | — | — | — | — | — | — | — |
| 433 | H | H | H | F | F | H | — | — | — | — | — | — | — | — | — | — |
| 434 | H | H | H | H | C6H13 | H | — | — | — | — | — | — | — | — | — | — |
| 435 | H | H | H | H | H | H | H | H | H | H | — | — | — | — | — | — |
| 436 | H | H | H | H | H | H | — | — | — | — | — | — | — | — | — | — |
| 437 | H | H | H | H | H | H | — | — | — | — | — | — | — | — | — | — |

TABLE 13-continued

| | | | | | | | | | | | | | | | |
|---|---|---|---|---|---|---|---|---|---|---|---|---|---|---|---|
| 438 | H | H | H | H | H | H | — | — | — | — | — | — | — | — | — |
| 439 | H | H | H | H | H | H | — | — | — | — | — | — | — | — | — |
| 440 | H | H | H | H | H | H | — | — | — | — | H | H | C4H9 | H | — |
| 441 | H | H | H | H | H | H | — | — | — | — | H | H | C4H9 | H | — |
| 442 | H | H | H | H | H | H | — | — | — | — | H | H | H | H | H |
| 443 | H | H | H | H | H | H | — | — | — | — | — | — | — | — | — |
| 444 | H | H | H | F | H | H | — | — | — | — | — | — | — | — | — |
| 445 | H | H | H | H | C6H13 | H | — | — | — | — | — | — | — | — | — |
| 446 | H | H | H | H | H | H | H | H | H | H | — | — | — | — | — |
| 447 | H | H | H | H | H | H | — | — | — | — | — | — | — | — | — |
| 448 | H | H | H | H | H | H | — | — | — | — | — | — | — | — | — |
| 449 | H | H | H | H | H | H | — | — | — | — | — | — | — | — | — |
| 450 | H | H | H | H | H | H | — | — | — | — | — | — | — | — | — |
| 451 | H | H | H | H | H | H | — | — | — | — | H | H | H | H | — |
| 452 | H | H | H | H | H | H | — | — | — | — | H | H | C4H9 | H | — |
| 453 | H | H | H | H | H | H | — | — | — | — | H | H | H | H | H |
| 454 | F | F | F | F | F | F | — | — | — | — | — | — | — | — | — |
| 455 | F | F | F | F | C6H13 | F | — | — | — | — | — | — | — | — | — |
| 456 | F | F | F | F | F | F | H | H | H | H | — | — | — | — | — |
| 457 | F | F | F | F | F | F | — | — | — | — | — | — | — | — | — |
| 458 | F | F | F | F | F | F | — | — | — | — | — | — | — | — | — |
| 459 | F | F | F | F | F | F | — | — | — | — | — | — | — | — | — |

TABLE 14

| No | M | m | n | A | B | A' | B' | E | G | J | B" | A R1 | A R2 | A R3 | A R4 | A' R1 | A' R2 | A' R3 | A' R4 |
|---|---|---|---|---|---|---|---|---|---|---|---|---|---|---|---|---|---|---|---|
| 460 | Ir | 2 | 1 | Ph | Iq2 | — | — | CH3 | C4H9 | CH3 | — | F | F | F | F | — | — | — | — |
| 461 | Ir | 2 | 1 | Ph | Iq2 | — | — | — | — | — | Pr | F | F | F | F | — | — | — | — |
| 462 | Ir | 2 | 1 | Ph | Iq2 | — | — | — | — | — | Pr | F | F | F | F | — | — | — | — |
| 463 | Ir | 2 | 1 | Ph | Iq2 | — | — | — | — | — | Iq2 | F | F | F | F | — | — | — | — |
| 464 | Ir | 3 | 0 | Ph | Iq2 | — | — | — | — | — | — | H | C2F5 | H | H | — | — | — | — |
| 465 | Ir | 3 | 0 | Ph | Iq2 | — | — | — | — | — | — | H | C2F5 | H | H | — | — | — | — |
| 466 | Ir | 3 | 0 | Ph | Iq2 | — | — | — | — | — | — | H | C3F7 | H | H | — | — | — | — |
| 467 | Ir | 2 | 1 | Ph | Iq2 | Ph | Pr | — | — | — | — | H | C3F7 | H | H | H | H | H | H |
| 468 | Ir | 2 | 1 | Ph | Iq2 | — | — | CH3 | CH3 | H | — | H | C4H9 | H | H | — | — | — | — |
| 469 | Ir | 3 | 0 | Ph | Iq2 | — | — | — | — | — | — | H | C3F7CH2CH2O | H | H | — | — | — | — |
| 470 | Ir | 2 | 1 | Ph | Iq2 | Ph | Iq2 | — | — | — | — | H | C3F7CH2CH2O | H | H | H | H | H | H |
| 471 | Ir | 1 | 2 | Ph | Iq2 | Ph | Iq2 | — | — | — | — | H | C3F7CH2CH2O | H | H | H | H | H | H |
| 472 | Ir | 2 | 1 | Ph | Iq2 | — | — | — | — | — | Pr | H | C5F11 | H | H | — | — | — | — |
| 473 | Ir | 2 | 1 | Ph | Iq2 | — | — | — | — | — | Pr | H | C2F5 | H | H | — | — | — | — |
| 474 | Ir | 2 | 1 | Ph | Iq2 | — | — | — | — | — | Iq2 | H | C3F7 | H | H | — | — | — | — |
| 475 | Ir | 3 | 0 | Ph | Iq2 | — | — | — | — | — | — | H | C6F13 | H | H | — | — | — | — |
| 476 | Ir | 3 | 0 | Ph | Iq2 | — | — | — | — | — | — | H | C6F13 | H | H | — | — | — | — |
| 477 | Ir | 3 | 0 | Ph | Iq2 | — | — | — | — | — | — | H | C6F13 | H | H | — | — | — | — |
| 478 | Ir | 3 | 0 | Ph | Iq2 | — | — | — | — | — | — | H | C6F13 | H | H | — | — | — | — |
| 479 | Ir | 2 | 1 | Ph | Iq2 | Ph | Iq2 | — | — | — | — | H | C6F13 | H | H | H | H | H | H |
| 480 | Ir | 2 | 1 | Ph | Iq2 | Ph | Iq2 | — | — | — | — | H | H | H | H | H | C6F13 | H | H |
| 481 | Ir | 3 | 0 | Ph | Iq2 | — | — | — | — | — | — | H | C6F13CH2O | H | H | — | — | — | — |
| 482 | Ir | 2 | 1 | Ph | Iq2 | — | — | CH3 | C4H9 | CH3 | — | H | C18F37 | H | H | — | — | — | — |
| 483 | Ir | 2 | 1 | Ph | Iq2 | Ph | Iq2 | — | — | — | — | H | C6F13CH2O | H | H | H | H | H | H |
| 484 | Ir | 1 | 2 | Ph | Iq2 | Ph | Iq2 | — | — | — | — | H | C6F13CH2O | H | H | H | H | H | H |
| 485 | Ir | 2 | 1 | Ph | Iq2 | — | — | — | — | — | Iq2 | H | C20F41 | H | H | — | — | — | — |
| 486 | Ir | 3 | 0 | Ph | Iq2 | — | — | — | — | — | — | H | 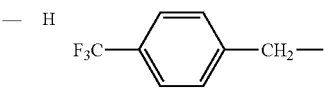 | H | H | — | — | — | — |
| 487 | Ir | 3 | 0 | Ph | Iq2 | — | — | — | — | — | — | H | 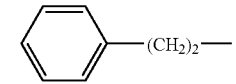 | H | H | — | — | — | — |
| 488 | Ir | 3 | 0 | Ph | Iq2 | — | — | — | — | — | — | H | 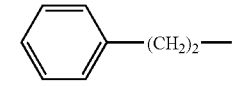 | H | H | — | — | — | — |
| 489 | Ir | 2 | 1 | Ph | Iq2 | Ph | Pr | — | — | — | — | H | 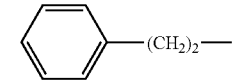 | H | H | H | H | H | H |

TABLE 14-continued

| | | | | | | | | | | | | | | | | | |
|---|---|---|---|---|---|---|---|---|---|---|---|---|---|---|---|---|---|
| 490 | Ir | 2 | 1 | Ph | Iq2 | — | — | CH3 | CH3 | H | — | H | 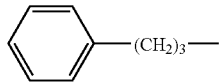 | H | H | — | — — — |
| 491 | Ir | 2 | 1 | Ph | Iq2 | — | — | CH3 | CH3 | CH3 | — | H | 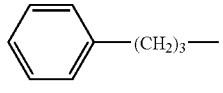 | H | H | — | — — — |
| 492 | Ir | 2 | 1 | Ph | Iq2 | — | — | C(CH3)3 | C(CH3)3 | H | — | H | 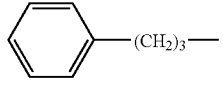 | H | H | — | — — — |
| 493 | Ir | 2 | 1 | Ph | Iq2 | — | — | CH3 | C4H9 | CH3 | — | H | 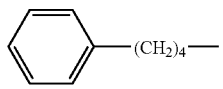 | H | H | — | — — — |
| 494 | Ir | 2 | 1 | Ph | Iq2 | — | — | — | — | — | Pr | H | 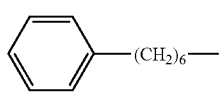 | H | H | — | — — — |
| 495 | Ir | 2 | 1 | Ph | Iq2 | — | — | — | — | — | Pr | H | 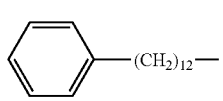 | H | H | — | — — — |
| 496 | Ir | 2 | 1 | Ph | Iq2 | — | — | — | — | — | Iq2 | H | 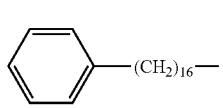 | CH3 | H | — | — — — |
| 497 | Ir | 3 | 0 | Ph | Iq2 | — | — | — | — | — | — | H | H | F | F | — | — — — |
| 498 | Ir | 3 | 0 | Ph | Iq2 | — | — | — | — | — | — | H | H | F | F | — | — — — |
| 499 | Ir | 3 | 0 | Ph | Iq2 | — | — | — | — | — | — | H | H | F | F | — | — — — |
| 500 | Ir | 2 | 1 | Ph | Iq2 | Ph | Pr | — | — | — | — | H | H | F | F | H | H H H |
| 501 | Ir | 2 | 1 | Ph | Iq2 | — | — | CH3 | CH3 | H | — | H | H | F | F | — | — — — |
| 502 | Ir | 2 | 1 | Ph | Iq2 | — | — | CH3 | CH3 | CH3 | — | H | H | F | F | — | — — — |
| 503 | Ir | 2 | 1 | Ph | Iq2 | — | — | C(CH3)3 | C(CH3)3 | H | — | H | H | F | F | — | — — — |
| 504 | Ir | 2 | 1 | Ph | Iq2 | — | — | CH3 | C4H9 | CH3 | — | H | H | F | F | — | — — — |
| 505 | Ir | 2 | 1 | Ph | Iq2 | — | — | — | — | — | Pr | H | H | F | F | — | — — — |
| 506 | Ir | 2 | 1 | Ph | Iq2 | — | — | — | — | — | Pr | H | H | F | F | — | — — — |
| 507 | Ir | 2 | 1 | Ph | Iq2 | — | — | — | — | — | Iq2 | H | H | F | F | — | — — — |
| 508 | Ir | 3 | 0 | Ph | Iq2 | — | — | — | — | — | — | H | CH3 | F | F | — | — — — |
| 509 | Ir | 3 | 0 | Ph | Iq2 | — | — | — | — | — | — | H | CH3 | F | F | — | — — — |

| B | | | | | | B' | | | | | | B'' | | | | | |
|---|---|---|---|---|---|---|---|---|---|---|---|---|---|---|---|---|---|
| R5 | R6 | R7 | R8 | R9 | R10 | R5 | R6 | R7 | R8 | R9 | R10 | R5 | R6 | R7 | R8 | R9 | R10 |
| F | F | F | F | F | F | — | — | — | — | — | — | — | — | — | — | — | — |
| F | F | F | F | F | F | — | — | — | — | — | — | H | H | H | H | — | — |
| F | F | F | F | F | F | — | — | — | — | — | — | H | H | C4H9 | H | — | — |
| F | F | F | F | F | F | — | — | — | — | — | — | H | H | H | H | H | H |
| H | H | H | H | H | H | — | — | — | — | — | — | — | — | — | — | — | — |
| H | H | H | F | H | H | — | — | — | — | — | — | — | — | — | — | — | — |
| H | H | H | H | C6H13 | H | — | — | — | — | — | — | — | — | — | — | — | — |
| H | H | H | H | H | H | H | H | H | H | — | — | — | — | — | — | — | — |
| H | H | H | H | H | H | — | — | — | — | — | — | — | — | — | — | — | — |
| H | H | H | H | H | H | — | — | — | — | — | — | — | — | — | — | — | — |
| H | H | H | H | H | H | H | H | H | H | H | H | — | — | — | — | — | — |
| H | H | H | H | H | H | H | H | H | H | H | H | — | — | — | — | — | — |
| H | H | H | H | H | H | — | — | — | — | — | — | H | CH3 | H | H | — | — |
| H | H | H | H | H | H | — | — | — | — | — | — | H | H | C4H9 | H | — | — |
| H | H | H | H | H | H | — | — | — | — | — | — | H | H | H | H | H | H |
| H | H | H | CF3 | H | H | — | — | — | — | — | — | — | — | — | — | — | — |
| H | H | H | H | CF3 | H | — | — | — | — | — | — | — | — | — | — | — | — |
| H | H | H | H | F | H | — | — | — | — | — | — | — | — | — | — | — | — |
| H | H | H | H | H | H | — | — | — | — | — | — | — | — | — | — | — | — |
| H | H | H | H | H | H | H | H | H | H | H | H | — | — | — | — | — | — |
| H | H | H | H | H | H | — | — | — | — | — | — | H | H | H | H | H | H |
| H | H | H | H | H | H | — | — | — | — | — | — | — | — | — | — | — | — |
| H | H | H | H | H | H | — | — | — | — | — | — | — | — | — | — | — | — |
| H | H | H | H | H | H | H | H | H | H | H | H | — | — | — | — | — | — |
| H | H | H | H | H | H | — | — | — | — | — | — | — | — | — | — | — | — |
| H | H | H | H | H | H | — | — | — | — | — | — | — | — | — | — | — | — |

TABLE 14-continued

| | | | | | | | | | | | | | | | | |
|---|---|---|---|---|---|---|---|---|---|---|---|---|---|---|---|---|
| H | H | H | H | H | H | — | — | — | — | — | — | — | — | — | — | — |
| H | H | H | F | H | H | — | — | — | — | — | — | — | — | — | — | — |
| H | H | H | H | C6H13 | H | — | — | — | — | — | — | — | — | — | — | — |
| H | H | H | H | H | H | H | H | H | H | — | — | — | — | — | — | — |
| H | H | H | H | H | H | — | — | — | — | — | — | — | — | — | — | — |
| H | H | H | H | H | H | — | — | — | — | — | — | — | — | — | — | — |
| H | H | H | H | H | H | — | — | — | — | — | — | — | — | — | — | — |
| H | H | H | H | H | H | — | — | — | — | — | H | H | H | H | — | — |
| H | H | H | H | H | H | — | — | — | — | — | H | H | C2H5 | H | — | — |
| H | H | H | H | H | H | — | — | — | — | — | H | H | H | H | H | H |
| H | H | H | H | H | H | — | — | — | — | — | — | — | — | — | — | — |
| H | H | H | F | H | H | — | — | — | — | — | — | — | — | — | — | — |
| H | H | H | H | C6H13 | H | — | — | — | — | — | — | — | — | — | — | — |
| H | H | H | H | H | H | H | H | H | H | — | — | — | — | — | — | — |
| H | H | H | H | H | H | — | — | — | — | — | — | — | — | — | — | — |
| H | H | H | H | H | H | — | — | — | — | — | — | — | — | — | — | — |
| H | H | H | H | H | H | — | — | — | — | — | — | — | — | — | — | — |
| H | H | H | H | H | H | — | — | — | — | — | — | — | — | — | — | — |
| H | H | H | H | H | H | — | — | — | — | — | H | H | H | H | — | — |
| H | H | H | H | H | H | — | — | — | — | — | H | H | C4H9 | H | — | — |
| H | H | H | H | H | H | — | — | — | — | — | H | H | H | H | H | H |
| H | H | H | CF3 | H | H | — | — | — | — | — | — | — | — | — | — | — |
| H | H | H | F | H | H | — | — | — | — | — | — | — | — | — | — | — |

TABLE 15

| No | M | m | n | A | B | A' | B' | E | G | J | B" | A R1 | A R2 | A R3 | A R4 | A' R1 | A' R2 |
|---|---|---|---|---|---|---|---|---|---|---|---|---|---|---|---|---|---|
| 510 | Ir | 3 | 0 | Ph | Iq2 | — | — | — | — | — | — | H | CH3 | F | F | — | — |
| 511 | Ir | 2 | 1 | Ph | Iq2 | Ph | Pr | — | — | — | — | H | CH3 | F | F | H | H |
| 512 | Ir | 2 | 1 | Ph | Iq2 | — | — | CH3 | CH3 | H | — | H | CH3 | F | F | — | — |
| 513 | Ir | 2 | 1 | Ph | Iq2 | — | — | CH3 | CH3 | CH3 | — | H | CH3 | F | F | — | — |
| 514 | Ir | 2 | 1 | Ph | Iq2 | — | — | C(CH3)3 | C(CH3)3 | H | — | H | CH3 | F | F | — | — |
| 515 | Ir | 2 | 1 | Ph | Iq2 | — | — | CH3 | C4H9 | CH3 | — | H | CH3 | F | F | — | — |
| 516 | Ir | 2 | 1 | Ph | Iq2 | — | — | — | — | — | Pr | H | CH3 | F | F | — | — |
| 517 | Ir | 2 | 1 | Ph | Iq2 | — | — | — | — | — | Pr | H | CH3 | F | F | — | — |
| 518 | Ir | 2 | 1 | Ph | Iq2 | — | — | — | — | — | Iq2 | H | CH3 | F | F | — | — |
| 519 | Ir | 3 | 0 | Ph | Iq2 | — | — | — | — | — | — | H | C2H5 | F | F | — | — |
| 520 | Ir | 3 | 0 | Ph | Iq2 | — | — | — | — | — | — | H | C2H5 | F | F | — | — |
| 521 | Ir | 3 | 0 | Ph | Iq2 | — | — | — | — | — | — | H | C2H5 | F | F | — | — |
| 522 | Ir | 2 | 1 | Ph | Iq2 | Ph | Pr | — | — | — | — | H | C2H5 | F | F | H | H |
| 523 | Ir | 2 | 1 | Ph | Iq2 | — | — | CH3 | CH3 | H | — | H | C2H5 | F | F | — | — |
| 524 | Ir | 2 | 1 | Ph | Iq2 | — | — | CH3 | CH3 | CH3 | — | H | C2H5 | F | F | — | — |
| 525 | Ir | 2 | 1 | Ph | Iq2 | — | — | C(CH3)3 | C(CH3)3 | H | — | H | C2H5 | F | F | — | — |
| 526 | Ir | 2 | 1 | Ph | Iq2 | — | — | CH3 | C4H9 | CH3 | — | H | C3H7 | F | F | — | — |
| 527 | Ir | 2 | 1 | Ph | Iq2 | — | — | — | — | — | Pr | H | C3H7 | F | F | — | — |
| 528 | Ir | 2 | 1 | Ph | Iq2 | — | — | — | — | — | Pr | H | C3H7 | F | F | — | — |
| 529 | Ir | 2 | 1 | Ph | Iq2 | — | — | — | — | — | Iq2 | H | C3H7 | F | F | — | — |
| 530 | Ir | 3 | 0 | Ph | Iq2 | — | — | — | — | — | — | H | C4H9 | F | F | — | — |
| 531 | Ir | 3 | 0 | Ph | Iq2 | — | — | — | — | — | — | H | C4H9 | F | F | — | — |
| 532 | Ir | 3 | 0 | Ph | Iq2 | — | — | — | — | — | — | H | C4H9 | F | F | — | — |
| 533 | Ir | 2 | 1 | Ph | Iq2 | Ph | Pr | — | — | — | — | H | C4H9 | F | F | H | H |
| 534 | Ir | 2 | 1 | Ph | Iq2 | — | — | CH3 | CH3 | H | — | H | C4H9 | F | F | — | — |
| 535 | Ir | 2 | 1 | Ph | Iq2 | — | — | CH3 | CH3 | CH3 | — | H | C4H9 | F | F | — | — |
| 536 | Ir | 2 | 1 | Ph | Iq2 | — | — | C(CH3)3 | C(CH3)3 | H | — | H | C4H9 | F | F | — | — |
| 537 | Ir | 2 | 1 | Ph | Iq2 | — | — | CH3 | C4H9 | CH3 | — | H | C4H9 | F | F | — | — |
| 538 | Ir | 2 | 1 | Ph | Iq2 | — | — | — | — | — | Pr | H | C4H9 | F | F | — | — |
| 539 | Ir | 2 | 1 | Ph | Iq2 | — | — | — | — | — | Pr | H | C4H9 | F | F | — | — |
| 540 | Ir | 2 | 1 | Ph | Iq2 | — | — | — | — | — | Iq2 | H | C4H9 | F | F | — | — |
| 541 | Ir | 3 | 0 | Ph | Iq2 | — | — | — | — | — | — | H | C(CH3)3 | F | F | — | — |
| 542 | Ir | 3 | 0 | Ph | Iq2 | — | — | — | — | — | — | H | C(CH3)3 | F | F | — | — |
| 543 | Ir | 3 | 0 | Ph | Iq2 | — | — | — | — | — | — | H | C(CH3)3 | F | F | — | — |
| 544 | Ir | 2 | 1 | Ph | Iq2 | Ph | Pr | — | — | — | — | H | C(CH3)3 | F | F | H | H |
| 545 | Ir | 2 | 1 | Ph | Iq2 | — | — | CH3 | CH3 | F | — | H | C5H11 | F | F | — | — |
| 546 | Ir | 2 | 1 | Ph | Iq2 | — | — | CH3 | CH3 | CH3 | — | H | C5H11 | F | F | — | — |
| 547 | Ir | 2 | 1 | Ph | Iq2 | — | — | C(CH3)3 | C(CH3)3 | H | — | H | C5H11 | F | F | — | — |
| 548 | Ir | 2 | 1 | Ph | Iq2 | — | — | CH3 | C4H9 | CH3 | — | H | C5H11 | F | F | — | — |
| 549 | Ir | 2 | 1 | Ph | Iq2 | — | — | — | — | — | Pr | H | C5H11 | F | F | — | — |

TABLE 15-continued

| No | A' R3 | A' R4 | B R5 | B R6 | B R7 | B R8 | B R9 | B R10 | B' R5 | B' R6 | B' R7 | B' R8 | B'' R5 | B'' R6 | B'' R7 | B'' R8 | B'' R9 | B'' R10 |
|---|---|---|---|---|---|---|---|---|---|---|---|---|---|---|---|---|---|---|
| 510 | — | — | H | H | H | H | C6H13 | H | — | — | — | — | — | — | — | — | — | — |
| 511 | H | H | H | H | H | H | H | H | H | H | H | H | — | — | — | — | — | — |
| 512 | — | — | H | H | H | H | H | H | — | — | — | — | — | — | — | — | — | — |
| 513 | — | — | H | H | H | H | H | H | — | — | — | — | — | — | — | — | — | — |
| 514 | — | — | H | H | H | H | H | H | — | — | — | — | — | — | — | — | — | — |
| 515 | — | — | H | H | H | H | H | H | — | — | — | — | — | — | — | — | — | — |
| 516 | — | — | H | H | H | H | H | H | — | — | — | — | H | H | H | H | — | — |
| 517 | — | — | H | H | H | H | H | H | — | — | — | — | H | H | C4H9 | H | — | — |
| 518 | — | — | H | H | H | H | H | H | — | — | — | — | H | H | H | H | H | H |
| 519 | — | — | H | H | H | H | H | H | — | — | — | — | — | — | — | — | — | — |
| 520 | — | — | H | H | H | F | H | H | — | — | — | — | — | — | — | — | — | — |
| 521 | — | — | H | H | H | H | C6H13 | H | — | — | — | — | — | — | — | — | — | — |
| 522 | H | H | H | H | H | H | H | H | H | H | H | H | — | — | — | — | — | — |
| 523 | — | — | H | H | H | H | H | H | — | — | — | — | — | — | — | — | — | — |
| 524 | — | — | H | H | H | H | H | H | — | — | — | — | — | — | — | — | — | — |
| 525 | — | — | H | H | H | H | H | H | — | — | — | — | — | — | — | — | — | — |
| 526 | — | — | H | H | H | H | H | H | — | — | — | — | — | — | — | — | — | — |
| 527 | — | — | H | H | H | H | H | H | — | — | — | — | H | H | H | H | — | — |
| 528 | — | — | H | H | H | H | H | H | — | — | — | — | H | H | C4H9 | H | — | — |
| 529 | — | — | H | H | H | H | H | H | — | — | — | — | H | H | H | H | H | H |
| 530 | — | — | H | H | H | H | H | H | — | — | — | — | — | — | — | — | — | — |
| 531 | — | — | H | H | H | F | H | H | — | — | — | — | — | — | — | — | — | — |
| 532 | — | — | H | H | H | H | C6H13 | H | — | — | — | — | — | — | — | — | — | — |
| 533 | H | H | H | H | H | H | H | H | H | H | H | H | — | — | — | — | — | — |
| 534 | — | — | H | H | H | H | H | H | — | — | — | — | — | — | — | — | — | — |
| 535 | — | — | H | H | H | H | H | H | — | — | — | — | — | — | — | — | — | — |
| 536 | — | — | H | H | H | H | H | H | — | — | — | — | — | — | — | — | — | — |
| 537 | — | — | H | H | H | H | H | H | — | — | — | — | — | — | — | — | — | — |
| 538 | — | — | H | H | H | H | H | H | — | — | — | — | H | H | H | H | — | — |
| 539 | — | — | H | H | H | H | H | H | — | — | — | — | H | H | CH3 | H | — | — |
| 540 | — | — | H | H | H | H | H | H | — | — | — | — | H | H | H | H | H | H |
| 541 | — | — | H | H | H | CF3 | H | H | — | — | — | — | — | — | — | — | — | — |
| 542 | — | — | H | H | H | F | H | H | — | — | — | — | — | — | — | — | — | — |
| 543 | — | — | H | H | H | H | C6H13 | H | — | — | — | — | — | — | — | — | — | — |
| 544 | H | H | H | H | H | H | H | H | H | H | H | H | — | — | — | — | — | — |
| 545 | — | — | H | H | H | H | H | H | — | — | — | — | — | — | — | — | — | — |
| 546 | — | — | H | H | H | H | H | H | — | — | — | — | — | — | — | — | — | — |
| 547 | — | — | H | H | H | H | H | H | — | — | — | — | — | — | — | — | — | — |
| 548 | — | — | H | H | H | H | H | H | — | — | — | — | — | — | — | — | — | — |
| 549 | — | — | H | H | H | H | H | H | — | — | — | — | H | H | H | H | — | — |

TABLE 16

| No | M | m | n | A | B | A' | B' | E | G | J | B'' | A R1 | A R2 | A R3 | A R4 | A' R1 | A' R2 |
|---|---|---|---|---|---|---|---|---|---|---|---|---|---|---|---|---|---|
| 550 | Ir | 2 | 1 | Ph | Iq2 | — | — | — | — | — | Pr | H | C6H13 | F | F | — | — |
| 551 | Ir | 2 | 1 | Ph | Iq2 | — | — | — | — | — | Iq2 | H | C6H13 | F | F | — | — |
| 552 | Ir | 3 | 0 | Ph | Iq2 | — | — | — | — | — | — | H | C6H13 | F | F | — | — |
| 553 | Ir | 3 | 0 | Ph | Iq2 | — | — | — | — | — | — | H | C6H13 | F | F | — | — |
| 554 | Ir | 3 | 0 | Ph | Iq2 | — | — | — | — | — | — | H | C6H13 | F | F | — | — |
| 555 | Ir | 2 | 1 | Ph | Iq2 | Ph | Pr | — | — | — | — | H | C6H13 | F | F | H | H |
| 556 | Ir | 2 | 1 | Ph | Iq2 | — | — | CF3 | CF3 | H | — | H | C6H13 | F | F | — | — |
| 557 | Ir | 2 | 1 | Ph | Iq2 | — | — | CH3 | CH3 | CH3 | — | H | C6H13 | F | F | — | — |
| 558 | Ir | 2 | 1 | Ph | Iq2 | — | — | C(CH3)3 | C(CH3)3 | H | — | H | C7H15 | F | F | — | — |
| 559 | Ir | 2 | 1 | Ph | Iq2 | — | — | CH3 | C4H9 | CH3 | — | H | C7H15 | F | F | — | — |
| 560 | Ir | 2 | 1 | Ph | Iq2 | — | — | — | — | — | Pr | H | C7H15 | F | F | — | — |
| 561 | Ir | 2 | 1 | Ph | Iq2 | — | — | — | — | — | Pr | H | C8H17 | F | F | — | — |
| 562 | Ir | 2 | 1 | Ph | Iq2 | — | — | — | — | — | Iq2 | H | C8H17 | F | F | — | — |
| 563 | Ir | 3 | 0 | Ph | Iq2 | — | — | — | — | — | — | H | C8H17 | F | F | — | — |
| 564 | Ir | 3 | 0 | Ph | Iq2 | — | — | — | — | — | — | H | C9H19 | F | F | — | — |
| 565 | Ir | 3 | 0 | Ph | Iq2 | — | — | — | — | — | — | H | C9H19 | F | F | — | — |
| 566 | Ir | 2 | 1 | Ph | Iq2 | Ph | Pr | — | — | — | — | H | C10H21 | F | F | H | H |
| 567 | Ir | 2 | 1 | Ph | Iq2 | — | — | CH3 | CH3 | H | — | H | C10H21 | F | F | — | — |
| 568 | Ir | 2 | 1 | Ph | Iq2 | — | — | CH3 | CH3 | CH3 | — | H | C11H23 | F | F | — | — |
| 569 | Ir | 2 | 1 | Ph | Iq2 | — | — | C(CH3)3 | C(CH3)3 | H | — | H | C12H25 | F | F | — | — |
| 570 | Ir | 2 | 1 | Ph | Iq2 | — | — | CH3 | C4H9 | CH3 | — | H | C13H27 | F | F | — | — |
| 571 | Ir | 2 | 1 | Ph | Iq2 | — | — | — | — | — | Pr | H | C14H29 | F | F | — | — |
| 572 | Ir | 2 | 1 | Ph | Iq2 | — | — | — | — | — | Pr | H | C15H31 | F | F | — | — |
| 573 | Ir | 2 | 1 | Ph | Iq2 | — | — | — | — | — | Iq2 | H | C15H31 | F | F | — | — |
| 574 | Ir | 3 | 0 | Ph | Iq2 | — | — | — | — | — | — | H | C16H33 | F | F | — | — |

TABLE 16-continued

| No | M | m | n | A | B | A' | B' | E | G | J | B" | R1 | R2 | R3 | R4 |
|---|---|---|---|---|---|---|---|---|---|---|---|---|---|---|---|
| 575 | Ir | 3 | 0 | Ph | Iq2 | — | — | — | — | — | — | H | C17H35 | F | F | — | — |
| 576 | Ir | 3 | 0 | Ph | Iq2 | — | — | — | — | — | — | H | C17H35 | F | F | — | — |
| 577 | Ir | 2 | 1 | Ph | Iq2 | Ph | Pr | — | — | — | — | H | C17H35 | F | F | H | H |
| 578 | Ir | 2 | 1 | Ph | Iq2 | — | — | CH3 | CH3 | H | — | H | C17H35 | F | F | — | — |
| 579 | Ir | 2 | 1 | Ph | Iq2 | — | — | CH3 | CH3 | CH3 | — | H | C17H35 | F | F | — | — |
| 580 | Ir | 2 | 1 | Ph | Iq2 | — | — | C(CH3)3 | C(CH3)3 | H | — | H | C18H37 | F | F | — | — |
| 581 | Ir | 2 | 1 | Ph | Iq2 | — | — | CH3 | C4H9 | CH3 | — | H | C18H37 | F | F | — | — |
| 582 | Ir | 2 | 1 | Ph | Iq2 | — | — | — | — | — | Pr | H | C18H37 | F | F | — | — |
| 583 | Ir | 2 | 1 | Ph | Iq2 | — | — | — | — | — | Pr | H | C19H39 | F | F | — | — |
| 584 | Ir | 2 | 1 | Ph | Iq2 | — | — | — | — | — | Iq2 | H | C20H41 | F | F | — | — |
| 585 | Ir | 3 | 0 | Ph | Iq2 | — | — | — | — | — | — | F | F | F | H | — | — |
| 586 | Ir | 3 | 0 | Ph | Iq2 | — | — | — | — | — | — | F | F | F | H | — | — |
| 587 | Ir | 3 | 0 | Ph | Iq2 | — | — | — | — | — | — | F | F | F | H | — | — |
| 588 | Ir | 2 | 1 | Ph | Iq2 | Ph | Pr | — | — | — | — | F | F | F | H | H | H |
| 589 | Ir | 2 | 1 | Ph | Iq2 | — | — | CH3 | CH3 | H | — | F | F | F | H | — | — |

| | A' | B | | | | | | B' | | | | B" | | | | | |
|---|---|---|---|---|---|---|---|---|---|---|---|---|---|---|---|---|---|
| No | R3 R4 | R5 | R6 | R7 | R8 | R9 | R10 | R5 | R6 | R7 | R8 | R5 | R6 | R7 | R8 | R9 | R10 |
| 550 | — — | H | H | H | H | H | H | — | — | — | — | H | H | C4H9 | H | — | — |
| 551 | — — | H | H | H | H | H | H | — | — | — | — | H | H | H | H | H | H |
| 552 | — — | H | H | H | H | H | H | — | — | — | — | — | — | — | — | — | — |
| 553 | — — | H | H | H | F | H | H | — | — | — | — | — | — | — | — | — | — |
| 554 | — — | H | H | H | H | C6H13 | H | — | — | — | — | — | — | — | — | — | — |
| 555 | H H | H | H | H | H | H | H | H | H | H | H | — | — | — | — | — | — |
| 556 | — — | H | H | H | H | H | H | — | — | — | — | — | — | — | — | — | — |
| 557 | — — | H | H | H | H | H | H | — | — | — | — | — | — | — | — | — | — |
| 558 | — — | H | H | H | H | H | H | — | — | — | — | — | — | — | — | — | — |
| 559 | — — | H | H | H | H | H | H | — | — | — | — | — | — | — | — | — | — |
| 560 | — — | H | H | H | H | H | H | — | — | — | — | H | H | H | H | — | — |
| 561 | — — | H | H | H | H | H | H | — | — | — | — | H | H | C4H9 | H | — | — |
| 562 | — — | H | H | H | H | H | H | — | — | — | — | H | H | H | H | H | H |
| 563 | — — | H | H | H | H | H | H | — | — | — | — | — | — | — | — | — | — |
| 564 | — — | H | H | H | F | H | H | — | — | — | — | — | — | — | — | — | — |
| 565 | — — | H | H | H | H | C6H13 | H | — | — | — | — | — | — | — | — | — | — |
| 566 | H H | H | H | H | H | H | H | H | H | H | H | — | — | — | — | — | — |
| 567 | — — | H | H | H | H | H | H | — | — | — | — | — | — | — | — | — | — |
| 568 | — — | H | H | H | H | H | H | — | — | — | — | — | — | — | — | — | — |
| 569 | — — | H | H | H | H | H | H | — | — | — | — | — | — | — | — | — | — |
| 570 | — — | H | H | H | H | H | H | — | — | — | — | — | — | — | — | — | — |
| 571 | — — | H | H | H | H | H | H | — | — | — | — | H | H | H | H | — | — |
| 572 | — — | H | H | H | H | H | H | — | — | — | — | H | H | C4H9 | H | — | — |
| 573 | — — | H | H | H | H | H | H | — | — | — | — | H | H | H | H | H | H |
| 574 | — — | H | H | H | H | H | H | — | — | — | — | — | — | — | — | — | — |
| 575 | — — | H | H | H | F | H | H | — | — | — | — | — | — | — | — | — | — |
| 576 | — — | H | H | H | H | C6H13 | H | — | — | — | — | — | — | — | — | — | — |
| 577 | H H | H | H | H | H | H | H | H | H | H | H | — | — | — | — | — | — |
| 578 | — — | H | H | H | H | H | H | — | — | — | — | — | — | — | — | — | — |
| 579 | — — | H | H | H | H | H | H | — | — | — | — | — | — | — | — | — | — |
| 580 | — — | H | H | H | H | H | H | — | — | — | — | — | — | — | — | — | — |
| 581 | — — | H | H | H | H | H | H | — | — | — | — | — | — | — | — | — | — |
| 582 | — — | H | H | H | H | H | H | — | — | — | — | H | H | H | H | — | — |
| 583 | — — | H | H | H | H | H | H | — | — | — | — | H | H | C2H5 | H | — | — |
| 584 | — — | H | H | H | H | H | H | — | — | — | — | H | H | H | H | H | H |
| 585 | — — | H | H | H | H | H | H | — | — | — | — | — | — | — | — | — | — |
| 586 | — — | H | H | H | F | H | H | — | — | — | — | — | — | — | — | — | — |
| 587 | — — | H | H | H | H | C6H13 | H | — | — | — | — | — | — | — | — | — | — |
| 588 | H H | H | H | H | H | H | H | H | H | H | H | — | — | — | — | — | — |
| 589 | — — | H | H | H | H | H | H | — | — | — | — | — | — | — | — | — | — |

TABLE 17

| | | | | | | | | | | | | A | | | | A' | |
|---|---|---|---|---|---|---|---|---|---|---|---|---|---|---|---|---|---|
| No | M | m | n | A | B | A' | B' | E | G | J | B" | R1 | R2 | R3 | R4 | R1 | R2 |
| 590 | Ir | 2 | 1 | Ph | Iq2 | — | — | CH3 | CH3 | CH3 | — | F | F | F | H | — | — |
| 591 | Ir | 2 | 1 | Ph | Iq2 | — | — | C(CH3)3 | C(CH3)3 | H | — | F | F | F | H | — | — |
| 592 | Ir | 2 | 1 | Ph | Iq2 | — | — | CH3 | C4H9 | CH3 | — | F | F | F | H | — | — |
| 593 | Ir | 2 | 1 | Ph | Iq2 | — | — | — | — | — | Pr | F | F | F | H | — | — |
| 594 | Ir | 2 | 1 | Ph | Iq2 | — | — | — | — | — | Pr | F | F | F | H | — | — |
| 595 | Ir | 2 | 1 | Ph | Iq2 | — | — | — | — | — | Iq2 | F | F | F | H | — | — |
| 596 | Ir | 3 | 0 | Ph | Iq2 | — | — | — | — | — | — | F | H | F | H | — | — |
| 597 | Ir | 3 | 0 | Ph | Iq2 | — | — | — | — | — | — | F | H | F | H | — | — |
| 598 | Ir | 3 | 0 | Ph | Iq2 | — | — | — | — | — | — | F | H | F | H | — | — |

TABLE 17-continued

| No | M | m | n | A | B | A' | B' | B'' | R1 | R2 | R3 | R4 | R1 | R2 | R3 | R4 | R5 |
|---|---|---|---|---|---|---|---|---|---|---|---|---|---|---|---|---|---|
| 599 | Ir | 2 | 1 | Ph | Iq2 | Ph | Pr | — | — | — | — | F | H | F | H | H | H |
| 600 | Ir | 2 | 1 | Ph | Iq2 | — | — | CH3 | CH3 | H | — | F | H | F | H | — | — |
| 601 | Ir | 2 | 1 | Ph | Iq2 | — | — | CH3 | CH3 | CH3 | — | F | H | F | H | — | — |
| 602 | Ir | 2 | 1 | Ph | Iq2 | — | — | C(CH3)3 | C(CH3)3 | H | — | F | H | F | H | — | — |
| 603 | Ir | 2 | 1 | Ph | Iq2 | — | — | CH3 | C4H9 | CH3 | — | F | H | F | H | — | — |
| 604 | Ir | 2 | 1 | Ph | Iq2 | — | — | — | — | — | Pr | F | H | F | H | — | — |
| 605 | Ir | 2 | 1 | Ph | Iq2 | — | — | — | — | — | Pr | F | H | F | H | — | — |
| 606 | Ir | 2 | 1 | Ph | Iq2 | — | — | — | — | — | Iq2 | F | H | F | H | — | — |
| 607 | Ir | 3 | 0 | Ph | Iq2 | — | — | — | — | — | — | H | CF3 | H | H | — | — |
| 608 | Ir | 3 | 0 | Ph | Iq2 | — | — | — | — | — | — | H | F | H | H | — | — |
| 609 | Ir | 3 | 0 | Ph | Iq5 | — | — | — | — | — | — | H | H | H | H | — | — |
| 610 | Ir | 3 | 0 | Ph | Iq5 | — | — | — | — | — | — | H | H | H | H | — | — |
| 611 | Ir | 2 | 1 | Ph | Iq5 | Ph | Pr | — | — | — | — | H | H | H | H | H | H |
| 612 | Ir | 2 | 1 | Ph | Iq5 | — | — | CH3 | CH3 | H | — | H | H | H | H | — | — |
| 613 | Ir | 2 | 1 | Ph | Iq5 | — | — | CH3 | CH3 | CH3 | — | H | H | H | H | — | — |
| 614 | Ir | 2 | 1 | Ph | Iq5 | — | — | C(CH3)3 | C(CH3)3 | H | — | H | H | H | H | — | — |
| 615 | Ir | 2 | 1 | Ph | Iq5 | — | — | CH3 | C4H9 | CH3 | — | H | H | H | H | — | — |
| 616 | Ir | 2 | 1 | Ph | Iq5 | — | — | — | — | — | Pr | H | H | H | H | — | — |
| 617 | Ir | 2 | 1 | Ph | Iq5 | — | — | — | — | — | Pr | H | H | H | H | — | — |
| 618 | Ir | 2 | 1 | Ph | Iq5 | — | — | — | — | — | Iq2 | H | H | H | H | H | H |
| 619 | Ir | 2 | 1 | Ph | Iq2 | Ph | Pi | — | — | — | — | H | H | H | H | H | H |

| | A' | | B | | | | | B' | | | | B'' | | | | | |
|---|---|---|---|---|---|---|---|---|---|---|---|---|---|---|---|---|---|
| No | R3 | R4 | R5 | R6 | R7 | R8 | R9 | R10 | R5 | R6 | R7 | R8 | R5 | R6 | R7 | R8 | R9 | R10 |
| 590 | — | — | H | H | H | H | H | H | — | — | — | — | — | — | — | — | — | — |
| 591 | — | — | H | H | H | H | H | H | — | — | — | — | — | — | — | — | — | — |
| 592 | — | — | H | H | H | H | H | H | — | — | — | — | — | — | — | — | — | — |
| 593 | — | — | H | H | H | H | H | H | — | — | — | — | H | H | H | H | — | — |
| 594 | — | — | H | H | H | H | H | H | — | — | — | — | H | H | C4H9 | H | — | — |
| 595 | — | — | H | H | H | H | H | H | — | — | — | — | H | H | H | H | H | H |
| 596 | — | — | H | H | H | H | CF3 | H | — | — | — | — | — | — | — | — | — | — |
| 597 | — | — | H | H | H | F | CF3 | H | — | — | — | — | — | — | — | — | — | — |
| 598 | — | — | H | H | H | H | CF3 | H | — | — | — | — | — | — | — | — | — | — |
| 599 | H | H | H | H | H | H | CF3 | H | H | H | H | H | — | — | — | — | — | — |
| 600 | — | — | H | H | H | H | CF3 | H | — | — | — | — | — | — | — | — | — | — |
| 601 | — | — | H | H | H | H | CF3 | H | — | — | — | — | — | — | — | — | — | — |
| 602 | — | — | H | H | H | H | CF3 | H | — | — | — | — | — | — | — | — | — | — |
| 603 | — | — | H | H | H | H | CF3 | H | — | — | — | — | — | — | — | — | — | — |
| 604 | — | — | H | H | H | H | CF3 | H | — | — | — | — | H | H | H | H | — | — |
| 605 | — | — | H | H | H | H | CF3 | H | — | — | — | — | H | H | CH3 | H | — | — |
| 606 | — | — | H | H | H | H | CF3 | H | — | — | — | — | H | H | H | H | H | H |
| 607 | — | — | H | H | H | H | H | H | — | — | — | — | — | — | — | — | — | — |
| 608 | — | — | H | H | H | H | H | H | — | — | — | — | — | — | — | — | — | — |
| 609 | — | — | — | H | H | H | H | H | — | — | — | — | — | — | — | — | — | — |
| 610 | — | — | — | H | H | H | H | H | — | — | — | — | — | — | — | — | — | — |
| 611 | H | H | — | H | H | H | H | H | H | H | H | H | — | — | — | — | — | — |
| 612 | — | — | — | H | H | H | H | H | — | — | — | — | — | — | — | — | — | — |
| 613 | — | — | — | H | H | H | H | H | — | — | — | — | — | — | — | — | — | — |
| 614 | — | — | — | H | H | H | H | H | — | — | — | — | — | — | — | — | — | — |
| 615 | — | — | — | H | H | F | H | H | — | — | — | — | — | — | — | — | — | — |
| 616 | — | — | — | H | H | H | H | H | — | — | — | — | H | H | H | H | — | — |
| 617 | — | — | — | H | H | H | H | H | — | — | — | — | H | H | CH3 | H | — | — |
| 618 | H | H | — | H | H | H | H | H | — | — | — | — | H | H | H | H | H | H |
| 619 | H | H | H | H | H | H | H | H | H | H | H | — | — | — | — | — | — | — |

TABLE 18

| | | | | | | | | | A | | | | A' | | | | B |
|---|---|---|---|---|---|---|---|---|---|---|---|---|---|---|---|---|---|
| No | M | m | n | A | B | A' | B' | B'' | R1 | R2 | R3 | R4 | R1 | R2 | R3 | R4 | R5 |
| 620 | Ir | 2 | 1 | Ph | Iq2 | Ph | Py1 | — | H | H | H | H | H | H | H | H | H |
| 621 | Ir | 2 | 1 | Ph | Iq2 | Ph | Py2 | — | H | H | H | H | H | H | H | H | H |
| 622 | Ir | 2 | 1 | Ph | Iq2 | Ph | Pz | — | H | CF3 | H | H | H | H | H | H | H |
| 623 | Ir | 2 | 1 | Ph | Iq2 | Ph | Qn3 | — | H | H | H | H | H | H | H | H | H |
| 624 | Ir | 2 | 1 | Ph | Iq2 | Ph | Xa | — | H | H | H | H | H | H | H | H | H |
| 625 | Ir | 2 | 1 | Ph | Iq2 | Ph | Bz | — | H | H | H | H | H | H | H | H | H |
| 626 | Ir | 2 | 1 | Ph | Iq2 | Ph | Bo | — | H | H | H | H | H | H | H | H | H |
| 627 | Ir | 2 | 1 | Ph | Iq2 | Ph | Oz | — | H | H | H | H | H | H | H | H | H |
| 628 | Ir | 2 | 1 | Ph | Iq2 | Ph | Sz | — | H | H | H | H | H | H | H | H | H |
| 629 | Ir | 2 | 1 | Tn4 | Iq2 | Ph | Pr | — | H | — | — | — | H | H | H | H | H |
| 630 | Ir | 2 | 1 | Ph | Iq2 | — | — | Pr | H | H | H | H | H | — | — | — | H |
| 631 | Ir | 2 | 1 | Ph | Iq2 | — | — | Pr | H | H | H | H | H | — | — | — | H |
| 632 | Ir | 2 | 1 | Ph | Iq2 | — | — | Iq2 | H | H | H | H | H | — | — | — | H |

TABLE 18-continued

| | | | | | | | | | | | | | | | | | |
|---|---|---|---|---|---|---|---|---|---|---|---|---|---|---|---|---|---|
| 633 | Rh | 3 | 0 | Ph | Iq2 | — | — | — | F | H | F | H | — | — | — | — | H |
| 634 | Rh | 3 | 0 | Ph | Iq2 | — | — | — | F | H | F | H | — | — | — | — | H |
| 635 | Rh | 3 | 0 | Ph | Iq2 | — | — | — | F | H | F | H | — | — | — | — | H |
| 636 | Rh | 2 | 1 | Ph | Iq2 | Ph | Pr | — | F | H | F | H | H | H | H | H | H |
| 637 | Pt | 2 | 0 | Ph | Iq2 | — | — | — | F | H | F | H | — | — | — | — | H |
| 638 | Pt | 2 | 0 | Ph | Iq2 | — | — | — | F | H | F | H | — | — | — | — | H |
| 639 | Pd | 2 | 0 | Ph | Iq2 | — | — | — | F | H | F | H | — | — | — | — | H |
| 640 | Ir | 3 | 0 | Ph | Iq6 | — | — | — | H | H | H | H | — | — | — | — | H |
| 641 | Ir | 3 | 0 | Ph | Iq6 | — | — | — | H | H | F | H | — | — | — | — | H |
| 642 | Ir | 3 | 0 | Ph | Iq6 | — | — | — | F | H | F | H | — | — | — | — | H |
| 643 | Ir | 3 | 0 | Ph | Iq6 | — | — | — | H | CF3 | H | H | — | — | — | — | H |
| 644 | Ir | 3 | 0 | Ph | Iq6 | — | — | — | H | CH3 | H | H | — | — | — | — | H |
| 645 | Ir | 3 | 0 | Ph | Iq6 | — | — | — | H | C4H9 | H | H | — | — | — | — | H |
| 646 | Ir | 3 | 0 | Ph | Iq6 | — | — | — | H | C3F7 | H | H | — | — | — | — | H |
| 647 | Ir | 3 | 0 | Ph | Iq6 | — | — | — | H | OC6H13 | C3H7 | H | — | — | — | — | H |
| 648 | Ir | 3 | 0 | Ph | Iq6 | — | — | — | F | F | F | H | — | — | — | — | H |
| 649 | Ir | 3 | 0 | Ph | Iq6 | — | — | — | H | OCF3 | H | H | — | — | — | — | H |
| 650 | Ir | 3 | 0 | Ph | Iq7 | — | — | — | H | H | H | H | — | — | — | — | H |
| 651 | Ir | 3 | 0 | Ph | Iq7 | — | — | — | H | H | F | H | — | — | — | — | H |
| 652 | Ir | 3 | 0 | Ph | Iq7 | — | — | — | F | H | F | H | — | — | — | — | H |
| 653 | Ir | 3 | 0 | Ph | Iq7 | — | — | — | H | CF3 | H | H | — | — | — | — | H |
| 654 | Ir | 3 | 0 | Ph | Iq7 | — | — | — | H | CH3 | H | H | — | — | — | — | H |
| 655 | Ir | 3 | 0 | Ph | Iq7 | — | — | — | H | C4H9 | H | H | — | — | — | — | H |
| 656 | Ir | 3 | 0 | Ph | Iq7 | — | — | — | H | C3F7 | H | H | — | — | — | — | H |
| 657 | Ir | 3 | 0 | Ph | Iq7 | — | — | — | H | OC6H13 | C3H7 | H | — | — | — | — | H |
| 658 | Ir | 3 | 0 | Ph | Iq7 | — | — | — | F | F | F | H | — | — | — | — | H |
| 659 | Ir | 3 | 0 | Ph | Iq7 | — | — | — | H | OCF3 | H | H | — | — | — | — | H |

| | B | | | | | B' | | | | | | B'' | | | | | |
|---|---|---|---|---|---|---|---|---|---|---|---|---|---|---|---|---|---|
| No | R6 | R7 | R8 | R9 | R10 | R5 | R6 | R7 | R8 | R9 | R10 | R5 | R6 | R7 | R8 | R9 | R10 |
| 620 | H | H | H | H | H | H | H | — | H | — | — | — | — | — | — | — | — |
| 621 | H | H | H | H | H | — | H | H | H | — | — | — | — | — | — | — | — |
| 622 | H | H | H | H | H | H | — | H | H | — | — | — | — | — | — | — | — |
| 623 | H | H | H | H | H | H | H | H | H | H | H | — | — | — | — | — | — |
| 624 | H | H | H | H | H | H | — | H | H | H | H | — | — | — | — | — | — |
| 625 | H | H | H | H | H | H | H | H | H | — | — | — | — | — | — | — | — |
| 626 | H | H | H | H | H | H | H | H | H | — | — | — | — | — | — | — | — |
| 627 | H | H | H | H | H | H | H | — | — | — | — | — | — | — | — | — | — |
| 628 | H | H | H | H | H | H | H | H | — | — | — | — | — | — | — | — | — |
| 629 | H | H | H | H | H | H | H | H | H | — | — | — | — | — | — | — | — |
| 630 | H | H | H | H | H | — | — | — | — | — | — | H | H | H | H | — | — |
| 631 | H | H | H | H | H | — | — | — | — | — | — | H | H | CH3 | H | — | — |
| 632 | H | H | H | H | H | — | — | — | — | — | — | H | H | H | H | H | H |
| 633 | H | H | F | H | H | — | — | — | — | — | — | — | — | — | — | — | — |
| 634 | H | H | F | H | H | — | — | — | — | — | — | — | — | — | — | — | — |
| 635 | H | H | F | H | H | — | — | — | — | — | — | — | — | — | — | — | — |
| 636 | H | H | F | H | H | H | H | H | H | — | — | — | — | — | — | — | — |
| 637 | H | H | H | F | H | — | — | — | — | — | — | — | — | — | — | — | — |
| 638 | H | H | H | F | H | — | — | — | — | — | — | — | — | — | — | — | — |
| 639 | H | H | H | F | H | — | — | — | — | — | — | — | — | — | — | — | — |
| 640 | H | H | — | H | H | — | — | — | — | — | — | — | — | — | — | — | — |
| 641 | H | H | — | H | H | — | — | — | — | — | — | — | — | — | — | — | — |
| 642 | H | H | — | F | H | — | — | — | — | — | — | — | — | — | — | — | — |
| 643 | H | H | — | CF3 | H | — | — | — | — | — | — | — | — | — | — | — | — |
| 644 | H | H | — | H | H | — | — | — | — | — | — | — | — | — | — | — | — |
| 645 | H | H | — | H | H | — | — | — | — | — | — | — | — | — | — | — | — |
| 646 | H | H | — | H | H | — | — | — | — | — | — | — | — | — | — | — | — |
| 647 | H | H | — | H | H | — | — | — | — | — | — | — | — | — | — | — | — |
| 648 | H | H | — | CF3 | H | — | — | — | — | — | — | — | — | — | — | — | — |
| 649 | H | H | — | H | H | — | — | — | — | — | — | — | — | — | — | — | — |
| 650 | H | H | H | — | H | — | — | — | — | — | — | — | — | — | — | — | — |
| 651 | H | H | H | — | H | — | — | — | — | — | — | — | — | — | — | — | — |
| 652 | H | H | H | — | H | — | — | — | — | — | — | — | — | — | — | — | — |
| 653 | H | H | CF3 | — | H | — | — | — | — | — | — | — | — | — | — | — | — |
| 654 | H | H | H | — | H | — | — | — | — | — | — | — | — | — | — | — | — |
| 655 | H | H | H | — | H | — | — | — | — | — | — | — | — | — | — | — | — |
| 656 | H | H | H | — | H | — | — | — | — | — | — | — | — | — | — | — | — |
| 657 | H | H | H | — | H | — | — | — | — | — | — | — | — | — | — | — | — |
| 658 | H | H | F | — | H | — | — | — | — | — | — | — | — | — | — | — | — |
| 659 | H | H | H | — | H | — | — | — | — | — | — | — | — | — | — | — | — |

TABLE 19

| No | M | m' | A | B | A R1 | A R2 | A R3 | A R4 | B R5 | B R6 | B R7 | B R8 | B R9 | B R10 |
|---|---|---|---|---|---|---|---|---|---|---|---|---|---|---|
| 660 | Ir | 2 | Ph | Iq2 | H | H | H | H | H | H | H | H | H | H |
| 661 | Ir | 2 | Ph | Iq2 | H | CH3 | H | H | H | H | H | H | H | H |
| 662 | Ir | 2 | Ph | Iq2 | H | C2H5 | H | H | H | H | H | H | H | H |
| 663 | Ir | 2 | Ph | Iq2 | H | C3H7 | H | H | H | H | H | H | H | H |
| 664 | Ir | 2 | Ph | Iq2 | H | C4H9 | H | H | H | H | H | H | H | H |
| 665 | Ir | 2 | Ph | Iq2 | H | C(CH3)3 | H | H | H | H | H | H | H | H |
| 666 | Ir | 2 | Ph | Iq2 | H | C5H11 | H | H | H | H | H | H | H | H |
| 667 | Ir | 2 | Ph | Iq2 | H | C6H13 | H | H | H | H | H | H | H | H |
| 668 | Ir | 2 | Ph | Iq2 | H | C7H15 | H | H | H | H | H | H | H | H |
| 669 | Ir | 2 | Ph | Iq2 | H | C8H17 | H | H | H | H | H | H | H | H |
| 670 | Ir | 2 | Ph | Iq2 | H | C9H19 | H | H | H | H | H | H | H | H |
| 671 | Ir | 2 | Ph | Iq2 | H | C10H21 | H | H | H | H | H | H | H | H |
| 672 | Ir | 2 | Ph | Iq2 | H | C11H23 | H | H | H | H | H | H | H | H |
| 673 | Ir | 2 | Ph | Iq2 | H | C12H25 | H | H | H | H | H | H | H | H |
| 674 | Ir | 2 | Ph | Iq2 | H | C13H27 | H | H | H | H | H | H | H | H |
| 675 | Ir | 2 | Ph | Iq2 | H | C14H29 | H | H | H | H | H | H | H | H |
| 676 | Ir | 2 | Ph | Iq2 | H | C15H31 | H | H | H | H | H | H | H | H |
| 677 | Ir | 2 | Ph | Iq2 | H | C16H33 | H | H | H | H | H | H | H | H |
| 678 | Ir | 2 | Ph | Iq2 | H | C17H35 | H | H | H | H | H | H | H | H |
| 679 | Ir | 2 | Ph | Iq2 | H | C18H37 | H | H | H | H | H | H | H | H |
| 680 | Ir | 2 | Ph | Iq2 | H | C19H39 | H | H | H | H | H | H | H | H |
| 681 | Ir | 2 | Ph | Iq2 | H | C20H41 | H | H | H | H | H | H | H | H |
| 682 | Ir | 2 | Ph | Iq2 | F | H | H | H | H | H | H | H | H | H |
| 683 | Ir | 2 | Ph | Iq2 | H | F | H | H | H | H | H | H | H | H |
| 684 | Ir | 2 | Ph | Iq2 | H | H | F | H | H | H | H | H | H | H |
| 685 | Ir | 2 | Ph | Iq2 | H | H | H | F | H | H | H | H | H | H |
| 686 | Ir | 2 | Ph | Iq2 | F | H | F | H | H | H | H | H | H | H |
| 687 | Ir | 2 | Ph | Iq2 | H | F | F | H | H | H | H | H | H | H |
| 688 | Ir | 2 | Ph | Iq2 | H | F | H | F | H | H | H | H | H | H |
| 689 | Ir | 2 | Ph | Iq2 | F | F | F | H | H | H | H | H | H | H |

TABLE 20

| No | M | m' | A | B | A R1 | A R2 | A R3 | A R4 | B R5 | B R6 | B R7 | B R8 | B R9 | B R10 |
|---|---|---|---|---|---|---|---|---|---|---|---|---|---|---|
| 690 | Ir | 2 | Ph | Iq2 | F | F | F | F | H | H | H | CF3 | H | H |
| 691 | Ir | 2 | Ph | Iq2 | H | CF3 | H | H | H | H | H | H | CF3 | H |
| 692 | Ir | 2 | Ph | Iq2 | H | H | CF3 | H | H | H | H | H | CF3 | H |
| 693 | Ir | 2 | Ph | Iq2 | H | H | H | CF3 | H | H | H | H | H | H |
| 694 | Ir | 2 | Ph | Iq2 | CF3 | H | CF3 | H | H | H | H | H | CF3 | H |
| 695 | Ir | 2 | Ph | Iq2 | H | CH3 | F | F | H | H | H | H | H | H |
| 696 | Ir | 2 | Ph | Iq2 | H | C2H5 | F | F | H | H | H | H | F | H |
| 697 | Ir | 2 | Ph | Iq2 | H | C3H7 | F | F | H | H | H | H | H | H |
| 698 | Ir | 2 | Ph | Iq2 | H | C4H9 | F | F | H | H | H | H | F | H |
| 699 | Ir | 2 | Ph | Iq2 | H | C5H11 | F | F | H | H | H | H | H | H |
| 700 | Ir | 2 | Ph | Iq2 | H | C6H13 | F | F | H | H | H | H | CF3 | H |
| 701 | Ir | 2 | Ph | Iq2 | H | C12H25 | F | F | H | H | H | H | H | H |
| 702 | Ir | 2 | Ph | Iq2 | H | C15H31 | F | F | H | H | H | H | H | H |
| 703 | Ir | 2 | Ph | Iq2 | H | C20H41 | F | F | H | H | H | H | H | H |
| 704 | Ir | 2 | Ph | Iq2 | H | H | H | H | H | H | H | F | H | H |
| 705 | Ir | 2 | Ph | Iq2 | H | H | H | H | H | H | H | H | F | H |
| 706 | Ir | 2 | Ph | Iq2 | H | H | H | H | H | H | H | CF3 | H | H |
| 707 | Ir | 2 | Ph | Iq2 | H | H | H | H | H | H | H | H | CF3 | H |
| 708 | Ir | 2 | Ph | Iq2 | H | H | H | H | F | F | F | F | F | F |
| 709 | Ir | 2 | Ph | Iq2 | F | F | F | F | F | F | F | F | F | F |
| 710 | Ir | 2 | Ph | Iq2 | H | CF3 | H | H | H | H | H | F | H | H |
| 711 | Ir | 2 | Ph | Iq2 | H | C2F5 | H | H | H | H | H | H | H | H |
| 712 | Ir | 2 | Ph | Iq2 | H | C3F7 | H | H | H | H | H | H | H | H |
| 713 | Ir | 2 | Ph | Iq2 | H | C4F9 | H | H | H | H | H | H | CF3 | H |
| 714 | Ir | 2 | Ph | Iq2 | H | C5F11 | H | H | H | H | H | H | H | H |
| 715 | Ir | 2 | Ph | Iq2 | H | C6F13 | H | H | H | H | H | H | H | H |
| 716 | Ir | 2 | Ph | Iq2 | H | C7F15 | H | H | H | H | H | H | CF3 | H |
| 717 | Ir | 2 | Ph | Iq2 | H | C8F17 | H | H | H | H | H | H | H | H |
| 718 | Ir | 2 | Ph | Iq2 | H | C10F21 | H | H | H | H | H | H | H | H |
| 719 | Ir | 2 | Ph | Iq2 | H | C15F31 | H | H | H | H | H | H | H | H |

TABLE 21

| No | M | m' | A | B | R1 | R2 (A) | R3 (A) | R4 | R5 (B) | R6 | R7 | R8 | R9 | R10 |
|---|---|---|---|---|---|---|---|---|---|---|---|---|---|---|
| 720 | Ir | 2 | Ph | Iq2 | H | 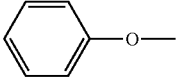 | H | H | H | H | H | H | H | H |
| 721 | Ir | 2 | Ph | Iq2 | H | H | CH3 | H | H | H | H | H | H | H |
| 722 | Ir | 2 | Ph | Iq2 | H | H | 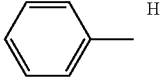 | H | H | H | H | H | H | H |
| 723 | Ir | 2 | Ph | Iq2 | H | H | C2H5 | H | H | H | H | H | H | H |
| 724 | Ir | 2 | Ph | Iq2 | H | H | C3H7 | H | H | H | H | H | H | H |
| 725 | Ir | 2 | Ph | Iq2 | H | H | C4H9 | H | H | H | H | H | H | H |
| 726 | Ir | 2 | Ph | Iq2 | H | H | C(CH3)3 | H | H | H | H | H | H | H |
| 727 | Ir | 2 | Ph | Iq2 | H | H | C5H11 | H | H | H | H | H | H | H |
| 728 | Ir | 2 | Ph | Iq2 | H | H | C6H13 | H | H | H | H | H | H | H |
| 729 | Ir | 2 | Ph | Iq2 | H | H | C7H15 | H | H | H | H | H | H | H |
| 730 | Ir | 2 | Ph | Iq2 | H | H | C8H17 | H | H | H | H | H | H | H |
| 731 | Ir | 2 | Ph | Iq2 | H | H | C9H19 | H | H | H | H | H | H | H |
| 732 | Ir | 2 | Ph | Iq2 | H | H | C10H21 | H | H | H | H | H | H | H |
| 733 | Ir | 2 | Ph | Iq2 | H | H | C11H23 | H | H | H | H | H | H | H |
| 734 | Ir | 2 | Ph | Iq2 | H | H | C12H25 | H | H | H | H | H | H | H |
| 735 | Ir | 2 | Ph | Iq2 | H | H | C15H31 | H | H | H | H | H | H | H |
| 736 | Ir | 2 | Ph | Iq2 | H | H | C18H37 | H | H | H | H | H | H | H |
| 737 | Ir | 2 | Ph | Iq2 | H | H | C20H41 | H | H | H | H | H | H | H |
| 738 | Ir | 2 | Ph | Iq2 | H | F | CH3 | H | H | H | H | H | H | H |
| 739 | Ir | 2 | Fl | Iq2 | H | H | — | — | H | H | H | H | H | H |
| 740 | Ir | 2 | Tn1 | Iq2 | H | H | — | — | H | H | H | H | H | H |
| 741 | Ir | 2 | Tn2 | Iq2 | H | H | — | — | H | H | H | H | H | H |
| 742 | Ir | 2 | Tn3 | Iq2 | H | H | — | — | H | H | H | H | H | H |
| 743 | Ir | 2 | Tn4 | Iq2 | H | H | — | — | H | H | H | H | H | H |
| 744 | Ir | 2 | Np1 | Iq2 | H | H | — | — | H | H | H | H | H | H |
| 745 | Ir | 2 | Np2 | Iq2 | H | H | — | — | H | H | H | H | H | H |
| 746 | Ir | 2 | Cn1 | Iq2 | H | H | — | — | H | H | H | H | H | H |
| 747 | Ir | 2 | Cn2 | Iq2 | H | H | — | — | H | H | H | H | H | H |
| 748 | Ir | 2 | Pe | Iq2 | H | H | — | — | H | H | H | H | H | H |
| 749 | Ir | 2 | Qn1 | Iq2 | H | H | — | — | H | H | H | H | H | H |
| 750 | Ir | 2 | Qn2 | Iq2 | H | H | — | — | H | H | H | H | H | H |

TABLE 22

| No | M | m' | A | B | R1 | R2 (A) | R3 (A) | R4 (A) | R5 (B) | R6 | R7 | R8 | R9 | R10 |
|---|---|---|---|---|---|---|---|---|---|---|---|---|---|---|
| 751 | Ir | 2 | Cz | Iq2 | H | C2H5 | — | — | H | H | H | H | H | H |
| 752 | Ir | 2 | Ph | Iq5 | H | H | CF3 | H | — | H | H | H | H | H |
| 753 | Ir | 2 | Ph | Iq5 | H | H | H | CF3 | — | H | H | H | H | H |
| 754 | Ir | 2 | Ph | Iq5 | CF3 | H | CF3 | H | — | H | H | H | H | H |
| 755 | Ir | 2 | Ph | Iq5 | H | H | H | H | — | H | H | H | H | H |
| 756 | Ir | 2 | Ph | Iq5 | H | CH3 | F | F | — | H | H | H | H | H |
| 757 | Ir | 2 | Ph | Iq5 | H | C2H5 | F | F | — | H | H | H | H | H |
| 758 | Ir | 2 | Ph | Iq5 | H | C3H7 | F | F | — | H | H | H | H | H |
| 759 | Ir | 2 | Ph | Iq5 | H | C4H9 | F | F | — | H | H | H | H | H |
| 760 | Ir | 2 | Ph | Iq5 | H | C5H11 | F | F | — | H | H | H | H | H |
| 761 | Ir | 2 | Ph | Iq5 | H | C6H13 | F | F | — | H | H | H | H | H |
| 762 | Ir | 2 | Ph | Iq5 | H | C6F13 | H | H | — | H | H | H | H | H |
| 763 | Ir | 2 | Ph | Iq6 | H | H | H | H | H | H | H | — | H | H |
| 764 | Ir | 2 | Ph | Iq6 | H | H | F | H | H | H | H | — | H | H |
| 765 | Ir | 2 | Ph | Iq6 | F | H | F | H | H | H | H | — | F | H |
| 766 | Ir | 2 | Ph | Iq6 | H | CF3 | H | H | H | H | H | — | CF3 | H |
| 767 | Ir | 2 | Ph | Iq6 | H | CH3 | H | H | H | H | H | — | H | H |
| 768 | Ir | 2 | Ph | Iq6 | H | C4H9 | H | H | H | H | H | — | H | H |
| 769 | Ir | 2 | Ph | Iq6 | H | C3F7 | H | H | H | H | H | — | H | H |
| 770 | Ir | 2 | Ph | Iq6 | H | OC6H13 | C3H7 | H | H | H | H | — | H | H |
| 771 | Ir | 2 | Ph | Iq6 | F | F | F | H | H | H | H | — | CF3 | H |
| 772 | Ir | 2 | Ph | Iq6 | H | OCF3 | H | H | H | H | H | — | H | H |
| 773 | Ir | 2 | Ph | Iq7 | H | H | H | H | H | H | H | H | — | H |
| 774 | Ir | 2 | Ph | Iq7 | H | H | F | H | H | H | H | H | — | H |
| 775 | Ir | 2 | Ph | Iq7 | F | H | F | H | H | H | H | H | — | H |

TABLE 22-continued

| | | | | | | A | | | | B | | | | | |
|---|---|---|---|---|---|---|---|---|---|---|---|---|---|---|---|
| No | M | m' | A | B | R1 | R2 | R3 | R4 | R5 | R6 | R7 | R8 | R9 | R10 |
| 776 | Ir | 2 | Ph | Iq7 | H | CF3 | H | H | H | H | H | CF3 | — | H |
| 777 | Ir | 2 | Ph | Iq7 | H | CH3 | H | H | H | H | H | H | — | H |
| 778 | Ir | 2 | Ph | Iq7 | H | C4H9 | H | H | H | H | H | H | — | H |
| 779 | Ir | 2 | Ph | Iq7 | H | C3F7 | H | H | H | H | H | H | — | H |
| 780 | Ir | 2 | Ph | Iq7 | H | OC6H13 | C3H7 | H | H | H | H | H | — | H |
| 781 | Ir | 2 | Ph | Iq7 | F | F | F | H | H | H | H | F | — | H |
| 782 | Ir | 2 | Ph | Iq7 | H | OCF3 | H | H | H | H | H | H | — | H |

TABLE 23

| | | | | | | A | | | | B | | | | | |
|---|---|---|---|---|---|---|---|---|---|---|---|---|---|---|---|
| No | M | m | n | A | B | R1 | R2 | R3 | R4 | R5 | R6 | R7 | R8 | R9 | R10 |
| 783 | Ir | 3 | 0 | Ph | Iq8 | H | H | H | H | H | — | H | H | H | H |
| 784 | Ir | 3 | 0 | Ph | Iq8 | H | H | F | H | H | — | H | H | H | H |
| 785 | Ir | 3 | 0 | Ph | Iq8 | F | H | F | H | H | — | H | H | F | H |
| 786 | Ir | 3 | 0 | Ph | Iq8 | H | CF3 | H | H | H | — | H | H | CF3 | H |
| 787 | Ir | 3 | 0 | Ph | Iq8 | H | CH3 | H | H | H | — | H | H | H | H |
| 788 | Ir | 3 | 0 | Ph | Iq8 | H | C4H9 | H | H | H | — | H | H | H | H |
| 789 | Ir | 3 | 0 | Ph | Iq8 | H | C3F7 | H | H | H | — | H | H | H | H |
| 790 | Ir | 3 | 0 | Ph | Iq8 | H | OC6H13 | C3H7 | H | H | — | H | H | H | H |
| 791 | Ir | 3 | 0 | Ph | Iq8 | F | F | F | H | H | — | H | H | CF3 | H |
| 792 | Ir | 3 | 0 | Ph | Iq8 | H | OCF3 | H | H | H | — | H | H | H | H |
| 793 | Ir | 3 | 0 | Ph | Iq9 | H | H | H | H | H | H | — | H | H | H |
| 794 | Ir | 3 | 0 | Ph | Iq9 | H | H | F | H | H | H | — | H | H | H |
| 795 | Ir | 3 | 0 | Ph | Iq9 | F | H | F | H | H | H | — | H | F | H |
| 796 | Ir | 3 | 0 | Ph | Iq9 | H | CF3 | H | H | H | H | — | H | CF3 | H |
| 797 | Ir | 3 | 0 | Ph | Iq9 | H | CH3 | H | H | H | H | — | H | H | H |
| 798 | Ir | 3 | 0 | Ph | Iq9 | H | C4H9 | H | H | H | H | — | H | H | H |
| 799 | Ir | 3 | 0 | Ph | Iq9 | H | C3F7 | H | H | H | H | — | H | H | H |
| 800 | Ir | 3 | 0 | Ph | Iq9 | H | OC6H13 | C3H7 | H | H | H | — | H | H | H |
| 801 | Ir | 3 | 0 | Ph | Iq9 | F | F | F | H | H | H | — | H | CF3 | H |
| 802 | Ir | 3 | 0 | Ph | Iq9 | H | OCF3 | H | H | H | H | — | H | H | H |
| 803 | Ir | 3 | 0 | Ph | Iq10 | H | H | H | H | H | H | H | H | H | — |
| 804 | Ir | 3 | 0 | Ph | Iq10 | H | H | F | H | H | H | H | H | H | — |
| 805 | Ir | 3 | 0 | Ph | Iq10 | F | H | F | H | H | H | H | H | F | — |
| 806 | Ir | 3 | 0 | Ph | Iq10 | H | CF3 | H | H | H | H | H | H | CF3 | — |
| 807 | Ir | 3 | 0 | Ph | Iq10 | H | CH3 | H | H | H | H | H | H | H | — |
| 808 | Ir | 3 | 0 | Ph | Iq10 | H | C4H9 | H | H | H | H | H | H | H | — |
| 809 | Ir | 3 | 0 | Ph | Iq10 | H | C3F7 | H | H | H | H | H | H | H | — |
| 810 | Ir | 3 | 0 | Ph | Iq10 | H | OC6H13 | C3H7 | H | H | H | H | H | H | — |
| 811 | Ir | 3 | 0 | Ph | Iq10 | F | F | F | H | H | H | H | H | CF3 | — |
| 812 | Ir | 3 | 0 | Ph | Iq10 | H | OCF3 | H | H | H | H | H | H | H | — |

EXAMPLES

Hereinbelow, the present invention will be described more specifically based on Examples.

Examples 1 and 2

In these Examples, a device (effective display area=3 mm$^2$) having a device structure including 4 organic layers as shown in FIG. 1(c) was prepared. An alkali-free glass sheet was used as a transparent substrate 15 and a 100 nm-thick indium oxide (ITO) film was formed by sputtering and patterned as a transparent electrode 14. Further, α-NPD represented by the above-mentioned structural formula was vacuum-deposited in a layer thickness of 40 nm thereon as a hole-transporting layer 13. Then, as an organic luminescence layer 12, the above-mentioned CBP as a host material and a prescribed metal coordination compound in an amount of providing 8 wt. % were co-vacuum deposited in a layer thickness of 30 nm. Further, as an exciton diffusion-prevention layer 17. BCP was vacuum-deposited in a thickness of 10 nm. Then, as an electron-transporting layer 16, the above-mentioned Alq3 was subjected to resistance heating vacuum deposition at a vacuum of $10^{-4}$ Pa to form an organic film in a thickness of 30 nm.

On the above, as a lower layer of a metal electrode layer 11, an AlLi alloy film was disposed in a thickness of 15 nm, and a 100 nm-thick Al film was vacuum-deposited thereon to form a patterned metal electrode 11 disposed opposite to the transparent electrode 14 and having an electrode area of 3 mm$^2$.

As the ligands, Example Compound No. 1 (Example 1) and Example Compound No. 28 (Example 2) shown in Table 1 were used respectively.

The performances of the thus-obtained EL devices were measured by using a micro-current meter ("4140B", made by Hewlett-Packard Corp.) for a current-voltage characteristic and "BM7" (made by Topcon K.K.) for an emission luminance. The devices using the respective coordination compounds respectively exhibited a good rectifying characteristic.

At an applied voltage of 12 volts, the EL devices exhibited luminances as follows:

Device of Example 1 (Compound No. 1): 8000 cd/m$^2$

Device of Example 2 (Compound No. 28): 3500 cd/m$^2$

For examining luminescence characteristics of the Coordinate Compounds No. 1 and No. 28, the solutions were subjected to measurement of a luminescence spectrum. More specifically, each solution having a coordination compound concentration of $10^{-4}$ mol/l in toluene (or chloroform) was illuminated with excitation light of around 350 nm to measure a luminescence spectrum by using a spectral fluorophotometer ("F4500", made by Hitachi K.K.). The luminescence spectra almost coincided with the spectra from the EL devices at the time of voltage application, whereby it was confirmed that the luminescences of the EL devices were emitted from the coordination compounds. (Refer to Example 7 and 8 described hereinafter.)

Examples 3-5, Comparative Example 1

Luminescence devices were prepared in the same manner as in Examples 1 and 2 except for using luminescence materials (Example Compounds) shown in Table 24 below. In Comparative Example 1, the above-mentioned Ir(ppy)$_3$ was used as a representative of conventional luminescence material.

A current conduction durability test was performed for each device by applying a DC voltage of 12 volts between the ITO electrode as the anode and the Al electrode as the cathode to measure a time within which the luminance was attenuated to a half.

The measurement results are shown in Table 24 and the Example materials exhibited a luminance half-attenuation period which was clearly longer than the conventional luminescence material, thus providing a device having a high durability attributable to the material of the present invention.

TABLE 24

| Example | Luminescence material No. | Luminance half-attenuation period (hours) |
| --- | --- | --- |
| 3 | 1 | 1550 |
| 4 | 24 | 1100 |
| 5 | 28 | 1350 |
| Comp. 1 | Ir(ppy)$_3$ | 350 |

Example 6

A simple matrix type organic EL device as shown in FIG. 2 was prepared in the following manner.

On a glass substrate 21 measuring 100 mm-length, 100 mm-width and 1.1 mm-thickness, a ca. 100 nm-thick ITO film was formed by sputtering and patterned into 100 lines of 100 μm-wide transparent electrodes 22 (anode side) with a spacing of 40 μm as simple matrix electrodes. Then, formed layers of identical organic materials were found under identical conditions as in Example 1 to form an organic compound layer 23.

Then, 100 lines of 100 μm-wide Al electrodes 24 were formed with a spacing of 40 μm by mask vacuum deposition so as to be perpendicular to the transparent electrodes 22 by vacuum deposition at a vacuum of $2.7 \times 10^{-3}$ Pa. The metal electrodes (cathode) 24 were formed as a lamination of 10 nm-thick layer of Al/Li alloy (Li: 1.3 wt. %) and then 150 nm-thick layer of Al.

The thus-obtained 100×100-simple matrix-type organic EL device was subjected to a simple matrix drive in a glove box filled with nitrogen at voltages of 7 volts to 13 volts by using a scanning signal of 10 volts and data signals of ±3 volts. As a result of an interlaced drive at a frame efficiency of 30 Hz, respectively, luminescence images could be confirmed.

Example 7

Synthesis of Example Compound No. 1

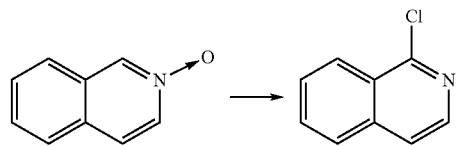

69.3 g (448 mmol) of isoquinoline N-oxide (made by Tokyo Kasei) and 225 ml of chloroform were placed and dissolved in a 1 liter-three-necked flask, and under stirring and cooling with ice, 219.6 g (1432 mmol) of phosphorus oxychloride was gradually added dropwise thereto while the internal temperature was held at 15-20° C. Thereafter, the temperature was raised, and reflux under stirring was performed for 3 hours. The reaction product was cooled by standing to room temperature and poured into iced water. After extraction with ethyl acetate, the organic layer washed with water until neutrality, and the solvent was removed under a reduced pressure to provide a dry solid, which was then purified by silica gel column chromatography (eluent: chloroform/hexane=5/1) to obtain 35 5 g (yield: 44.9%) of 1-chloroisoquinoline white crystal.

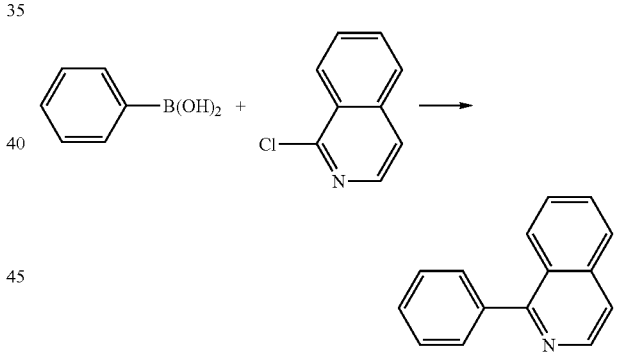

Figure 7:
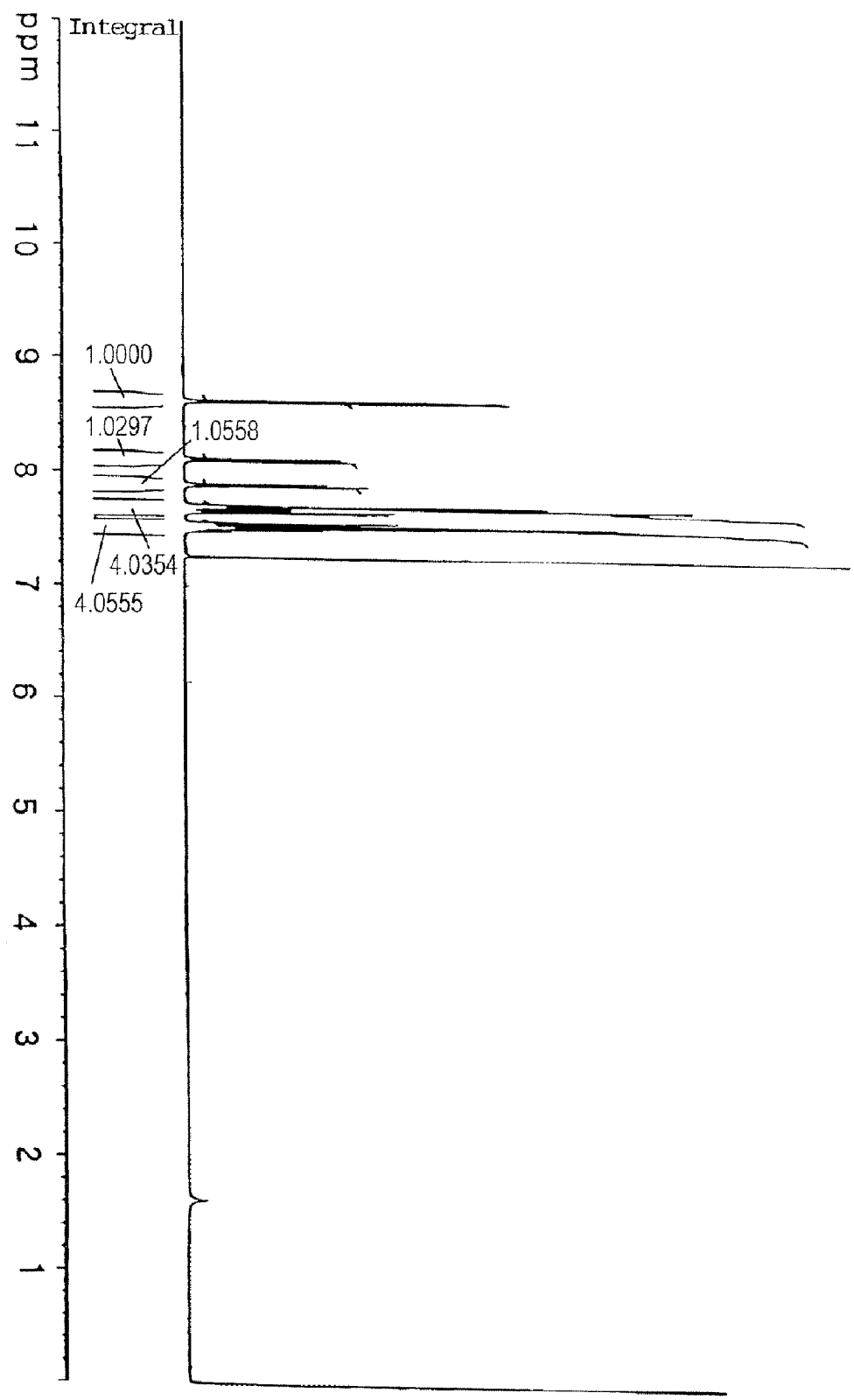
FIG. 7 shows a $^1$H-NMR spectrum of a solution in heavy chloroform of 1-phenylisoquinoline.

In a 100 ml-three-necked flask, 3.04 g (24.9 mmole) of phenylboronic acid (made by Tokyo Kasei), 4.0 g of (25.0 mmole) of 1-chloroisoquinoline, 25 ml of toluene, 12.5 ml of ethanol and 25 ml of 2M-sodium carbonate aqueous solution were placed and stirred at room temperature under nitrogen stream, and 0.98 g (0.85 mmole) of tetrakis(triphenylphosphine)palladium (0) was added thereto. Thereafter, reflux under stirring was performed for 8 hours under nitrogen stream. After completion of the reaction, the reaction product was cooled and extracted by addition of cold water and toluene. The organic layer was washed with saline water and dried on magnesium sulfate, followed by removal of the solvent under a reduced pressure to provide dry solid. The residue was purified by silica gel column chromatography (eluent: chloroform/methanol 10/1) to obtain 2.20 g (yield=43.0%) of 1-phenylisoquinoline. FIG. 7 shows a $^1$H-NMR spectrum of a solution of the compound in heavy chloroform.

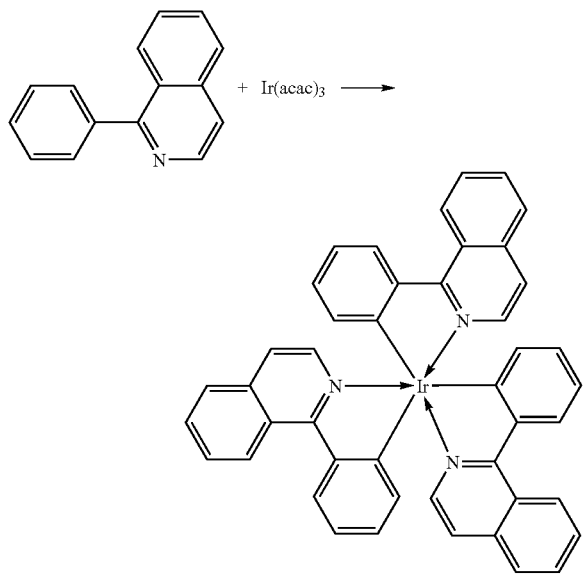

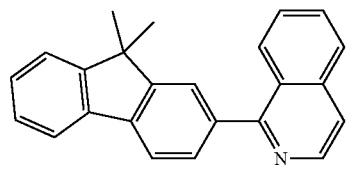

In a 100 ml-four-necked flask, 50 ml of glycerol was placed and heated at 130-140° C. under stirring and bubbling with nitrogen for 2 hours. Then, the glycerol was cooled by standing down to 100° C., and 1.03 g (5.02 mmole) of 1-phenylisoquinoline and 0.50 g (1.02 mmole) of iridium (III) acetylacetonate (made by Strem Chemicals, Inc.) were added, followed by 7 hours of heating-around ±210° C. under stirring and nitrogen stream. The reaction product was cooled to room temperature and injected into 300 ml of 1N-hydrochloric acid to form a precipitate, which was filtered out and washed with water. The precipitate was purified by silica gel column chromatography with chloroform as the eluent to obtain 0 22 g (yield=26.8%) of red powdery tris(1-phenylisoquinoline-C$^2$,N)iridium (III). According to MALDI-TOF MS (matrix-assisted laser desorption ionization-time of fight mass spectroscopy), the compound exhibited M$^+$ (mass number of the corresponding cation formed by removal of 1 electron) of 805.2.

Figure 8:
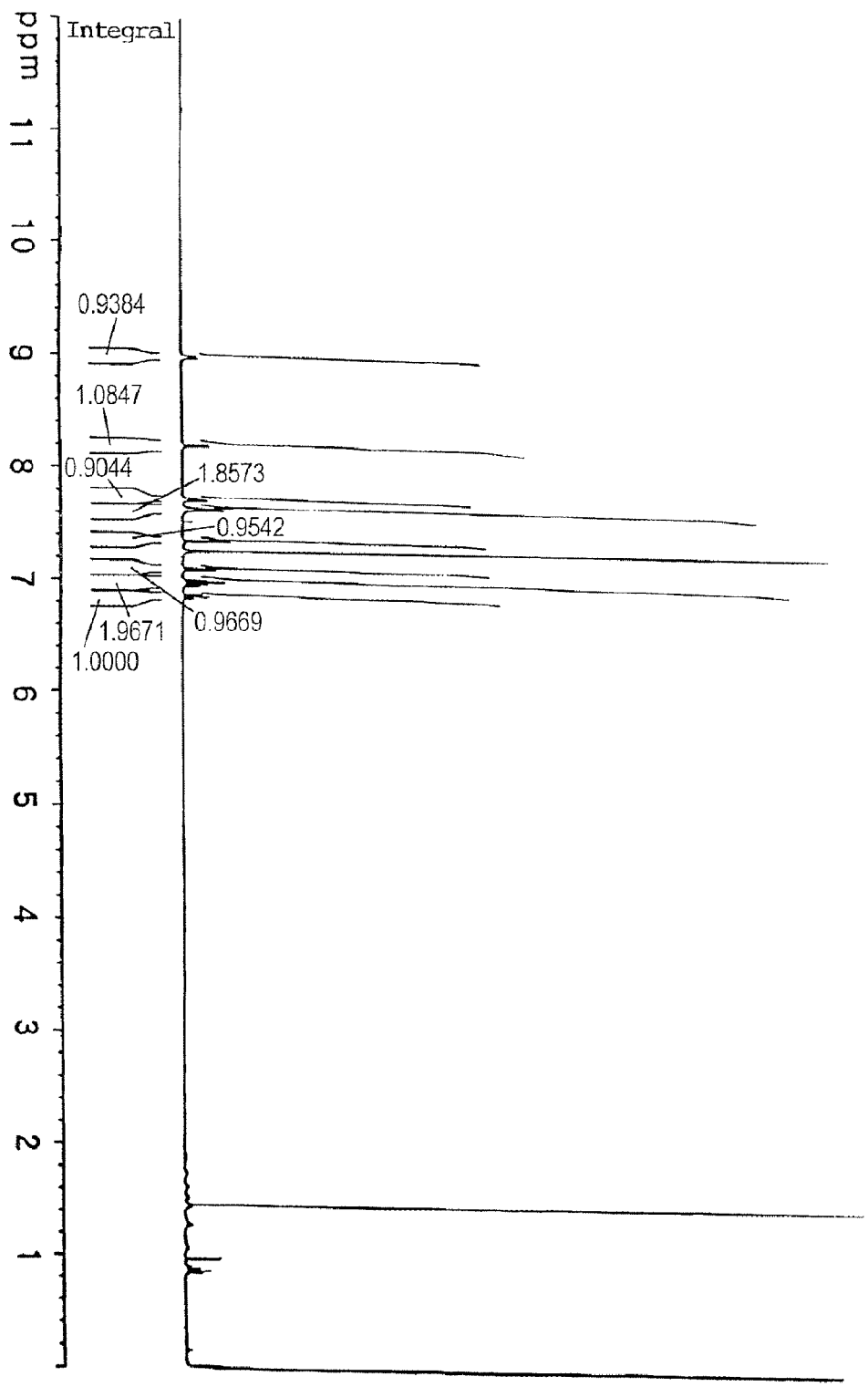
FIG. 8 shows a $^1$H-NMR spectrum of a solution in heavy chloroform of tris(1-phenyl-isoquinoline-$C^2$,N)iridium (III).
Figure 9:
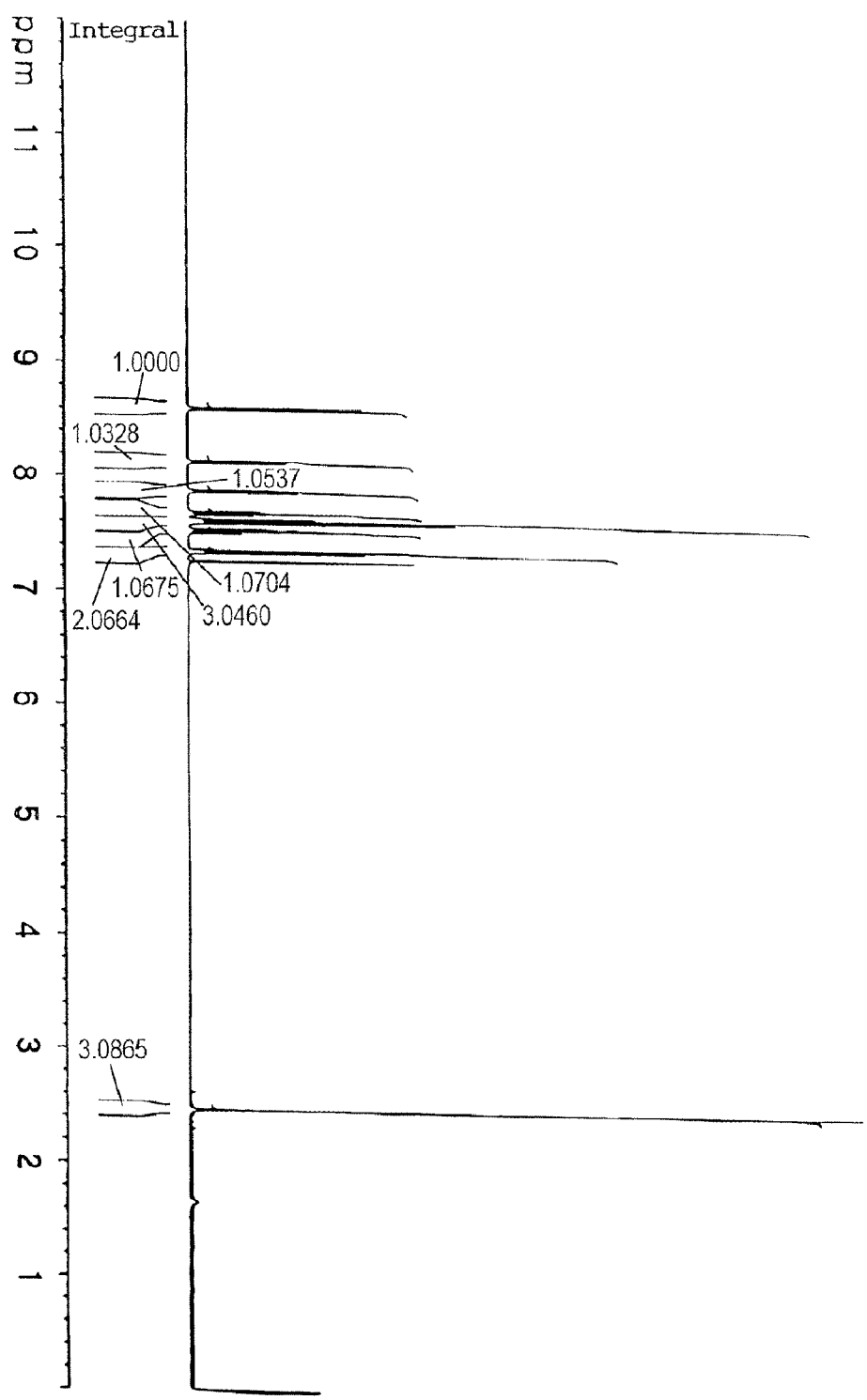
FIG. 9 shows a $^1$H-NMR spectrum of a solution in heavy chloroform of 1-(4-methylphenyl)-isoquinoline.

A solution in heavy chloroform of the compound provided a $^1$H-NMR spectrum as shown in FIG. 8. A chloroform solution of the compound exhibited a luminescence spectrum showing λmax=619 nm and a quantum yield of 0.66 relative to 1.0 of Ir(ppy)$_3$.

An EL device of Example 1 prepared by using the compound exhibited red luminescence showing λmax=620 nm under voltage application.

Example 8

Synthesis of Example Compound No. 28

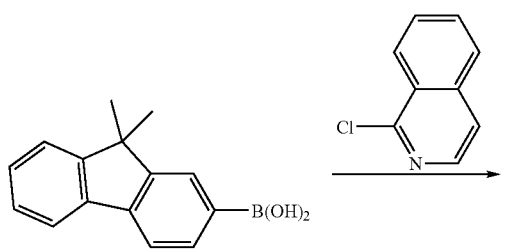

In a 100 ml-three-necked flask, 2.91 g (12.2 mmole) of 9,9-dimethylfluorene-2-boronic acid, 2.00 g (12.2 mmole) of 1-chloroisoquinoline, 10 ml of toluene, 5 ml of ethanol and 10 ml of 2M-sodium carbonate aqueous solution were placed and stirred at room temperature under nitrogen stream, and 0.44 g (0.38 mmole) of tetrakis(triphenylphosphine)palladium (0) was added thereto. Thereafter, reflux under stirring was performed for 5 hours under nitrogen stream. After completion of the reaction, the reaction product was cooled and extracted by addition of cold water and toluene. The organic layer was washed with saline water and dried on magnesium sulfate, followed by removal of the solvent under a reduced pressure to provide dry solid. The residue was purified by silica gel column chromatography (eluent: toluene/ethyl acetate=50/1) to obtain 2.13 g (yield=54.2%) of 1-(9,9-dimethylfluorene-2-yl)isoquinoline.

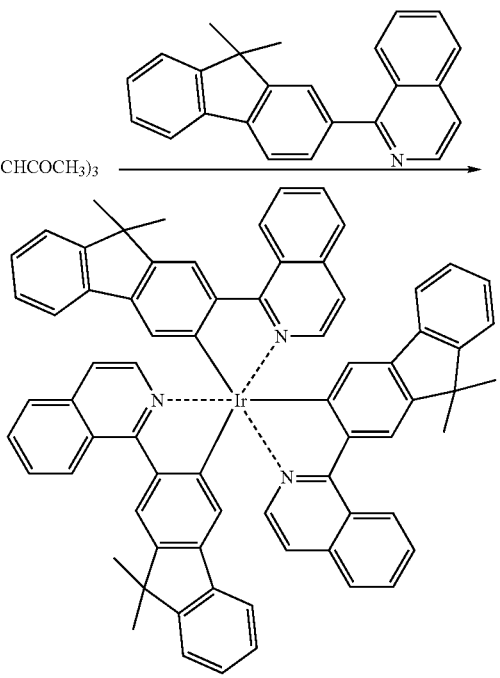

In a 100 ml-four-necked flask, 50 ml of glycerol was placed and heated at 130-140° C. under stirring and bubbling with nitrogen for 2 hours. Then, the glycerol was cooled by standing down to 100° C., and 1.61 g (5.01 mmole) of 1-(9,9-dimethylfluorene-2-yl)isoquinoline and 0.50 g (1.02 mole) of iridium (III) acetylacetonate were added, followed by 8 hours of reflux under stirring and nitrogen stream. The reaction product was cooled to room temperature and injected into 600 ml of 1N-hydrochloric acid to form a precipitate, which was filtered out and washed with water. The precipitate was purified by silica gel column chromatography with chloroform as the eluent to obtain 0.38 g (yield=32.3%) of red powdery tris[1-(9,9-dimethylfluorene-2-yl)isoquinoline-C³,N]iridium (III). According to MALDI-TOF MS, the compound exhibited M' of 1153.4.

A toluene solution of the compound exhibited a luminescence spectrum showing λmax=648 nm and a quantum yield of 0.66 relative to 1.0 of Ir(ppy)₃.

An EL device of Example 2 prepared by using the compound exhibited red luminescence showing λmax=650 nm under voltage application.

Example 9

Synthesis of Example Compound No 25

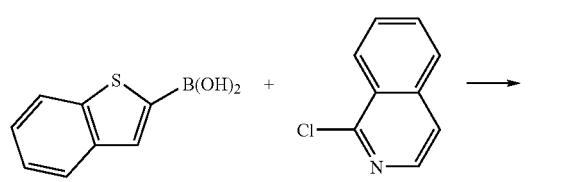

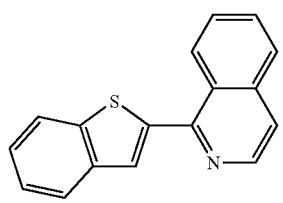

In a 100 ml-three-necked flask, 4.45 g (25.0 mmole) of thianaphthene-2-boronic acid (made by Aldrich Chemical Co., Inc.), 4.09 g (25.0 mmole) of 1-chloroisoquinoline, 25 ml of toluene, 12.5 ml of ethanol and 25 mol of 2M-sodium carbonate aqueous solution were placed and stirred at room temperature under nitrogen stream, and 0.98 g (0.85 mmole) of tetrakis(triphenylphosphine)palladium (0) was added thereto. Thereafter, reflux under stirring was performed for 8 hours under nitrogen stream. After completion of the reaction, the reaction product was cooled and extracted by addition of cold water and toluene. The organic layer washed with saline water and dried on magnesium sulfate, followed by removal of the solvent under a reduced pressure to provide dry solid. The residue was purified by silica gel column chromatography (eluent: chloroform) to obtain 4.20 g (yield=64-3%) of 1-(thianaphthene-2-yl)isoquinoline.

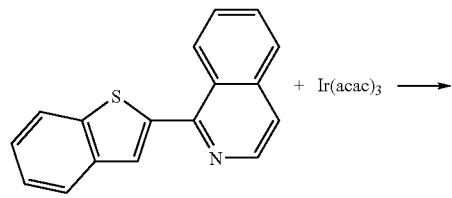

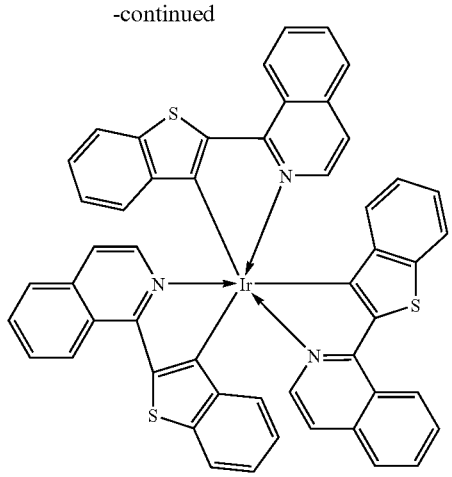

In a 100 ml-four-necked flask, 50 ml of glycerol was placed and heated at 130-140° C. under stirring and bubbling with nitrogen for 2 hours. Then, the glycerol was cooled by standing to 100° C., and 1.31 g (5.01 mmole) of 1-(thianaphthene-2-yl)-isoquinoline, and 0.50 g (1.02 mmole) of iridium (III) acetylacetone, were added, followed by 5 hours of heating around 210° C. under stirring and nitrogen stream. The reaction product was cooled to room temperature and poured into 300 ml of 1N-hydrochloric acid to form a precipitate, which was then filtered out and washed with water. The precipitate was purified by silica gel column chromatography with chloroform as the eluent to obtain 0.25 g (yield 25.2%) of red powdery tris[1-(thianaphthene-2-yl)-isoquinoline-C³,N]iridium (III). According to MALDI-TOF MS, M⁺ of the compound of 973.1 was confirmed. A toluene solution of the compound exhibited a luminescence spectrum showing λmax=686 nm and a quantum yield of 0.07 relative to 1.0 of Ir(ppy)₃.

An EL device was prepared in the same manner as in Example 1 except for using the compound instead of Compound No. 1 and was confirmed to emit deep red luminescence under voltage application.

Example 10

Synthesis of Example Compound No. 24

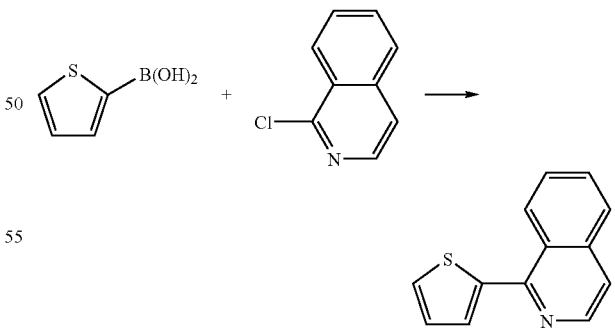

In a 100 ml-three-necked flask, 2.56 g (20.0 mmole) of 2-thiophene-2-boronic acid (made by Aldrich Co.), 3.27 g (20.0 mmole) of 1-chloroisoquinoline, 18 ml of toluene, 9 ml of ethanol and 18 mol of 2M-sodium carbonate aqueous solution were placed and stirred at room temperature under nitrogen stream, and 0.72 g (0.62 mmole) of tetrakis(triphenylphosphine)palladium (0) was added thereto. Thereafter, reflux under stirring was performed for 9 hours under nitrogen stream. After completion of the reaction, the reaction product was cooled and extracted by addition of cold water and toluene. The organic layer was washed with saline water and dried on magnesium sulfate, followed by removal of the solvent under a reduced pressure to provide dry solid. The residue was purified by silica gel column chromatography (eluent: chloroform) to obtain 2.40 g (yield=56.8%) of 1-(2-thienyl)isoquinoline.

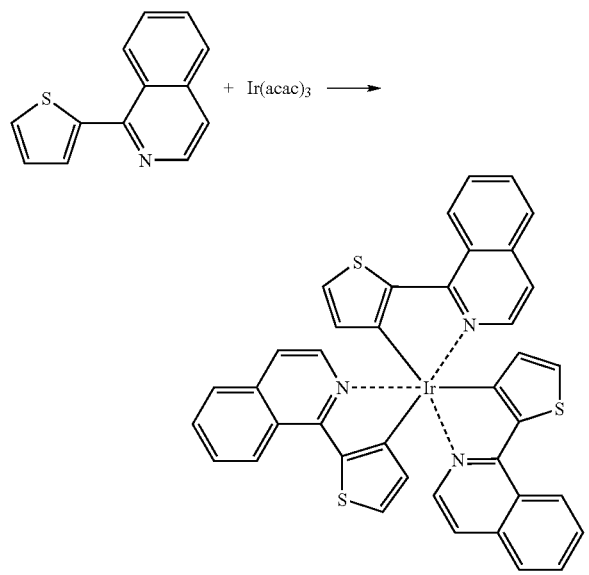

In a 100 ml-four-necked flask, 50 ml of glycerol was placed and heated at 130-140° C. under stirring and bubbling with nitrogen for 2 hours. Then, the glycerol was cooled by standing to 100° C., and 1.05 g (4.97 mmole) of 1-(2-thienyl)isoquinoline, and 0.50 g (1.02 mmole) of iridium (III) acetylacetone, were added, followed by 8 hours of reflux under stirring and nitrogen stream. The reaction product was cooled to room temperature and poured into 600 ml of 1N-hydrochloric acid to form a precipitate, which was then filtered out and washed with water. The precipitate was purified by silica gel column chromatography with chloroform as the eluent to obtain 0.38 g (yield=45.2%) of red powdery tris[1-(2-thienyl)isoquinoline-$C^3$,N]iridium (III). According to MALDI-TOF MS, $M^+$ of the compound of 823.1 was confirmed. A toluene solution of the compound exhibited a luminescence spectrum showing λmax=642 nm and a quantum yield of 0.43 relative to 1.0 of Ir(ppy)$_3$.

An EL device was prepared in the same manner as in Example 1 except for using the compound instead of Compound No. 1 and was confirmed to emit red luminescence showing λmax=640 nm under voltage application.

Example 11

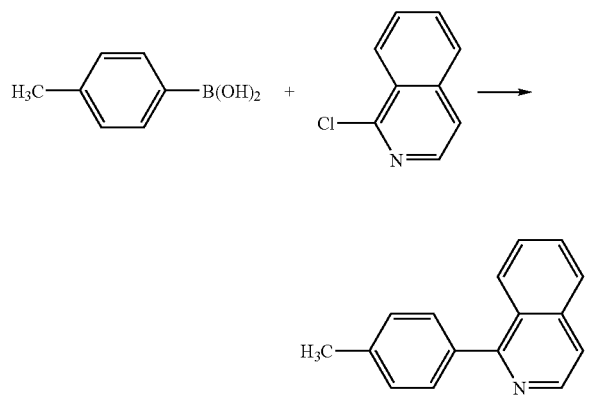

In a 200 ml-three-necked flask, 3.40 g (25.0 mmole) of 4-methylphenyl-boronic acid (made by Aldrich Co.), 4.09 g (25.0 mmole) of 1-chloroisoquinoline, 25 ml of toluene, 12.5 ml of ethanol and 25 mol of 2M-sodium carbonate aqueous solution were placed and stirred at room temperature under nitrogen stream, and 0.98 g (0.85 mmole) of tetrakis(triphenylphosphine)-palladium (0) was added thereto. Thereafter, reflux under stirring was performed for 8 hours under nitrogen stream. After completion of the reaction, the reaction product was cooled and extracted by addition of cold water and toluene. The organic layer washed with saline water and dried on magnesium sulfate, followed by removal of the solvent under a reduced pressure to provide dry solid The residue was purified by silica gel column chromatography (eluent: chloroform/methanol=10/1) to obtain 2.80 g (yield=51.1%) of 1-(4-methylphenyl)isoquinoline.

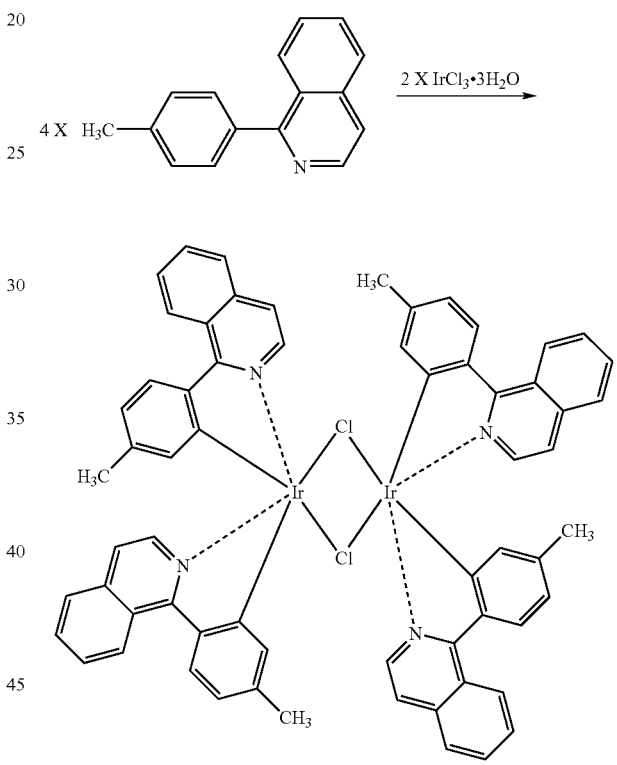

Figure 10:
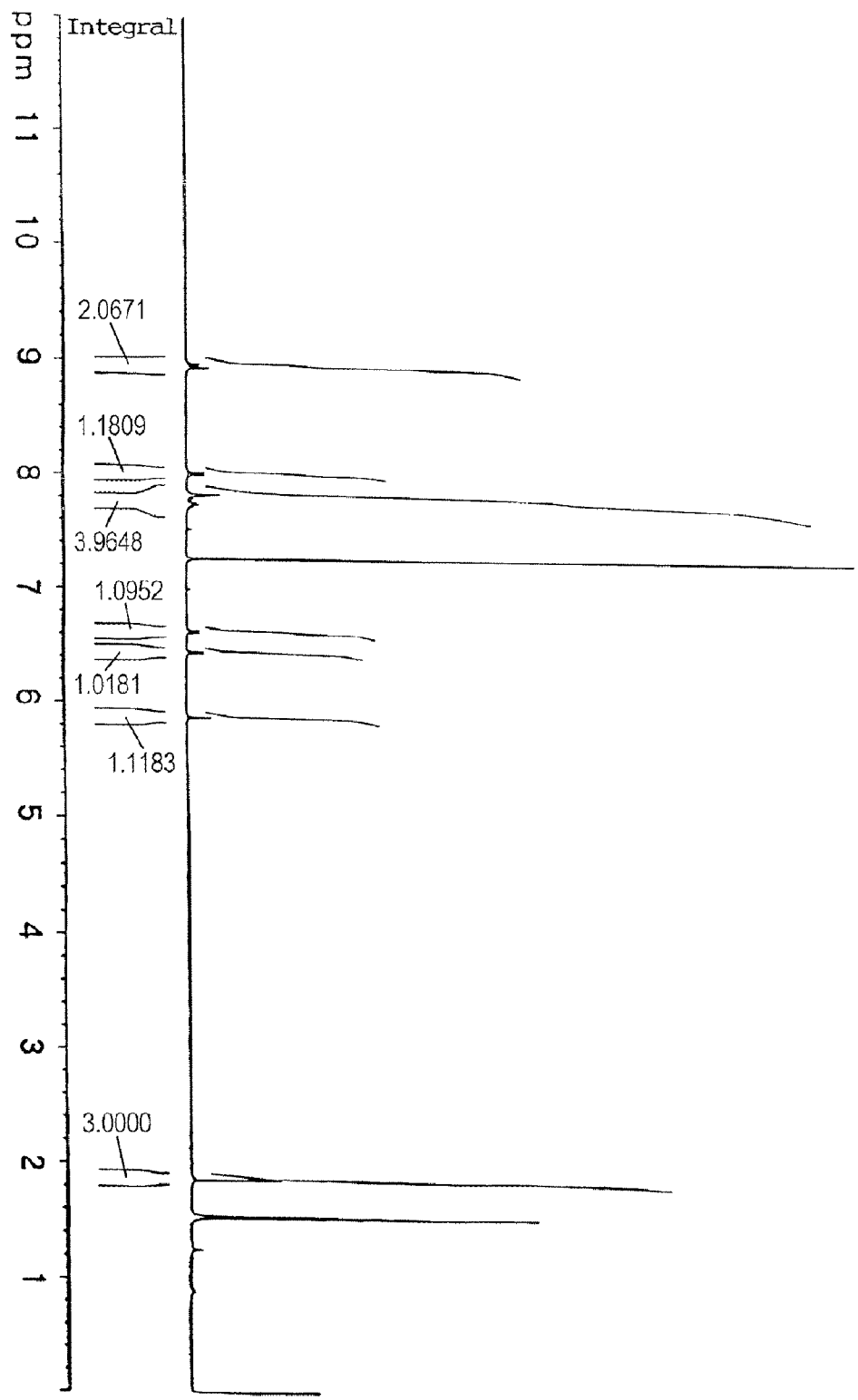
FIG. 10 shows a $^1$H-NMR spectrum of a solution in heavy chloroform of tetrakis[1-4-methylphenyl)isoquinoline-$C^2$,N](μ-dichloro)-diiridium (III).

In a 200 ml-three-necked flask, 0.58 mg (1.64 mmole) of iridium (III) chloride-trihydrate (made by Acros Organics Co.), 1.61 g (7.34 mmole) of 1-(4-methylphenyl)isoquinoline, 45 ml of ethanol and 15 ml of water were placed and stirred for 30 min. at room temperature under nitrogen stream, followed by 24 hours of reflux under stirring. The reaction product was cooled to room temperature, and the precipitate was recovered by filtration and washed with water, followed successive washing with ethanol and acetone. After drying under a reduced pressure at room temperature, 1.02 g (yield=93.4%) of red powdery tetrakis[1-(4-methylphenyl)isoquinoline-$C^2$,N]-(μ-dichloro)diiridium (III) (Example Compound No. 661) was obtained. FIG. 10 shows a $^1$H-NMR spectrum of a heavy chloroform solution of the compound. A toluene solution of the compound exhibited a luminescence spectrum showing λmax=617 n and a quantum yield of 0.46 relative to 1.0 of Ir(ppy)$_3$.

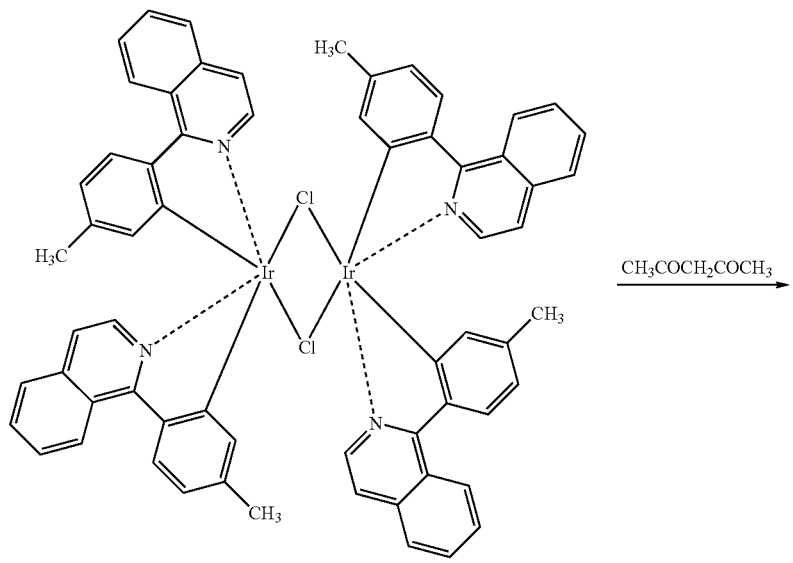

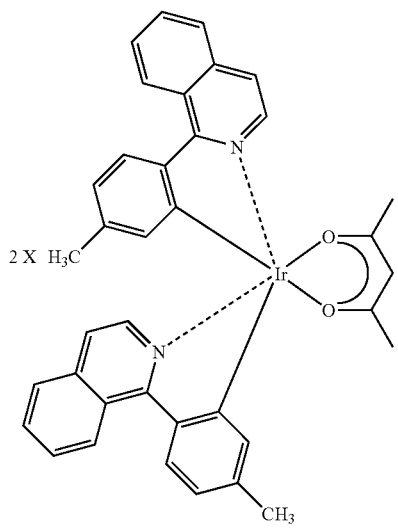

Figure 11:
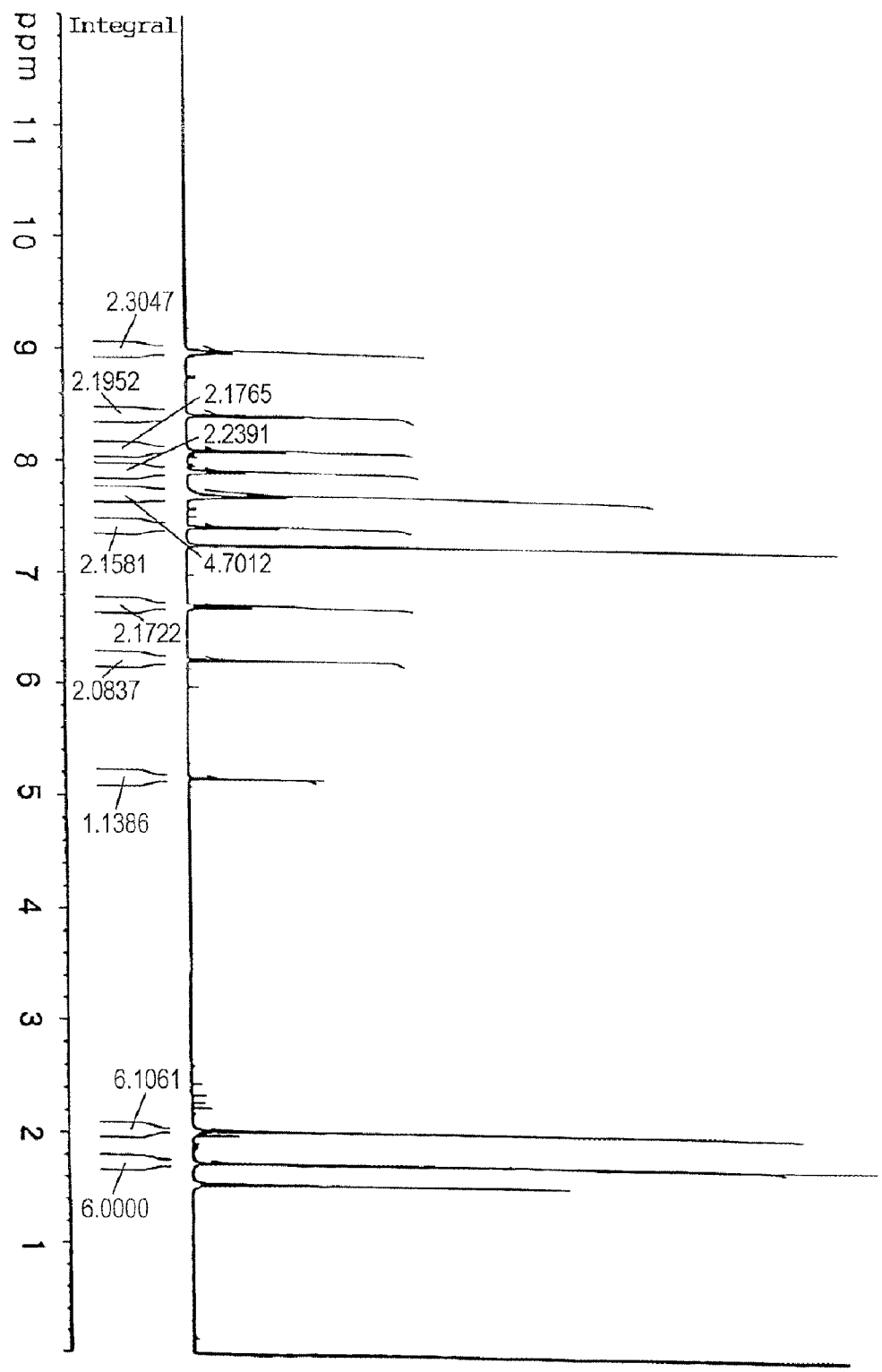
FIG. 11 shows a $^1$H-NMR spectrum of a solution in heavy chloroform of bis[1-(4-methylphenyl)isoquinoline-$C^2$,N](acetylacetonato)-iridium (III).

In a 200 ml-three-necked flask, 70 ml of ethoxyethanol, 0.95 g (0.72 mmole) of tetrakis[1-(4-methylphenyl)isoquinoline-$C^2$,N](μ-dichloro)-diiridium (III). 0.22 g (2.10 mmole) of acetylacetone and 1.04 g (9.91 mmole) of sodium carbonate, were placed and stirred for 1 hour at room temperature under nitrogen stream and then refluxed under stirring for 15 hours. The reaction product was cooled with ice, and the precipitate was filtered out and washed with water. The precipitate was then purified by silica gel column chromatography (eluent: chloroform/methanol=30/1) to obtain 0.43 g (yield=41.3%) of red powdery bis[1-(4-methylphenyl)isoquinoline-$C^2$,N](acetylacetonato)-iridium (III) (Example Compound No. 43). According to MALDI-TOF MS, $M^+$ of 728.2 of the compound was confirmed. FIG. 11 shows a $^1$H-NMR of a heavy chloroform solution of the compound. A toluene solution of the compound exhibited a luminescence spectrum showing λmax=622 nm and a quantum yield of 0.70 relative to 1.0 of Ir(ppy)$_3$.

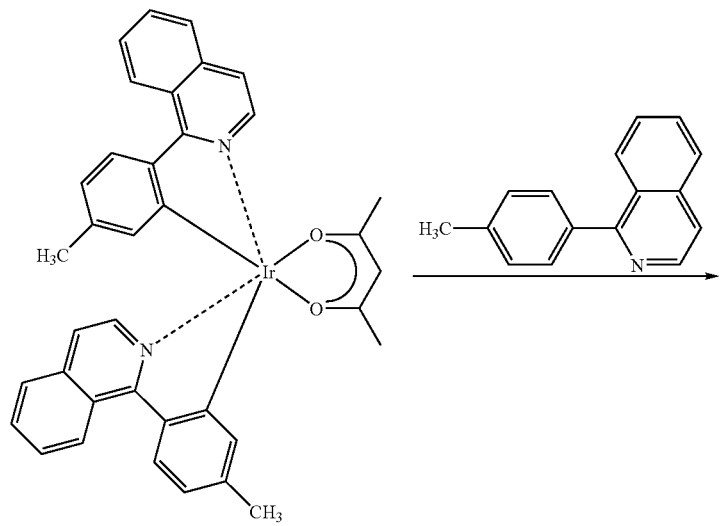

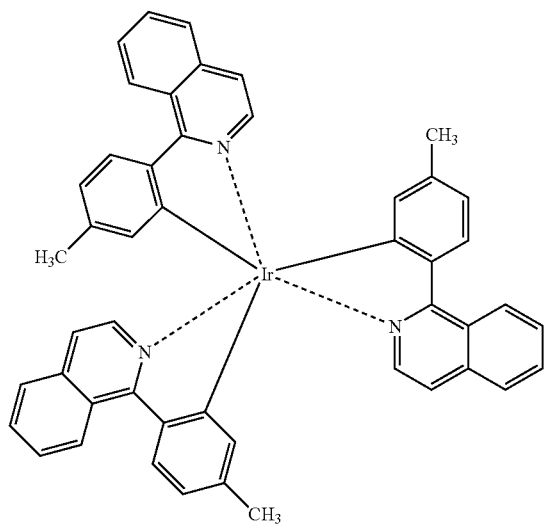

Figure 12:
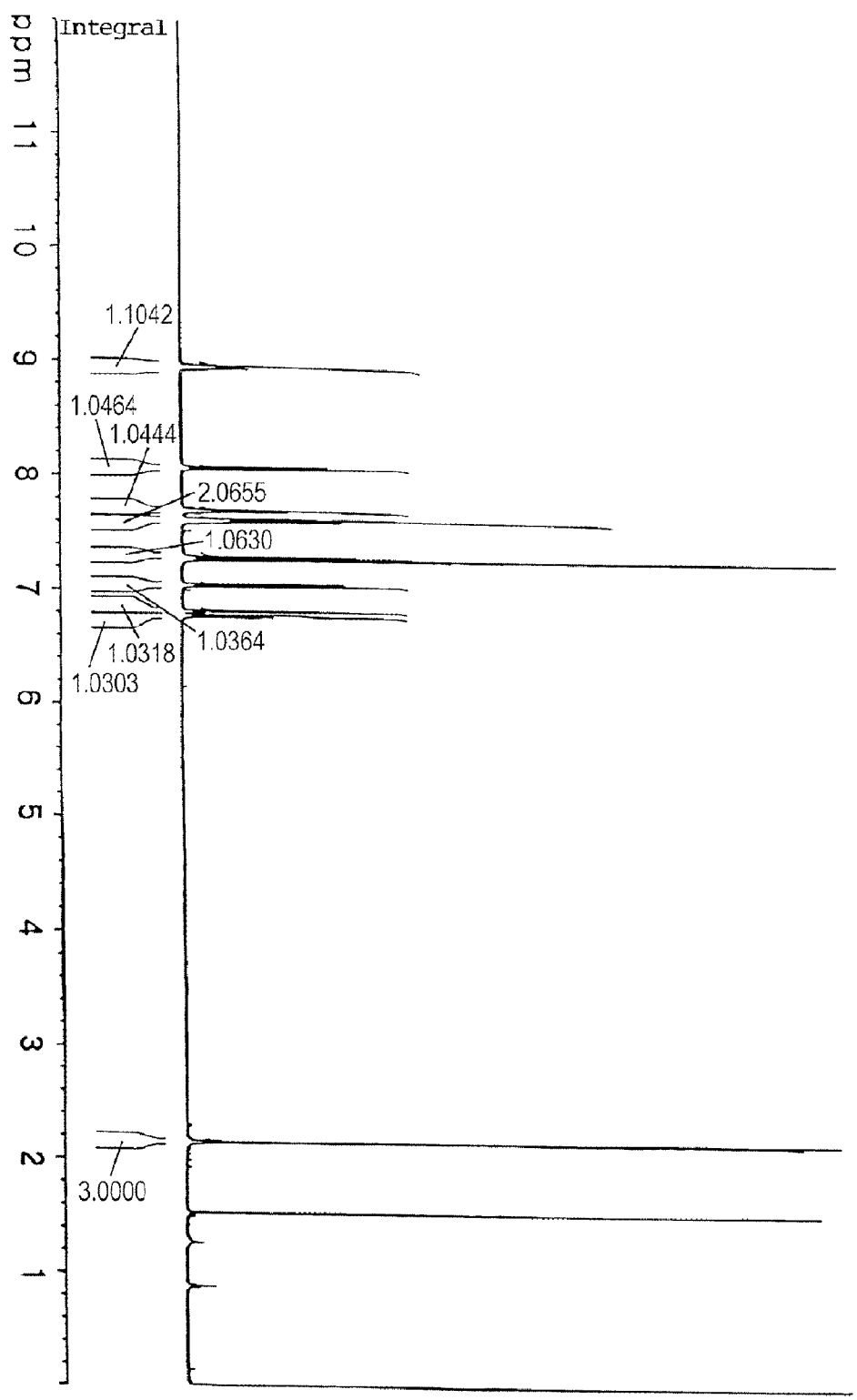
FIG. 12 shows a $^1$H-NMR spectrum of a solution in heavy chloroform of tris[1-(4-methylphenyl)isoquinoline-$C^2$,N]iridium (III).

In a 100 ml-three-necked flask, 0.27 g (1.27 mmole) of 1-(4-methylphenyl)isoquinoline, 0.36 g (0.49 mmole) of bis[1-(4-methylphenyl)isoquinoline-$C^2$,N]-(acetylacetonato) iridium (III) and 25 ml of glycerol, were placed and heated around 180° C. under stirring and nitrogen stream. The reaction product was cooled to room temperature and poured into 170 ml of 1N-hydrochloric acid, and the precipitate was filtered out, washed with water and dried at 100° C. under a reduced pressure for 5 hours. The precipitate was purified by silica gel column chromatography with chloroform as the eluent to obtain 0.27 g (yield=64.5%) of red powdery tris[1-(4-methylphenyl)-isoquinoline-$C^2$,N]iridium (III) (Example Compound No. 19). According to MALDI-TOF MS, $M^+$ of 847.3 of the compound was confirmed. FIG. 12 shows a $^1$H-NMR spectrum of a heavy chloroform solution of the compound. A toluene solution of the compound exhibited a luminescence spectrum showing λmax=619 nm and a quantum yield of 0.65 relative to 1.0 of Ir(ppy)$_3$.

Example 12

The following compounds were successively produced in the same manner as in Example 11 except for using 4-n-hexylphenylboronic acid instead of the 4-methylphenylboronic acid.

Tetrakis[1-(4-n-hexylphenyl)isoquinoline-$C^2$,N[(μ-dichloro)diiridium (Example Compound No. 667)
  luminescence spectrum of toluene solution: λmax=616 nm quantum yield=0.40 relative to 1.0 of Ir(ppy)$_3$.
Bis[1-(4-n-hexylphenyl)isoquinoline-$C^2$,N]-(acetylacetonato)iridium (III) (Example Compound No. 196)
  MALDI-TOF MS:. $M^+$=868.4 luminescence spectrum of toluene solution: λmax=625 nm quantum yield=0.87 relative to 1.0 of Ir(ppy)$_3$.
Tris[1-(4-n-hexylphenyl)isoquinoline-$C^2$,N]-iridium (III) (Example Compound No. 192)
  MALDI-TOF MS: $M^+$=1057.5 luminescence spectrum of toluene solution: λmax=621 nm quantum yield=0.88 relative to 1.0 of Ir(ppy)$_3$

Example 13

The following compounds were successively produced in the same manner as in Example 11 except for using 4-n-octylphenylboronic acid instead of the 4-methylphenylboronic acid.

Figure 13:
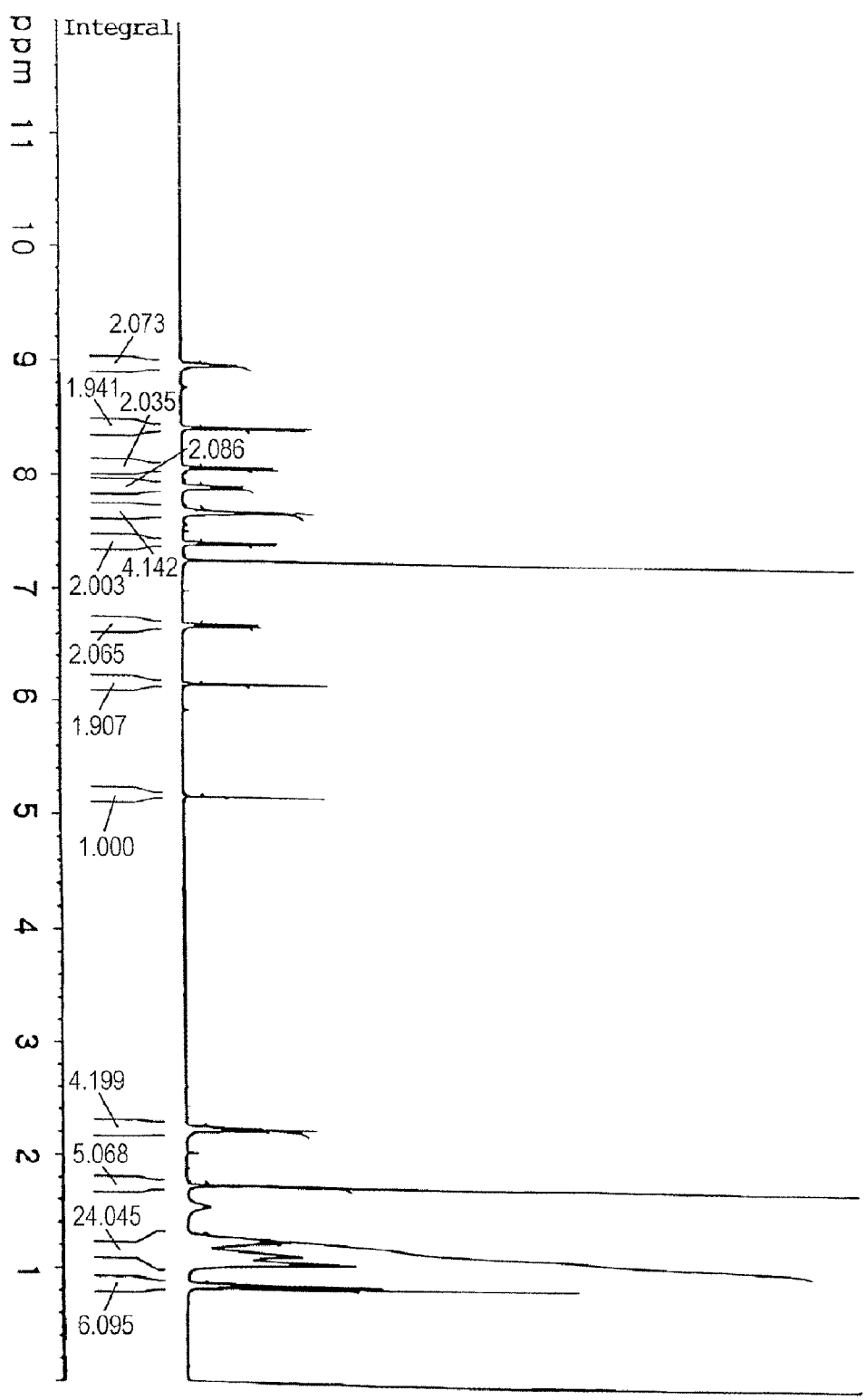
FIG. 13 shows a $^1$H-NMR spectrum of a solution in heavy chloroform of bis[1-(4-n-octylphenyl)isoquinoline-$C^2$,N](acetylacetonato)-iridium (III).

Tetrakis[1-(4-n-octylphenyl)isoquinoline-$C^2$,N[(μ-dichloro) diiridium (Example Compound No. 669)
  luminescence spectrum of toluene solution: $\lambda$max=617 nm quantum yield=0.47 relative to 1.0 of Ir(ppy)$_3$.
Bis[1-(4-n-octylphenyl)isoquinoline-$C^2$,N]-(acetylacetonato)iridium (III) (Example Compound No. 218)
  MALDI-TOF MS: $M^+$=924.4 luminescence spectrum of toluene solution: $\lambda$max=625 nm quantum yield=1.05 relative to 1.0 of Ir(ppy)$_3$
  FIG. 13 shows a $^1$H-NMR spectrum of a heavy chloroform solution of the compound.
Tris[1-4-n-octylphenyl)isoquinoline-$C^2$,N]-iridium (III) (Example Compound No. 214)
  MALDI-TOF MS: $M^+$=1141.6 luminescence spectrum of toluene solution: $\lambda$max=620 nm quantum yield=0.75 relative to 1.0 of Ir(ppy)$_3$

Example 14

The following compounds were successively produced in the same manner as in Example 11 except for using 4-tert-butylphenylboronic acid (made by Aldrich Co.) instead of the 4-methylphenylboronic acid.

Tetrakis[1-(4-t-butylphenyl)isoquinoline-$C^2$,N](μ-dichloro) diiridium (Example Compound No. 665)
  luminescence spectrum of toluene solution: $\lambda$max=614 nm quantum yield=0.39 relative to 1.0 of Ir(ppy)$_3$.
Bis[1-(4-t-butylphenyl)isoquinoline-$C^2$,N]-(acetylacetonato)iridium (III) (Example Compound No. 174)
  MALDI-TOF MS: $M^+$=812.3 luminescence spectrum of toluene solution: $\lambda$max=626 nm quantum yield=0.66 relative to 1.0 of Ir(ppy)$_3$
Tris[1-(4-t-butylphenyl)isoquinoline-$C^2$,N]-iridium (III) (Example Compound No. 170)
  MALDI-TOF MS: $M^+$=973.4 luminescence spectrum of toluene solution: $\lambda$max=618 nm quantum yield=0.73 relative to 1.0 of Ir(ppy)$_3$

Example 15

The following compounds were successively produced in the same manner as in Example 11 except for using 3-fluorophenylboronic acid (made by Aldrich Co.) instead of the 4-methylphenylboronic acid.

Tetrakis[1-(5-fluorophenyl)isoquinoline-$C^2$,N](μ-dichloro) diiridium (Example Compound No 684)
  luminescence spectrum of toluene solution: $\lambda$max=625 nm quantum yield=0.22 relative to 1.0 of Ir(ppy)$_3$.
Bis[1-(5-fluorophenyl)isoquinoline-$C^2$,N]-(acetylacetonato) iridium (III) (Example Compound No. 47)
  MALDI-TOF MS: $M^+$=736.2 luminescence spectrum of toluene solution: $\lambda$max=629 nm quantum yield=0.65 relative to 1.0 of Ir(ppy)$_3$
Tris[1-(5-fluorophenyl)isoquinoline-$C^2$,N]-iridium (III) (Example Compound No. 23)
  MALDI-TOF MS: $M^+$=859.2 luminescence spectrum of toluene solution: $\lambda$max=626 nm quantum yield=0.62 relative to 1.0 of Ir(ppy)$_3$

Example 16

The following compounds were successively produced in the same manner as in Example 11 except for using 4-phenoxyphenylboronic acid instead of the 4-methylphenylboronic acid.

Bis[1-(4-phenoxyphenyl)isoquinoline-$C^2$,N]-(acetylacetonato)iridium (III) (Example Compound No. 365)
  MALDI-TOF MS: $M^+$=884.2 luminescence spectrum of toluene solution: $\lambda$max=608 nm quantum yield=0.65 relative to 1.0 of Ir(ppy)$_3$
Tris[1-(4-phenoxyphenyl)isoquinoline-$C^2$,N]-iridium (III) (Example Compound No. 361)
  MALDI-TOF MS: $M^+$=1081.3 luminescence spectrum of toluene solution: $\lambda$max=604 nm quantum yield=0.54 relative to 1.0 of Ir(ppy)$_3$

Example 17

The following compounds were successively produced in the same manner as in Example 11 except for using 3-methylphenylboronic acid instead of the 4-methylphenylboronic acid.

BiS[1-(4-5-methylphenyl)isoquinoline-$C^2$,N]-(acetylacetonato)iridium (III) (Example Compound No. 44)
  MALDI-TOF MS: $M^+$=728.2 luminescence spectrum of toluene solution: $\lambda$max=638 nm quantum yield=0.78 relative to 1.0 of Ir(ppy)$_3$
Tris[1-(4-5-methylphenyl)isoquinoline-$C^2$,N]-iridium (III) (Example Compound No. 20)
  MALDI-TOF MS: $M^+$=847.3 luminescence spectrum of toluene solution: $\lambda$max=631 nm quantum yield=0.71 relative to 1.0 of Ir(ppy)$_3$

Example 18

1-phenylisoquinoline synthesized in Example 7 was used instead of the 1-(4-methylphenyl)isoquinoline used in Example 11, and the following compound was prepared in a similar manner as in Example 11 via tetrakis(1-phenylisoquinoline-$C^2$,N)(μ-dichloro)-diiridium (III) (Example Compound No. 660).

Bis(1-phenylisoquinoline-$C^2$,N)(acetylacetonato)-iridium (III) (Example Compound No. 42)
  MALDI-TOF MS: $M^+$=700.2 luminescence spectrum of toluene solution: $\lambda$max 604 nm quantum yield=0.54 relative to 1.0 of Ir(ppy)$_3$

Example 19

1-(biphenyl-3-yl)isoquinoline was synthesized by using 3-biphenylboronic acid (made by Frontier Scientific, Inc.) instead of phenylboronic acid in Example 7, and similarly as in Example 7, tris[1-(biphenyl-3-yl)isoquinoline-$C^2$,N]iridium (III) (Example Compound No. 3) was prepared from the 1-(biphenyl-3-yl)isoquinoline and iridium (III) acetylacetonate. According to MALDI-TOF MS, $M^+$ of the compound of 1033.3 was confirmed. A toluene solution of the compound exhibited a luminescence spectrum showing $\lambda$max=621 nm and a quantum yield of 0.53 relative to 1.0 of Ir(ppy)$_3$.

Example 20

3-methyl-2,4-pentanedione (made by Aldrich Co.) instead of acetylacetone in Example 11, and similarly as in Example 11, bis[1-(4-methylphenyl)-isoquinoline-$C^2$,N](3-methyl-2,4-pentanedionato)-iridium (III) (Example Compound No.

126) was synthesized. According to MALDI-TOF MS, M+ of the compound of 742.2 was confirmed. A toluene solution of the compound exhibited a luminescence spectrum showing λmax=627 nm and a quantum yield of 0.81 relative to 1.0 of Ir(ppy)$_3$.

Example 21

2,2,6,6-tetramethyl-3,5-heptanedione (made by Tokyo Kasei Kogyo) was used instead of acetylacetone in Example 11, and similarly as in Example 11, bis[1-(4-methylphenyl)isoquinoline-C$^2$,N](2,2,6,6-tetramethyl-3,5-heptanedionato)iridium (III) (Example Compound No. 127) was synthesized. According to MALDI-TOF MS, M+ of the compound of 812.3 was confirmed A toluene solution of the compound exhibited a luminescence spectrum showing λmax=624 nm and a quantum yield of 0.76 relative to 1.0 of Ir(ppy)$_3$.

Example 22

2-Phenylpyridine was used instead of the 1-(4-methylphenyl)isoquinoline used in Example 11, and similarly as in Example 11, bis(2-phenylpyridine-C$^2$,N)(acetylacetonato)iridium (III) was synthesized via (2-phenylpyridine-C$^2$,N)(μ-dichloro)diiridium (III). The compound was reacted with 1-phenylisoquinoline synthesized in Example 7 in a similar manner as in Example 11 to obtain bis(2-phenylpyridine-C$^2$,N)(1-phenylisoquinoline-C$^2$,N)iridium (III) (Example Compound No. 64) According to MALDI-TOF MS, M+ of the compound of 705.2 was confirmed. A toluene solution of the compound exhibited a luminescence spectrum showing λmax=618 nm and a quantum yield of 0.43 relative to 1.0 of Ir(ppy)$_3$.

Example 23

Bis(1-phenylisoquinoline-C$^2$,N)(acetyl-acetonato)iridium (III) synthesized in Example 18 and 2-phenylpyridine were reacted in a similar manner as in Example 22 to obtain bis(1-phenylisoquinoline-C$^2$,N)(2-phenylpyridine-C$^2$,N)iridium (III) (Example Compound No. 31). According to MALDI-TOF MS, M+ of the compound of 755.2 was confirmed. A toluene solution of the compound exhibited a luminescence spectrum showing λmax=617 nm and a quantum yield of 0.46 relative to 1.0 of Ir(ppy)$_3$.

Example 24

The following compounds were successively produced in the same manner as in Example 11 except for using 4-butylphenylboronic acid (made by Lancaster Synthesis Co.) instead of the 4-methylphenylboronic acid.
Tetrakis[1-(4-n-butylphenyl)isoquinoline-C$^2$,N](μ-dichloro)diiridium (Example Compound No. 664)
 luminescence spectrum of toluene solution: λmax=629 nm quantum yield=0.44 relative to 1.0 of Ir(ppy)$_3$.
Bis[1-(4-butylphenyl)isoquinoline-C$^2$,N]-(acetylacetonato)iridium (III) (Example Compound No. 163)
 MALDI-TOF MS: M+=812.0 luminescence spectrum of toluene solution: λmax=626 nm quantum yield=0.81 relative to 1.0 of Ir(ppy)$_3$
Tris[1-(4-butylphenyl)isoquinoline-C$^2$,N]-iridium (III) (Example Compound No. 159)
 MALDI-TOF MS: M+=973.3 luminescence spectrum of toluene solution: λmax=621 nm quantum yield=0.82 relative to 1.0 of Ir(ppy)$_3$.

Example 25

5-Aminoisoquinoline (made by Tokyo Kasei Kogyo K.K.) was used to synthesize 1-chloro-5-fluoroisoquinoline along the following path with yields as indicated.

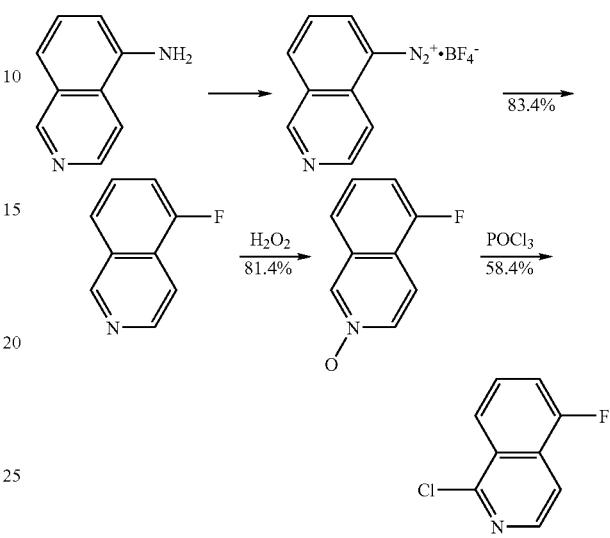

In the process of Example 11, phenylboronic acid was used instead of the 4-methylphenyl-boronic acid and 1-chloro-5-fluoroisoquinoline was used instead of the 1-chloroisoquinoline to synthesize 1-phenyl-5-fluoroisoquinoline, which was used instead of the 1-(4-methylphenyl)isoquinoline otherwise in a similar manner as in Example 11 to synthesize the following compounds successively.
Tetrakis(1-phenyl-5-fluoroisoquinoline-C$^2$,N)(μ-dichloro)diiridium (III) (Example Compound No. 704)
 luminescence spectrum of toluene solution: λmax=620 nm quantum yield=0.38 relative to 1.0 of Ir(ppy)$_3$.
Bis(1-phenyl-5-fluoroisoquinoline-C$^2$,N)-(acetylacetonato)iridium (III) (Example Compound No. 240)
 MALDI-TOF MS: M+=735.8 luminescence spectrum of toluene solution: λmax=636 nm quantum yield=0.70 relative to 1.0 of Ir(ppy)$_3$
Tris(1-phenyl-5-fluoroisoquinoline-C$^2$,N]-iridium (III) (Example Compound No. 155)
 MALDI-TOF MS: M+=858.9 luminescence spectrum of toluene solution: λmax=628 nm quantum yield=0.55 relative to 1.0 of Ir(ppy)$_3$ Example 26

3-Nitro-2-hydroxypyridine (made by Aldrich Co.) was used to synthesize 1-chloro-8-azaisoquinoline along the following path. "Sulfo mix" used for the ring closure was prepared through a process described in J. Org. Chem., 1943, 8, 544-549.

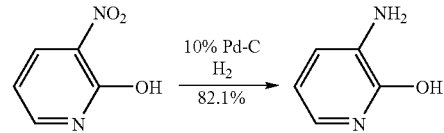

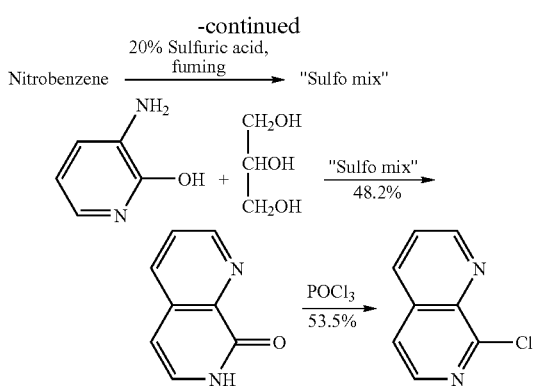

The above-obtained 1-chloro-8-azaisoquinoline was used instead of the 1-chloroisoquinoline in Example 7 to synthesize 1-phenyl-8-azaisoquinoline, which was used instead of the 1-(4-methylphenyl)-isoquinoline otherwise in the same manner as in Example 11 to prepare the following compounds successively.

Tetrakis(1-phenyl-8-azaphenylisoquinoline-$C^2$,N)(μ-dichloro)diiridium (III) (Example Compound No. 755)
luminescence spectrum of toluene solution: λmax=635 nm quantum yield=0.40 relative to 1.0 of Ir(ppy)$_3$.

Bis(1-phenyl-8-azaphenylisoquinoline-$C^2$,N)-(acetylacetonato)iridium (III) (Example Compound No. 612)
MALDI-TOF MS: M$^+$=701.1 luminescence spectrum of toluene solution: λmax=631 nm Tris(1-phenyl-8-azaphenylisoquinoline-$C^2$,N)-iridium (III) (Example Compound No. 609)
MALDI-TOF MS: M$^+$=807.9 luminescence spectrum of toluene solution: λmax=622 nm

Example 27

An EL device having a laminate structure as shown in FIG. 1(b) was prepared. On an ITO electrode 14 patterned on a 1.1 mm-thick alkali-free glass substrate 15, α-NPD was deposited in a thickness of 40 nm at a vacuum deposition rate of 0.1 nm/sec at a vacuum pressure of $10^{-4}$ Pa to form a hole-transporting layer 13, and then CBP and tris(1-phenylisoquinoline-$C^2$,N)iridium (III) (Example Compound No. 1) in an amount of providing a concentration of 9% were co-vacuum-deposited to form a 40 nm-thick luminescence layer 12 while controlling the heating conditions of the vacuum deposition boats so as to provide vacuum deposition rates of 0.1 nm/sec for CBP and 0.09 nm/sec for the iridium complex.

Then, an electron-transporting layer was formed in a thickness of 40 nm by vacuum deposition of bathophenanthroline Bphen represented by a structural formula shown below at a rate of 0.1 nm/sec.

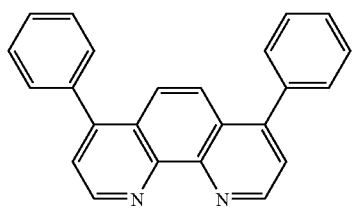

Thereon a ca. 1 nm-thick potassium fluoride layer was formed as an electron-transporting layer 16 by vacuum deposition at a rate of 0.5 nm/sec, and then aluminum was vacuum-deposited in a thickness of 150 nm at a rate of 1 nm/sec to provide a cathode metal 11.

Figure 5:
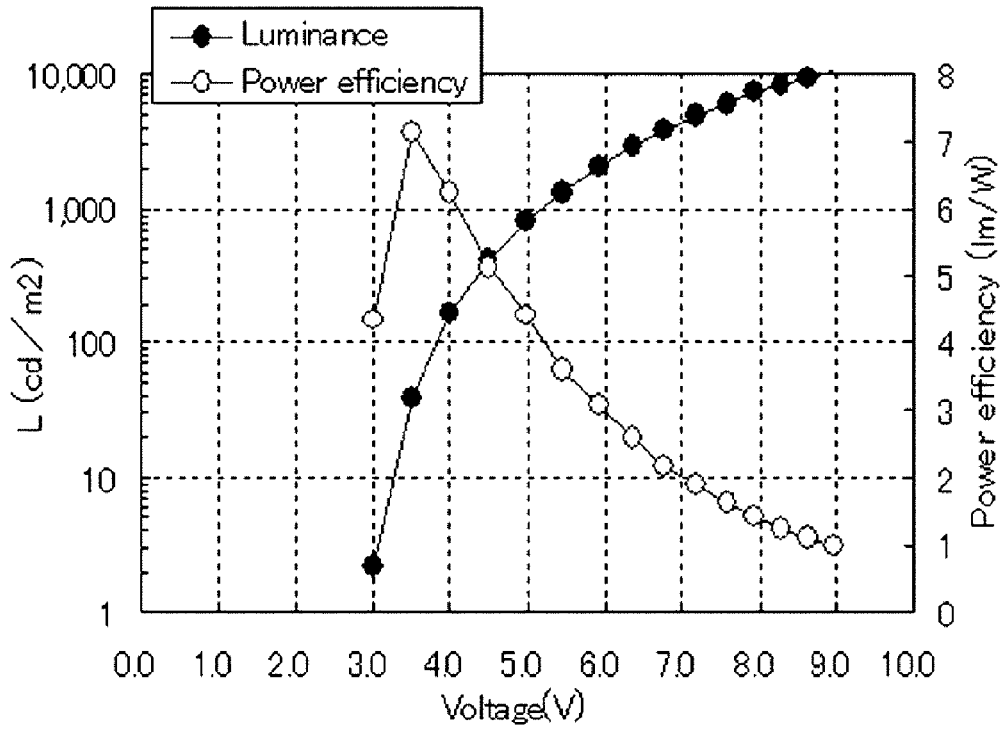
FIG. 5 is a graph showing voltage-efficiency luminance characteristics of a device of Example 27.

The device of this Example was prepared while aiming at the effects of (1) increased supply of electrons and suppression of hole leakage by use of Bphen, (2) improved electron-injection characteristic by use of KF and (3) optmization of optical layer thickness. The voltage-efficiency-luminance characteristics of the thus-obtained device are shown in FIG. 5.

The device of this Example succeeded in realizing efficiencies of 6.2 lm/w and 5.2 lm/w at luminances of 100 cd/m$^2$ and 300 cd/m$^2$, respectively. CIE coordinates were (0.68, 0.317) at 40 cd/m$^2$, (0.682, 0.315) at 113 cd/m$^2$ and (0.678, 0.317) at 980 cd/m$^2$, thus showing that a sufficient color purity was provided according to a color standard of the NTSC. Thus, the luminescence color was substantially unchanged at different luminances and voltages.

Tris(1-phenylisoquinoline-$C^2$,N)iridium (III) having a ligand of 1-phenylisoquinoline can provide red luminescence according to the NTSC standard even without adding a substituent to the ligand skeleton for luminescence color adjustment of the complex, and is thus excellent as a red luminescence material. Further, it is also a desirable luminescence material from a practical viewpoint of shorter synthesis steps as the effect is attained by using a ligand having no substituent.

Figure 6:
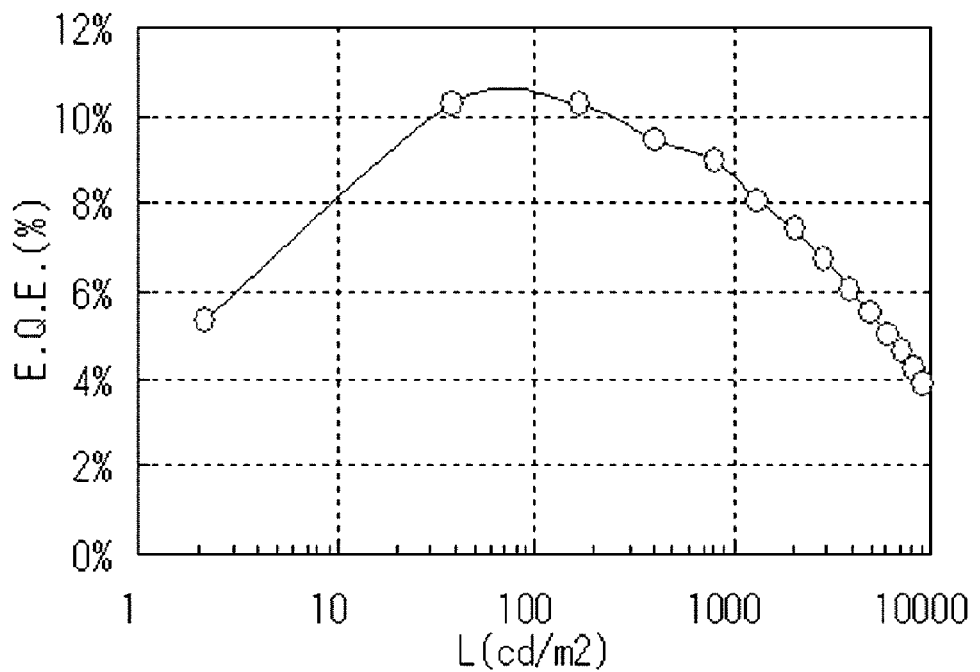
FIG. 6 is a graph showing external Quantum efficiency of a device of Example 27.

The drive conditions included an application voltage v=5 volts and a current J=1.5 mA/cm$^2$ at a luminance of 300 cd/m$^2$, and also 10 volts and 520 mA/cm$^2$ at 14000 cd/m$^2$. The external quantum efficiency (E.Q.E.) values (%) of the thus-prepared EL device are plotted on FIG. 6 and showing efficiencies remarkably improving the efficiency of the conventional EL device, e.g., over 10% at 100 cd/m$^2$.

Example 28

It is easy to successively synthesize the following compounds in the same manner as in Example 11 except for using 4-ethylphenylboronic acid (made by Lancaster Co.) instead of the 4-methylphenylboronic acid in Example 11.

Tetrakis[1-(4-ethylphenyl)isoquinoline-$C^2$,N(μ-dichloro)iridium (III) (Example Compound No. 662), Bis[1-(4-ethylphenyl)isoquinoline-$C^2$,N]-(acetylacetonato) iridium (III) (Example Compound No. 137), Tris[1-(4-ethylphenyl)isoquinoline-$C^2$,N]-iridium (III) (Example Compound No. 135).

Example 29

It is easy to successively synthesize the following compounds in the same manner as in Example 11 except for using 4-propylphenylboronic acid instead of the 4-methylphenylboronic acid in Example 11.

Tetrakis[1-(4-propylphenyl)isoquinoline-$C^2$,N](μ-dichloro) iridium (III) (Example Compound No. 663), Bis[1-(4-propylphenyl)isoquinoline-$C^2$,N]-(acetylacetonato)iridium (III) (Example Compound No. 148), Tris[1-(4-propylphenyl) isoquinoline-$C^2$,N]-iridium (III) (Example Compound No. 144).

Example 30

It is easy to successively synthesize the following compounds in the same manner as in Example 11 except for using 4-isopropylphenylboronic acid (made by Lancaster Co.) instead of the 4-methyl-phenylboronic acid in Example 11.
Tetrakis[1-(4-isopropylphenyl)isoquinoline-$C^2$,N](µ-dichloro)iridium (III),
Bis[1-(4-isopropylphenyl)isoquinoline-$C^2$,N]-(acetylacetonato)iridium (III),
Tris[1-(4-isopropylphenyl)isoquinoline-$C^2$,N]-iridium (III) (Example Compound No. 146).

Example 31

It is easy to successively synthesize the following compounds in the same manner as in Example 11 except for using 4-n-pentylphenylboronic acid instead of the 4-methylphenylboronic acid in Example 11.
Tetrakis[1-(4-n-pentylphenyl)isoquinoline-$C^2$,N](µ-dichloro)iridium (III) (Example Compound No. 666),
Bis[1-(4-n-pentylphenyl)isoquinoline-$C^2$,N]-(acetylacetonato)iridium (III) (Example Compound No. 185),
Tris[1-(4-n-pentylphenyl)isoquinoline-$C^2$,N]-iridium (III) (Example Compound No. 181).

Example 32

It is easy to successively synthesize the following compounds in the same manner as in Example 11 except for using 4-n-heptylphenylboronic acid instead of the 4-methylphenylboronic acid in Example 11.
Tetrakis[1-(4-n-heptylphenyl)isoquinoline-$C^2$,N](µ-dichloro)iridium (III) (Example Compound No-668),
Bis[1-(4-n-heptylphenyl)isoquinoline-$C^2$,N]-(acetylacetonato)iridium (III) (Example Compound No. 207),
Tris[1-(4-n-heptylphenyl)isoquinoline-$C^2$,N]-iridium (III) (Example Compound No-203).

Example 33

The following compounds were successively produced in the same manner as in Example 11 except for using 4-fluorophenylboronic acid (made by Aldrich Co.) instead of the 4-methylphenylboronic acid.
Tetrakis[1-(4-n-hexylphenyl)isoquinoline-$C^2$,N[(µ-dichloro)diiridium (Example Compound No 683)
luminescence spectrum of toluene solution: λmax=602 nm quantum yield=0.40 relative to 1.0 of Ir(ppy)$_3$.
Bis[1-(4-fluorohexylphenyl)isoquinoline-$C^2$,N]-(acetylacetonato)iridium (III) (Example Compound No. 46)
MALDI-TOF MS: M$^+$=737.2 luminescence spectrum of toluene solution: λmax=603 nm quantum yield=0.95 relative to 1.0 of Ir(ppy)$_3$
Tris[1-(4-fluorophenyl)isoquinoline-$C^2$,N]-iridium (III) (Example Compound No. 22)
MALDI-TOF MS: M$^+$=859.2 luminescence spectrum of toluene solution: λmax=596 nm quantum yield=0.92 relative to 1.0 of Ir(ppy)$_3$ Example 34

The following compounds were successively produced in the same manner as in Example 11 except for using 4-fluoro-3-methylphenylboronic acid (made by Aldrich Co.) instead of the 4-methylphenylboronic acid.
Tetrakis[1-(4-fluoro-5-methylphenyl)isoquinoline-$C^2$,N](µ-dichloro)diiridium (Example Compound No. 738)
luminescence spectrum of toluene solution: λmax=618 nm
Bis[1-(4-fluoro-5-methylphenyl)isoquinoline-$C^2$,N]-(acetylacetonato) iridium (III) (Example Compound No. 222)
MALDI-TOF MS: M$^+$=765.2 luminescence spectrum of toluene solution: λmax=615 nm
Tris[1-(4-fluoro-5-methylphenyl)isoquinoline-$C^2$,N]-iridium (III) (Example Compound No. 226)
MALDI-TOF MS: M$^+$=901.1 luminescence spectrum of toluene solution: λmax=616 nm Example 35

The following compounds were successively produced in the same manner as in Example 11 except for using 4-trifluoromethylphenylboronic acid (made by Lancaster Co.) instead of the 4-methylphenylboronic acid.
Tetrakis[1-(4-trifluoromethylphenyl)isoquinoline-$C^2$,N [(µ-dichloro)diiridium
luminescence spectrum of toluene solution: λmax=614 nm
Bis[1-(4-tritluoromethylphenyl)isoquinoline-$C^2$,N]-(acetylacetonato)iridium (III)
MALDI-TOF MS: M$^+$=836.1 luminescence spectrum of toluene solution: λmax=623 nm quantum yield=0.23 relative to 1.0 of Ir(ppy)$_3$
Tris](1-(4-trifluoromethylphenyl)isoquinoline-$C^2$,N]-iridium (III) (Example Compound No. 11)
MALDI-TOF MS: M$^+$=1009.2 luminescence spectrum of toluene solution: λmax=608 nm quantum yield=0.48 relative to 1.0 of Ir(ppy)$_3$.

Example 36

It is easy to successively synthesize the following compounds in the same manner as in Example 11 except for using 3-trifluoromethylphenylboronic acid (made by Lancaster Co.) instead of the 4-methylphenylboronic acid in Example 11.
Tetrakis[1-(5-trifluoromethylphenyl)isoquinoline-$C^2$,N](µ-dichloro)iridium (III)
Bis[1-(5-trifluoromethylphenyl)isoquinoline-$C^2$,N]-(acetylacetonato)iridium (III)
Tris[1-(5-trifluoromethylphenyl)isoquinoline-$C^2$,N]-iridium (III) (Example Compound No. 12).

Example 37

The following compounds were successively produced in the same manner as in Example 11 except for using 3,5-difluoro-3-methylphenylboronic acid (made by Aldrich Co.) instead of the 4-methyl-phenylboronic acid.
Tetrakis[1-(3,5-difluoro-3-methylphenyl)iso-quinoline-$C^2$,N](µ-dichloro)diiridium (Example Compound No. 686)
luminescence spectrum of toluene solution: λmax=618 nm
Bis[1-(3,5-fluoro-3-methylphenyl)isoquinoline-$C^2$,N]-(acetylacetonato)iridium (III) (Example Compound No. 425)
MALDI-TOF MS: M$^+$=765.2 luminescence spectrum of toluene solution: λmax=625 nm
Tris[1-(3,5-difluoro-3-methylphenyl)isoquinoline-$C^2$,N]-iridium (III) (Example Compound No. 421)
MALDI-TOF MS: M$^+$=901.2 luminescence spectrum of toluene solution: λmax=616 nm Example 38

It is easy to successively synthesize the following compounds in the same manner as in Example 11 except for using 2,3-difluorophenylboronic acid instead of the 4-methylphenylboronic acid in Example 11.

Tetrakis[1-(5,6-difluorophenyl)isoquinoline-C², N](μ-dichloro)iridium (III)

Bis[1-(5,6-difluorophenyl)isoquinoline-C²,N]-(acetylacetonato)iridium (III) (Example Compound No. 501), Tris[1-(5,6-difluorophenyl)isoquinoline-C²,N]-iridium (III) (Example Compound No. 497).

Example 39

It is easy to successively synthesize the following compounds in the same manner as in Example 11 except for using 2,3-difluoro-4-n-butylphenyl-boronic acid instead of the 4-methylphenylboronic acid in Example 11.

Tetrakis[1-(4-n-butyl-5,6-difluorophenyl)-isoquinoline-C², N](μ-dichloro)iridium (III) (Example Compound No. 698), Bis[1-(4-n-butyl-5,6-difluorophenyl)isoquinoline-C²,N]-(acetylacetonato)iridium (III) (Example Compound No. 534), Tris[1-(4-n-butyl-5,6-difluorophenyl)isoquinoline-C²,N]-iridium (III) (Example Compound No. 530).

Example 40

It is easy to successively synthesize the following compounds in the same manner as in Example 11 except for using 1-phenyl-5-trifluoromethyl-isoquinoline, synthesized in the same manner as in Example 7 by using 1-chloro-5-trifluoromethyl-isoquinoline instead of the 1-chloroisoquinoline in Example 7.

Tetrakis[1-phenyl-5-trifluoromethylisoquinoline-C²,N](μ-dichloro)iridium (III) (Example Compound No. 706), Bis[1-phenyl-5-trifluoromethylisoquinoline-C²,N]-(acetylacetonato)iridium (III), Tris[1-phenyl-5-trifluoromethylisoquinoline-C²,N]-iridium (III) (Example Compound No. 83).

Example 41

It is easy to successively synthesize the following compounds in the same manner as in Example 11 except for using 1-phenyl-4-trifluoromethyl-isoquinoline, synthesized in the same manner as in Example 7 by using 1-chloro-4-trifluoromethyl-isoquinoline instead of the 1-chloroisoquinoline in Example 7.

Tetrakis[1-phenyl-4-trifluoromethylisoquinoline-C²,N](μ-dichloro)iridium (III) (Example Compound No. 706), Bis[1-phenyl-4-trifluoromethylisoquinoline-C²,N]-(acetylacetonato)iridium (III), Tris(1-phenyl-4-trifluoromethylisoquinoline-C²,N)-iridium (III) (Example Compound No 82).

Example 42

It is easy to successively synthesize the following compounds in the same manner as in Example 11 except for using 1-phenyl-4-trifluoromethyl-isoquinoline, synthesized in the same manner as in Example 7 by using 1-chloro-4-trifluoromethyl-isoquinoline instead of the 1-chloroisoquinoline in Example 7.

Tetrakis[1-phenyl-4-trifluoroisoquinoline-C²,N](μ-dichloro)iridium (III) (Example Compound No. 705), Bis[1-phenyl-4-trifluoroisoquinoline-C²,N]-(acetylacetonato)iridium (III), Tris[1-phenyl-4-trifluoroisoquinoline-C²,N]-iridium (III) (Example Compound No. 81).

Example 43

It is easy to successively synthesize the following compounds in the same manner as in Example 11 except for using 3,5-difluorophenylboronic acid and 1-chloro-5-fluoroisoquinoline instead of the 4-methylphenylboronic acid and 1-chloroisoquinoline, respectively, in Example 11.

Tetrakis[1-(3,5-difluorophenyl)-5-fluoroiso-quinoline-C², N](μ-dichloro)diiridium (III).

Bis[1-(3,5-difluorophenyl)-5-fluoroisoquinoline-C²,N](acetylacetonato)iridium (III).

Tris[1-(3,5-difluorophenyl)-5-fluoroisoquinoline-C²,N]iridium (III) (Example Compound No. 232).

Example 44

It is easy to successively synthesize the following compounds in the same manner as in Example 11 except for using 4-difluorophenylboronic acid and 1-chloro-4-fluoroisoquinoline instead of the 4-methylphenylboronic acid and 1-chloroisoquinoline, respectively, in Example 11.

Tetrakis[1-(4-difluorophenyl)-4-fluoroiso-quinoline-C²,N](μ-dichloro)diiridium (III).

Bis[1-(4-difluorophenyl)-4-fluoroisoquinoline-C²,N](acetylacetonato)iridium (III).

Tris[1-(4-difluorophenyl)-4-fluoroisoquinoline-C²,N]iridium (III) (Example Compound No. 230).

Example 45

It is easy to successively synthesize the following compounds in the same manner as in Example 11 except for using 4-difluorophenylboronic acid and 1-chloro-5-fluoroisoquinoline instead of the 4-methylphenylboronic acid and 1-chloroisoquinoline, respectively, in Example 11.

Tetrakis[1-(4-difluorophenyl)-5-fluoroiso-quinoline-C²,N](μ-dichloro)diiridium (III).

Bis[1-(4-difluorophenyl)-5-fluoroisoquinoline-C²,N](acetylacetonato)iridium (III).

Tris[1-(4-difluorophenyl)-5-fluoroisoquinoline-C²,N]iridium (III) (Example Compound No. 228).

Example 46

It is easy to successively synthesize the following compounds in the same manner as in Example 11 except for using 4-trifluoromethylphenylboronic acid and 1-chloro-4-fluoroisoquinoline instead of the 4-methylphenylboronic acid and 1-chloroisoquinoline, respectively, in Example 11.

Tetrakis[1-(4-trifluorofluorophenyl)-4-fluoroisoquinoline-C²,N](μ-dichloro)diiridium (III).

Bis[1-(4-trifluoromethylphenyl)-4-fluoroisoquinoline-C², N](acetylacetonato)iridium (III).

Tris[1-(4-trifluoromethylphenyl)-4-fluoroisoquinoline-C², N]iridium (III) (Example Compound No. 256).

Example 47

It is easy to successively synthesize the following compounds in the same manner as in Example 11 except for using 4-fluorophenylboronic acid and 1-chloro-4-trifluoromethyl-isoquinoline instead of the 4-methylphenylboronic acid and 1-chloroisoquinoline, respectively, in Example 11.

Tetrakis[1-(4-fluorophenyl)-4-trifluoromethyl-quinoline-C$^2$,N](μ-dichloro)diiridium (III).
Bis[1-(4-fluorophenyl)-4-trifluoromethylquinoline-C$^2$,N](acetylacetonato)iridium (III).
Tris[1-(4-fluorophenyl)-4-trifluoromethylisoquinoline-C$^2$,N]iridium (III) (Example Compound No. 231).

Example 48

It is easy to successively synthesize the following compounds in the same manner as in Example 11 except for using 4-fluorophenylboronic acid and 1-chloro-5-fluoroisoquinoline instead of the 4-methylphenylboronic acid and 1-chloroisoquinoline, respectively, in Example 11.
Tetrakis[1-(4-fluorophenyl)-5-trifluoromethylisoquinoline-C$^2$,N](μ-dichloro)diiridium (III).
Bis[1-(4-fluorophenyl)-5-trifluoromethylisoquinoline-C$^2$,N](acetylacetonato)iridium (III).
Tris[1-(4-fluorophenyl)-5-trifluoromethylisoquinoline-C$^2$,N]iridium (III) (Example Compound No. 229).

Example 49

It is easy to successively synthesize the following compounds in the same manner as in Example 11 except for using 4-trifluoromethylphenylboronic acid and 1-chloro-4-trifluoromethylisoquinoline instead of the 4-methylphenylboronic acid and 1-chloroisoquinoline, respectively, in Example 11.
Tetrakis[1-(4-trifluoromethylphenyl)-4-trifluoromethylisoquinoline-C$^2$,N](μ-dichloro)diiridium (III) (Example Compound No. 691).
Bis[1-(4-trifluoromethylphenyl)-4-trifluoromethyl isoquinoline-C$^2$,N](acetylacetonato)iridium (III).
Tris[1-(4-trifluoromethylphenyl)-4-trifluoromethylisoquinoline-C$^2$,N]iridium (III) (Example Compound No 260).

Example 50

It is easy to successively synthesize the following compounds in the same manner as in Example 11 except for using 4-trifluoromethylphenylboronic acid and 1-chloro-5-trifluoromethylisoquinoline instead of the 4-methylphenylboronic acid and 1-chloroisoquinoline, respectively, in Example 11.
Tetrakis[1-(4-trifluoromethylphenyl)-5-trifluoromethylisoquinoline-C$^2$,N](μ-dichloro)diiridium (III).
Bis[1-(4-trifluoromethylphenyl)-5-trifluoromethyl-isoquinoline-C$^2$,N](acetylacetonato)iridium (III).
Tris[1-(4-trifluoromethylphenyl)-5-trifluoromethylisoquinoline-C$^2$,N]iridium (III) (Example Compound No. 255).

Example 51

It is easy to successively synthesize the following compounds in the same manner as in Example 11 except for using 3,4,5-trifluorophenylboronic acid (made by Lancaster Co.) and 1-chloro-4-trifluoromethylisoquinoline instead of the 4-methylphenylboronic acid and 1-chloroisoquinoline, respectively, in Example 11.
Tetrakis[1-(3,4,5-trifluorophenyl)-4-trifluoro methylquinoline-C$^2$,N](μ-dichloro)diiridium (III).
Bis[1-(3,4,5-trifluorophenyl)-4-trifluoromethylisoquinoline-C$^2$,N](acetylacetonato)iridium (III).
Tris[1-(3,4,5-trifluorophenyl)-4-trifluoromethylisoquinoline-C$^2$,N]iridium (III) (Example Compound No. 253).

Example 52

It is easy to successively synthesize the following compounds in the same manner as in Example 11 except for using 3,4,5-trifluorophenylboronic acid (made by Lancaster Co.) and 1-chloro-5-trifluoromethylisoquinoline instead of the 4-methylphenylboronic acid and 1-chloroisoquinoline, respectively, in Example 11.
Tetrakis[1-(3,4,5-trifluorophenyl)-5-trifluoromethylisoquinoline-C$^2$,N](P-dichloro)diiridium (III).
Bis[1-(3,4,5-trifluorophenyl)-5-trifluoromethylisoquinoline-C$^2$,N](acetylacetonato)iridium (III).
Tris[1-(3,4,5-trifluorophenyl)-5-trifluoromethylisoquinoline-C$^2$,N]iridium (III) (Example Compound No. 250).

Example 53

It is easy to successively synthesize the following compounds in the same manner as in Example 11 except for using 3,4,5,6-tetrafluorophenylboronic acid and 1-chloro-4-trifluoromethylisoquinoline instead of the 4-methylphenylboronic acid and 1-chloroisoquinoline, respectively, in Example 11.
Tetrakis[1-(3,4,5,6-tetrafluorophenyl)-4-trifluoromethylisoquinoline-C$^2$,N](μ-dichloro)diiridium (III).
Bis[1-(3,4,5,6-trifluorophenyl)-4-trifluoromethylisoquinoline-C$^2$,N](acetylacetonado)iridium (III).
Tris[1-(3,4,5,6-tetrafluorophenyl)-4-trifluoromethylisoquinoline-C$^2$,N]iridium (III) (Example Compound No. 268).

Example 54

It is easy to successively synthesize the following compounds in the sane manner as in Example 11 except for using 3,4,5,6-tetrafluorophenylboronic acid and 1-chloro-5-trifluoromethylisoquinoline instead of the 4-methylphenylboronic acid and 1-chloroisoquinoline, respectively, in Example 11.
Tetrakis[1-(3,4,5,6-tetrafluorophenyl)-5-trifluoromethylisoquinoline-C$^2$,N](μ-dichloro)diiridium (III) (Example Compound No. 690).
Bis[1-(3,4,5,6-tetrafluorophenyl)-5-trifluoromethylisoquinoline-C$^2$,N](acetylacetonato)iridium (III).
Tris[1-(3,4,5,6-tetrafluorophenyl)-5-trifluoromethylisoquinoline-C$^2$,N]iridium (III) (Example Compound No. 272).

Example 55

It is easy to synthesize 1-chloro-3,4,5,6,7,8-hexafluoroisoquinoline along the following path according to processes described in references: J. Chem. Soc. C, 1966, 2328-2331; J. Chem. Soc. C, 1971, 61-67; J. Org. Chem., 1971, 29, 329-332 and Org, Syn., 1960, 40, 7-10:

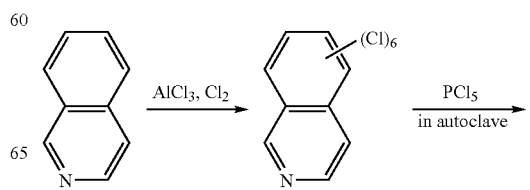

-continued

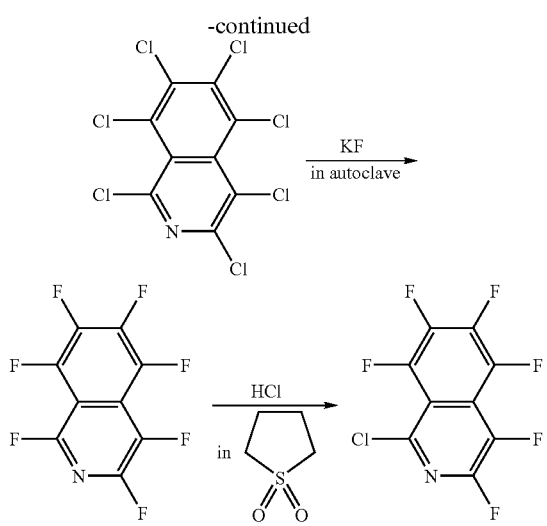

It is easy to successively synthesize the following compounds in the same manner as in Example 11 except for using 3,4,5,6-tetrafluorophenylboronic acid and the above-synthesized 1-chloro-3,4,5,6,7,8-hexafluoroisoquinoline instead of the 4-methylphenylboronic acid and 1-chloroisoquinoline, respectively, in Example 11.
Tetrakis[1-(3,4,5,6-tetrafluorophenyl)-3,4,5,6,7,8-hexafluoroisoquinoline-$C^2$,N](μ-dichloro)diiridium (III) (Example Compound No 709).
Bis[1-(3,4,5,6-tetrafluorophenyl)-3,4,5,6,7,8-hexafluoroisoquinoline-$C^2$,N](acetylacetonato)iridium (III) (Example Compound No. 457).
Tris[1-(3,4,5,6-tetrafluorophenyl)-3,4,5,6,7,8-hexafluoroisoquinoline-$C^2$,N]iridium (III) (Example Compound No. 454).

Example 56

It is easy to successively synthesize the following compounds in the same manner as in Example 11 except for using 3-isopropylphenylboronic acid (made by Lancaster Co.) instead of the 4-methylphenylboronic acid in Example 11
Tetrakis[1-(5-isopropylphenyl)isoquinoline-$C^2$,N](μ-dichloro)iridium (III),
Bis[1-(5-isopropylphenyl)isoquinoline-$C^2$,N]-(acetylacetonato)iridium (III),
Tris[1-(5-isopropylphenyl)isoquinoline-$C^2$,N]-iridium (III) (Example Compound No. 315).

Example 57

It is easy to successively synthesize the following compounds in the same manner as in Example 11 except for using 3-butylphenylboronic acid instead of the 4-methylphenylboronic acid in Example 11.
Tetrakis[1-(5-butylphenyl)isoquinoline-$C^2$,N](μ-dichloro)iridium (III) (Example Compound No. 725),
Bis[1-(5-butylphenyl)isoquinoline-$C^2$,N]-(acetylacetonato)iridium (III),
Tris[1-(5-butylphenyl)isoquinoline-$C^2$,N]-iridium (III) (Example Compound No. 316).

Example 58

It is easy to successively synthesize the following compounds in the same manner as in Example 11 except for using 3-octylphenylboronic acid (made by Lancaster Co.) instead of the 4-methylphenylboronic acid in Example 11.
Tetrakis[1-(5-octylphenyl)isoquinoline-$C^2$,N(μ-dichloro)iridium (III) (Example Compound No. 730),
Bis[1-(5-octylphenyl)isoquinoline-$C^2$,N]-(acetylacetonato) iridium (III),
Tris[1-(5-octylphenyl)isoquinoline-$C^2$,N]-iridium (III) (Example Compound No. 321).

Example 59

It is easy to successively synthesize the following compounds in the same manner as in Example 11 except for using 3-methoxyphenylboronic acid (made by Lancaster Co.) instead of the 4-methylphenylboronic acid in Example 11.
Tetrakis(1-(5-methoxyphenyl)isoquinoline-$C^2$,N(μ-dichloro)iridium (III),
Bis[1-(5-methoxyphenyl)isoquinoline-$C^2$,N]-(acetylacetonato)iridium (III),
Tris[1-(5-methoxyphenyl)isoquinoline-$C^2$,N]-iridium (III) (Example Compound No. 375).

Example 61

It is easy to successively synthesize the following compounds in the same manner as in Example 11 except for using 4-trifluoromethoxyphenylboronic acid (made by Aldrich Co-) and 1-chloro-4-trifluoromethylisoquinoline instead of the 4-methylphenylboronic acid and 1-chloroisoquinoline, respectively, in Example 11.
Tetrakis[1-(4-trifluoromethoxyphenyl)-4-trifluoromethylisoquinoline-$C^2$,N](μ-dichloro)diiridium (III).
Bis[1-(4-trifluoromethoxyphenyl)-4-trifluoromethylisoquinoline-$C^2$,N](acetylacetonato)iridium (III).
Tris[1-(trifluoromethoxyphenyl)-4-trifluoromethylisoquinoline-$C^2$,N]iridium (III) (Example Compound No. 411).

Example 62

It is easy to successively synthesize the following compounds in the same manner as in Example 11 except for using 4-trifluoromethoxyphenylboronic acid and 1-chloro-5-trifluoromethylisoquinoline instead of the 4-methylphenylboronic acid and 1-chloroisoquinoline, respectively, in Example 11.
Tetrakis[1-(4-trifluoromethoxyphenyl)-5-trifluoromethylisoquinoline-$C^2$,N](μ-dichloro)diiridium (III).
Bis[1-(4-trifluoromethoxyphenyl)-5-trifluoromethylisoquinoline-$C^2$,N](acetylacetonato)iridium (III).
Tris[1-(4-trifluoromethoxyphenyl)-5-trifluoromethylisoquinoline-$C^2$,N]iridium (III) (Example Compound No. 410).

Example 63

It is easy to successively synthesize the following compounds in the same manner as in Example 11 except for using 4-trifluoromethoxyphenylboronic acid and 1-chloro-4-fluoroisoquinoline instead of the 4-methylphenylboronic acid and 1-chloroisoquinoline, respectively, in Example 11.
Tetrakis[1-(4-trifluoromethoxyphenyl)-4-fluoroisoquinoline-$C^2$,N](μ-dichloro)diiridium (III).
Bis[1-(4-trifluoromethoxyphenyl)-4-fluoroisoquinoline-$C^2$, N](acetylacetonato)iridium (III).
Tris[1-(4-trifluoromethoxyphenyl)-4-fluoroisoquinoline-$C^2$, N]iridium (III) (Example Compound No. 409).

Example 64

Bis[1-(4-propylphenyl)isoquinoline-$C^2$,N]-(acetylacetonato)iridium (III) is synthesized in a similar manner as in Example 11 by using 1-(4-propylphenyl)isoquinoline of Example 29 and via tetrakis[1-(4-propylphenyl)isoquinoline-$C^2$,N](μ-dichloro)diiridium (III). It is easy to synthesize bis[1-(4-propylphenyl)isoquinoline-$C^2$,N](1-phenylisoquinoline-$C^2$,N)iridium (III) (Example Compound No 283) by reacting the compound with 1-phenylisoquinoline of Example 7.

Example 65

Bis[1-phenylisoquinoline-$C^2$,N]-(acetyl-acetonato)iridium (III) is synthesized in a similar manner as in Example 11 by using 1-phenylisoquinoline instead of 1-(4-methylphenyl)isoquinoline of Example 11 and via tetrakis[1-phenylisoquinoline-$C^2$,N](μ-dichloro)diiridium (III). It is easy to synthesize bis(1-isoquinoline-$C^2$,N)[1-(4-propylphenyl)-isoquinoline-$C^2$,N)Iridium (III) (Example Compound No. 299) by reacting the compound with 1-(4-propylphenyl)-isoquinoline of Example 29.

Example 66

It is easy to synthesize the following compound in a similar manner as in Example 22 except for using 1-(4-hexylphenyl)isoquinoline instead of the 2-phenylpyridine used in Example 22.
Bis[1-(4-hexylphenyl)isoquinoline-$C^2$,N](1-phenylisoquinoline-$C^2$,N)iridium (III) (Example Compound No. 287).

Example 67

It is easy to synthesize the following compound in a similar manner as in Example 22 except for using 1-phenylisoquinoline and 1-(4-hexylphenyl)-isoquinoline instead of the 2-phenylpyridine and 1-phenylisoquinoline, respectively, in Example 22.
Bis(1-phenylisoquinoline-$C^2$,N)[1-(4-hexyphenyl)isoquinoline-$C^2$,N]iridium (III) (Example Compound No. 303).

Example 68

It is easy to synthesize the following compound in a similar manner as in Example 22 except for using 1-(4-octylphenyl)isoquinoline instead of the 2-phenylpyridine in Example 22.
Bis[1-(4-octylphenyl)isoquinoline-$C^2$,N](1-phenylisoquinoline-$C^2$,N)iridium (III) (Example Compound No. 289).

Example 69

It is easy to synthesize the following compound in a similar manner as in Example 22 except for using 1-phenylisoquinoline and 1-(4-octylphenyl)-isoquinoline instead of the 2-phenylpyridine and 1-phenylisoquinoline, respectively, in Example 22.
Bis(1-phenylisoquinoline-$C^2$,N)[1-(4-octylphenyl)isoquinoline-$C^2$,N]iridium (III) (Example Compound No. 305).

Example 70

Preparation of Activated Copper Powder 400 g (2.5 mmole) of copper sulfate is dissolved in 2500 ml of hot water and then cooled, and 219 mg (3.35 mole) of zinc powder is added thereto at the same temperature. After washing with water by decantation, 5%-hydrochloric acid is added thereto until hydrogen gas generation is terminated to dissolve the zinc. Copper powder is recovered by filtration, washed with water and then with methanol and dried to obtain 149 g of activated copper powder.

It is easy to synthesize 4-perfluoro-hexylphenylboronic acid by using the activated copper powder along the following path:

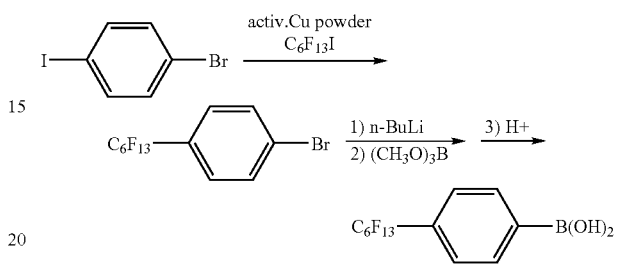

It is easy to successively synthesize the following compounds in the same manner as in Example 11 except for using 4-perfluorohexylphenylboronic acid instead of the 4-methylphenylboronic acid in Example 11.
Tetrakis[I (4-perfluorohexylphenyl)isoquinoline-$C^2$,N](μ-dichloro)iridium (III) (Example Compound No. 715),
Bis[1-(4-perfluorohexylpnenyl)isoquinoline-$C^2$,N]-(acetylacetonato)iridium (III),
Tris[1-(4-perfluorohexylphenyl)isoquinoline-$C^2$,N]-iridium (III) (Example Compound No. 475).

Example 71

It is easy to successively synthesize the following compounds in the same manner as in Example 11 except for using 4-perfluorohexylphenylboronic acid and 1-chloro-4-fluoroisoquinoline instead of the 4-methylphenylboronic acid and 1-chloroisoquinoline, respectively, in Example 11.
Tetrakis[1-(4-perfluorohexylphenyl)-4-fluoroisoquinoline-$C^2$,N](μ-dichloro),diiridium (III).
Bis[1-(4-perfluorohexylphenyl)-4-fluoroisoquinoline-$C^2$,N](acetylacetonato)iridium (III).
Tris[1-(4-perfluorohexylphenyl) 4-fluoroisoquinoline-$C^2$,N]iridium (III) (Example Compound No. 478).

Example 72

It is easy to successively synthesize the following compounds in the same manner as in Example 11 except for using 4-perfluorohexylphenylboronic acid and 1-chloro-4-trifluoromethylisoquinoline instead of the 4-methylphenylboronic acid and 1-chloroisoquinoline, respectively, in Example 11.
Tetrakis[1-(4-perfluorohexylphenyl)-4-trifluoromethylisoquinoline-$C^2$,N](μ-dichloro)diiridium (III).
Bis[1-(4-perfluorohexylphenyl)-4-trifluoromethylisoquinoline-$C^2$,N](acetylacetonato)iridium (III).
Tris[1-(4-perfluorohexylphenyl)-4-trifluoromethylisoquinoline-$C^2$,N]iridium (III) (Example Compound No. 477).

Example 73

It is easy to successively synthesize the following compounds in the same manner as in Example 11 except for using 4-perfluorohexylphenylboronic acid and 1-chloro-5-fluoroisoquinoline instead of the 4-methylphenylboronic acid and 1-chloroisoquinoline, respectively, in Example 11.

Tetrakis[1-(4-perfluorohexylphenyl)-5-trifluoromethyliso-
quinoline-C²,N](μ-dichloro)diiridium (III).
Bis[1-(4-perfluorohexylphenyl)-5-trifluoromethylisoquino-
line-C²,N](acetylacetonato)iridium (III).
Tris[1-(4-perfluorohexylphenyl)-5-trifluoromethylisoquino-
line-C²,N]iridium (III) (Example Compound No. 476).

Example 74

It is easy to synthesize the following compound in a similar manner as in Example 22 except for using 1-(4-perfluorohexylphenyl)isoquinoline instead of the 2-phenylpyridine in Example 22.
Bis[1-(4-perfluorohexylphenyl)isoquinoline-C²,N](1-phenylisoquinoline-C²,N)iridium (III) (Example Compound No. 479).

Example 75

It is easy to synthesize the following compound in a similar manner as in Example 22 except for using 1-phenylisoquinoline and 1-(4-perfluorohexylphenyl)isoquinoline instead of the 2-phenylpyridine and 1-phenylisoquinoline, respectively, in Example 22.
Bis 1-phenylisoquinoline-C²,N)[1-(4-perfluorohexylphenyl)isoquinoline-C²,N]iridium (III) (Example Compound No. 480).

Example 76

It is easy to synthesize 4-(1H,1H,2H,2H-perfluoropentyloxy)phenylboronic acid along the following the path:

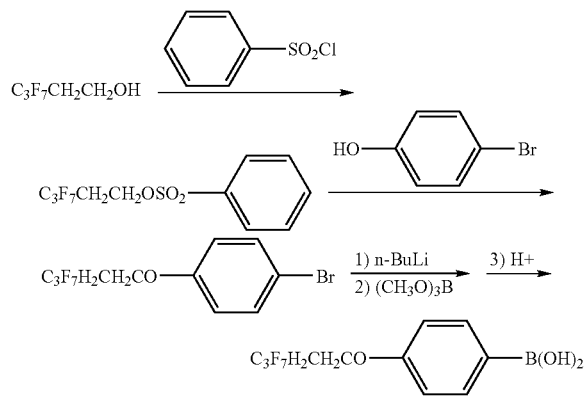

It is easy to successively synthesize the following compounds in the same manner as in Example 11 except for using 4-(1H,1H,2H,2H-perfluoropentyloxy)-phenylboronic acid instead of the 4-methylphenylboronic acid in Example 11.
Tetrakis{1-[4-(1H,1H,2H,2H-perfluoropentyloxy)-phenyl]
isoquinoline-C²,N}(μ-dichloro)iridium (III),
Bis{1-[4-(1H,1H,2H,2H-perfluoropentyloxy)phenyl]-iso-
quinoline-C²,N}-(acetylacetonato)iridium (III),
Tris{1-[4-(1H,1H,2H,2H-perfluoropentyloxyethylphenyl]
isoquinoline-C²,N}-iridium (III) (Example Compound No. 469).

Example 77

It is easy to synthesize the following compound in a similar manner as in Example 22 except for using 1-[4-(1H,1H,2H,2H-perfluoropentyloxy)-isoquinoline instead of the 2-phenylpyridine in Example 22.

Bis{1-[4-(1H,1H,2H,2H]-perfluoropentyloxy)-phenyl]
isoquinoline-C²,N}(1-phenylisoquinoline-C²,N)-iridium
(III) (Example Compound No. 470).

Example 78

It is easy to synthesize the following compound in a similar manner as in Example 22 except for using 1-phenylisoquinoline and 1-[4-(1H,1H,2H,2H-perfluoropentyloxy)phenyl]isoquinoline instead of the 2-phenylpyridine and 1-phenylisoquinoline, respectively, in Example 22.
Bis(1-phenylisoquinoline-C²,N){1-[4-(1H,1H,2H,2H-perfluoropentyloxy)phenyl]isoquinoline-C²,N}iridium (III) (Example Compound No. 471).

Example 79

It is easy to synthesize 4-(1H,1H-perfluoro-heptyloxy) phenylboronic acid along the following path:

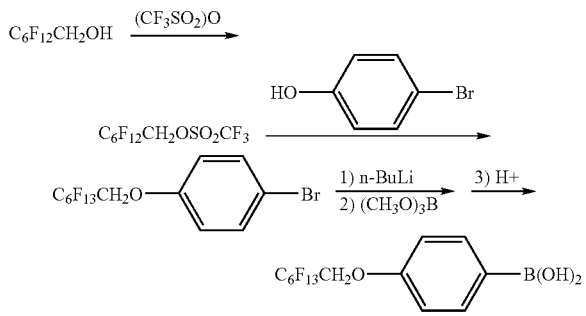

It is easy to successively synthesize the following compounds in the same manner as in example 11 except for using 4-(1H,1H-perfluoroheptyloxy)-phenylboronic acid instead of the 4-methylphenyl-boronic acid in Example 11.
Tetrakis{1-[4-(1H,1H-perfluoroheptyloxy)phenyl]-iso-
quinoline-C²,N}(μ-dichloro)iridium (III),
Bis{1-[4-(1H, 1H-perfluoroheptyloxy)phenyl]-isoquino-
line-C²,N}-(acetylacetonato)iridium (III),
Tris{1-[4-(1H,1H-perfluoroheptyloxy)phenyl]-isoquino-
line-C²,N}-iridium (III) (Example Compound No. 481).

Example 80

It is easy to synthesize the following compound in a similar manner as in Example 22 except for using 1-[4-(1H,1H-perfluoroheptyloxy)phenyl]-isoquinoline instead of the 2-phenylpyridine in Example 22.
Bis{1-[4-(1H,1H-perfluoroheptyloxy)phenyl]-isoquino-
line-C²,N}(1-phenylisoquinoline-C²,N)iridium (III) (Example Compound No. 483).

Example 81

It is easy to synthesize the following compound in a similar manner as in Example 22 except for using 1-phenylisoquinoline and 1-[4-(1H,1H-perfluoroheptyloxy)phenyl]isoquinoline instead of the 2-phenylpyridine and 1-phenylisoquinoline, respectively, in Example 22.
Bis(1-phenylisoquinoline-C²,N){1-[4-(1H,1H-perfluoroheptyloxy)phenyl]isoquinoline-C²,N}iridium (III) (Example Compound No. 484).

Example 82

It is easy to successively synthesize the following compounds in the same manner as in Example 11 except for using phenylboronic acid and 1-chloro-4-hexylisoquinoline instead of the 4-methylphenylboronic acid and 1-chloroisoquinoline, respectively, in Example 11.

Tetrakis[1-phenyl-4-hexylisoquinoline-$C^2$,N]($\mu$-dichloro)diiridium (III).

Bis[1-phenyl-4-hexylisoquinoline-$C^2$,N](acetyl-acetonato)iridium (III).

Tris[1-phenyl-4-hexylisoquinoline-$C^2$,N]iridium (111) (Example Compound No. 156).

Example 83

It is easy to successively synthesize the following compounds in the same manner as in Example 11 except for using phenylboronic acid and 1-chloro-5-fluoroisoquinoline instead of the 4-methylphenylboronic acid and 1-chloroisoquinoline, respectively, in Example 11.

Tetrakis(1-phenyl-5-octylisoquinoline-$C^2$,N)($\mu$-dichloro)diiridium (III).

Bis(1-phenyl-5-octylisoquinoline-$C^2$,N)(acetyl-acetonato)iridium (III).

Tris(1-phenyl-5-octylisoquinoline-$C^2$,N)iridium (III) (Example Compound No. 220).

Example 84

It is easy to successively synthesize the following compounds in the same manner as in Example 11 except for using 3-heptyloxyphenylboronic acid (made by Lancaster Co.) instead of the 4-methylphenylboronic acid in Example 11.

Tetrakis[1-(5-heptyloxyphenyl)isoquinoline-$C^2$,N]($\mu$-dichloro)iridium (III), Bis[1-(5-heptyloxyphenyl)isoquinoline-$C^2$,N]-(acetylacetonato)iridium (III), Tris[1-(5-heptyloxyphenyl)isoquinoline-$C^2$,N]-iridium (III) (Example Compound No. 270).

Example 85

It is easy to synthesize 1-chloro-7-azaisoquinoline by using 2,6-dihydroxy-4-methyl-3-pyridylcarbonitrile (made by Aldrich Co., catalog 37, 947-6) along the following path described in U.S. Pat. No. 4,859,671:

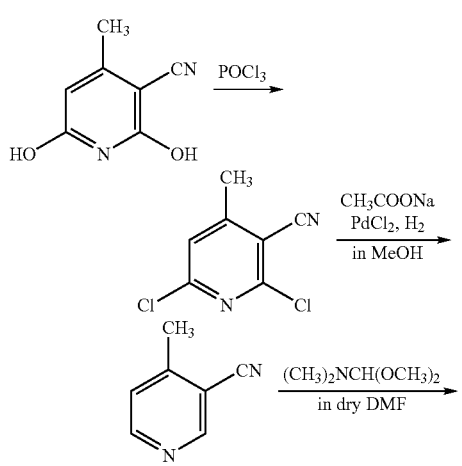

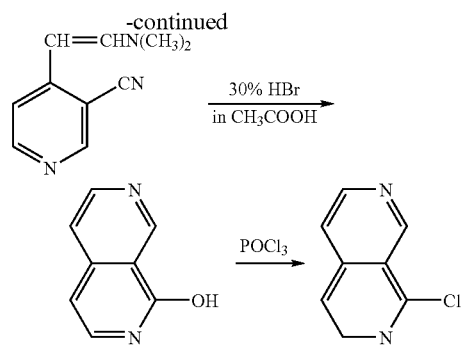

It is easy to synthesize 1-phenyl-7-azaisoquinoline by using 1-chloro-7-azaisoquinoline instead of the 1-chloroisoquinoline in Example 7, and successively synthesize tetrakis (1-phenyl-7-azaisoquinoline-$C^2$,N)($\mu$-dichloro)diiridium (III) and bis(1-phenyl-7-azaisoquinoline-$C^2$,N)(acetylacetonato)-iridium (III) to obtain tris(1-phenyl-7-azaiso-quinoline-$C^2$,N)iridium (III) (Example Compound No. 783) in-a similar manner as in Example 11.

Example 86

It is easy to synthesize 1-hydroxy-5-azaisoquinoline by using 3-methyl-picolinonitrile (made by Aldrich Co., catalog 51, 273-7) along the following path described in U.S. Pat. No. 4,176,183 and synthesize 1-chloro-5-azaisoquinoline in a similar manner as in Example 85.

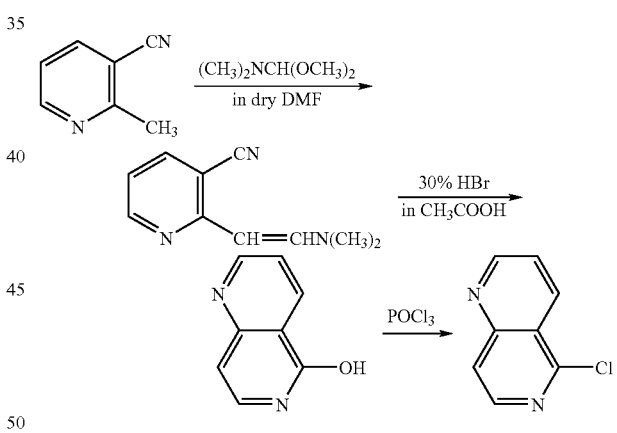

It is easy to synthesize 1-phenyl-5-azaisoquinoline by using 1-chloro-5-azaisoquinoline instead of the 1-chloroisoquinoline in Example 7, and successively synthesize tetrakis (1-phenyl-5-azaisoquinoline-$C^2$,N)($\mu$-dichloro)diiridium (III) (Example Compound No. 763) and bis(1-phenyl-5-azaisoquinoline-$C^2$,N)(acetylacetonato)iridium (III) to obtain tris(1-phenyl-5-azaisoquinoline-$C^2$,N)iridium (III) (Example Compound No. 640) in a similar manner as in Example 11.

Examples 87-95

Devices having a similar structure as in Example 1 were prepared and evaluated. Details of device structures, layer thicknesses and evaluation results are shown in Table 25.

TABLE 25

| | Device structure* | | | | current | luminance | current efficiency | | power efficiency | |
|---|---|---|---|---|---|---|---|---|---|---|
| Example No. | H.T.L. | luminescence layer | | E.D.P.L. | E.T.L. | mA/cm2 | cd/m2 | cd/A | | lm/W | |
| | | | | | | | | 100 cd/m2 | 300 cd/m2 | 100 cd/m2 | 300 cd/m2 |
| 87 | αNPD 40 nm | CBP: Compound No. 413(7%) 40 nm | | BCP 10 nm | Alq 3 20 nm | 10 volts 114 | 10 volts 800 | 1 | 0.86 | 0.4 | 0.3 |
| 88 | αNPD 40 | CBP: Compound No. 432(7%) 40 | | BCP 10 | Alq 3 20 | 10 V 26 | 10 V 1248 | 100 cd 5.9 | 300 cd 5.5 | 100 cd 2.8 | 300 cd 2.1 |
| 89 | αNPD 40 | CBP: Compound No. 408(5%) 40 | | BCP 10 | Alq 3 60 | 10 V 9 | 10 V 480 | 100 cd 6.6 | 300 cd 5.6 | 100 cd 2.4 | 300 cd 1.8 |
| 90 | αNPD 40 | CBP: Compound No. 433(5%) 40 | | BCP 10 | Alq 3 60 | 10 V 12 | 10 V 700 | 100 cd 6.69 | 300 cd 6.4 | 100 cd 2.93 | 300 cd 2.32 |
| 91 | αNPD 40 | CBP: Compound No. 433(7%) 40 | | BCP 10 | Alq 3 60 | 10 V 12.2 | 876 | 100 cd 8.6 | 300 cd 7.8 | 100 cd 3.82 | 300 cd 2.9 |
| 92 | αNPD 40 | CBP: Compound No. 433(9%) 40 | | BCP 10 | Alq 3 60 | 10 V 18 | 1180 | 100 cd 7.5 | 300 cd 7.2 | 100 cd 3.86 | 300 cd 2.9 |
| 93 | αNPD 40 | CBP: Compound No. 517(7%) 40 | | BCP 10 | Alq 3 60 | 10 V 3.3 | 185 | 100 cd 5.75 | 300 cd 5.42 | 100 cd 1.95 | 300 cd 1.54 |
| 94 | αNPD 40 | CBP: Compound No. 516(7%) 40 | | Balq 10 | Alq 3 60 | 10 V 12.5 | 611 | 100 cd 5.85 | 300 cd 5.25 | 100 cd 2.42 | 300 cd 1.80 |
| 95 | αNPD 40 | CBP: Ir Compound No. 412(7%) 40 | | Balq 10 | Alq 3 60 | 10 V 15 | 778 | 100 cd 5.3 | 300 cd 5.4 | 100 cd 2.2 | 300 cd 1.9 |

*H.T.L. = hole-transporting layer
E.D.P.L. = exciton diffusion-prevention layer
E.T.L. = electron-transporting layer Balq used in the exciton diffusion-prevention layer used in Examples 94 and 95 has a structure shown below.

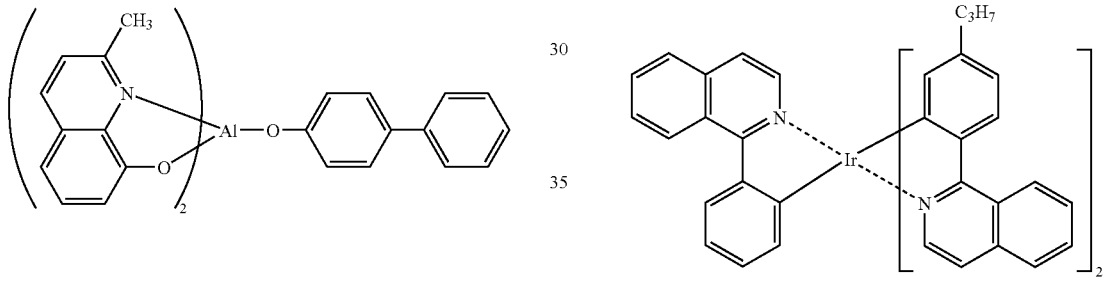

INDUSTRIAL APPLICABILITY

As described above, the luminescence device of the present invention using, as a luminescence center material, a metal coordination compound having a partial structure of the above formula (1) and particularly represented by the above formula (3) is an excellent device which not only allows high-efficiency luminescence but also retains a high luminance for a long period and allows luminescence of longer wavelength. Further, the luminescence device of the present invention shows excellent performances as a red display device.

What is claimed is:

1. A metal coordination compound represented by any one of formulas 27 to (33):

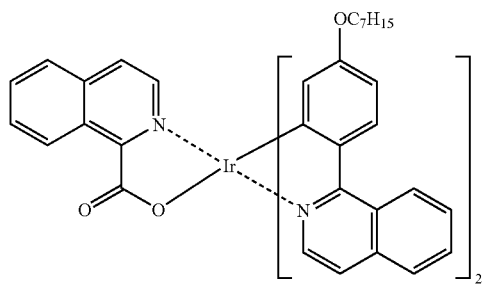

(27)

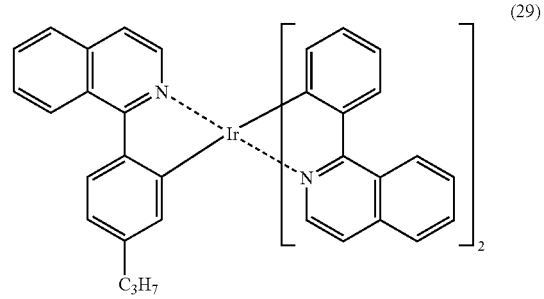

(28)

(29)

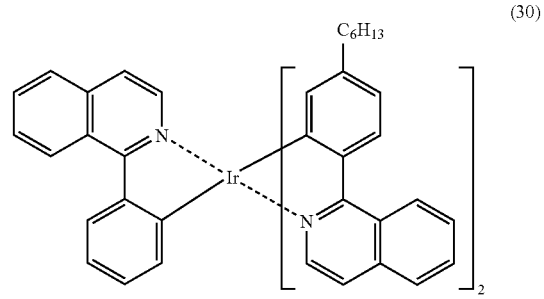

(30)

-continued

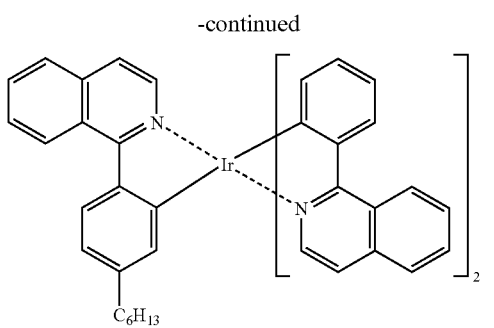

(31)

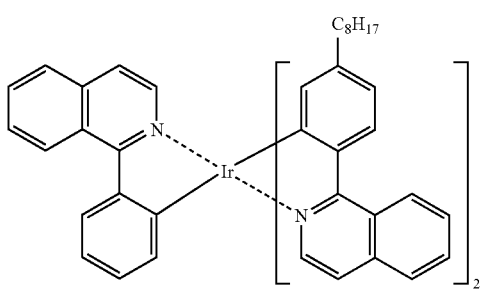

(32)

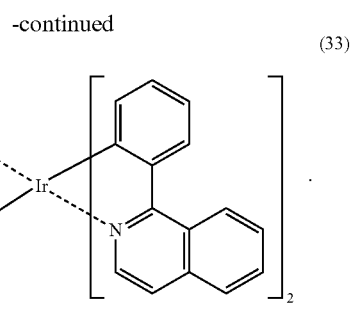

(33)

2. An organic luminescence device comprising:
an anode and a cathode; and
an organic layer disposed between the anode and cathode,
wherein the organic layer comprises a metal coordination compound according to claim 1.

3. A picture display apparatus comprising:
an organic luminescence device according to claim 2; and
means for supplying an electric signal to the organic luminescence device.

* * * * *